(12) United States Patent
Jackson et al.

(10) Patent No.: US 12,186,548 B2
(45) Date of Patent: Jan. 7, 2025

(54) NON-INVASIVE BRAIN STIMULATION

(71) Applicant: Neurotherapeutics Ltd, Nottingham (GB)

(72) Inventors: Stephen Jackson, Nottingham (GB); Georgina Jackson, Nottingham (GB)

(73) Assignee: The University of Nottingham, Nottingham (GB)

( * ) Notice: Subject to any disclaimer, the term of this patent is extended or adjusted under 35 U.S.C. 154(b) by 281 days.

(21) Appl. No.: 17/626,449

(22) PCT Filed: Jul. 13, 2020

(86) PCT No.: PCT/IB2020/056586
§ 371 (c)(1),
(2) Date: Jan. 11, 2022

(87) PCT Pub. No.: WO2021/005584
PCT Pub. Date: Jan. 14, 2021

(65) Prior Publication Data
US 2022/0401721 A1 Dec. 22, 2022

(30) Foreign Application Priority Data

Jul. 11, 2019 (GB) .................................. 1909983
May 21, 2020 (GB) .................................. 2007622

(51) Int. Cl.
*A61N 1/04* (2006.01)
*A61N 1/36* (2006.01)

(52) U.S. Cl.
CPC ....... *A61N 1/0456* (2013.01); *A61N 1/36034* (2017.08)

(58) Field of Classification Search
CPC .......................... A61N 1/0456; A61N 1/36034
See application file for complete search history.

(56) References Cited

U.S. PATENT DOCUMENTS

| | | | | |
|---|---|---|---|---|
| 5,391,081 A | * | 2/1995 | Lampotang | G09B 23/28 434/262 |
| 6,066,163 A | * | 5/2000 | John | G16H 20/40 607/45 |

(Continued)

FOREIGN PATENT DOCUMENTS

| | | |
|---|---|---|
| EP | 3498332 A1 | 6/2019 |
| WO | 2018187241 A1 | 10/2018 |

OTHER PUBLICATIONS

International Search Report and Written Opinion in Intl. App. No. PCT/IB2020/056586, mailed on Sep. 18, 2020.

(Continued)

*Primary Examiner* — Eric D. Bertram
(74) *Attorney, Agent, or Firm* — Sheppard Mullin Richter & Hampton LLP

(57) ABSTRACT

The present invention relates to an electrical nerve stimulator configured to deliver an electrical signal to a user to entrain Mu-band neural oscillations and/or Beta-band neural oscillations. The electrical nerve stimulator may be used in the treatment of neurological conditions associated with desynchronization of neural oscillations, such as Tourette's syndrome. The electrical nerve stimulator may be wearable on a wrist of a user, and may be configured to deliver rhythmic stimulation at a frequency falling within the same frequency range of Mu-band or Beta-band neural oscillations. The invention provides a convenient means of treating conditions such as Tourette's syndrome without the need for specialist medical equipment or facilities. Also disclosed is a method of delivering an electrical signal to a user to entrain Mu-band neural oscillations and/or Beta-band neural oscillations.

16 Claims, 61 Drawing Sheets

(56) References Cited

U.S. PATENT DOCUMENTS

| | | | | |
|---|---|---|---|---|
| 2002/0138116 A1* | 9/2002 | Bertolucci | ......... | A61N 1/36017 |
| | | | | 607/72 |
| 2008/0208287 A1* | 8/2008 | Palermo | ................ | A61N 1/323 |
| | | | | 607/3 |
| 2008/0249430 A1* | 10/2008 | John | ...................... | A61B 5/372 |
| | | | | 600/544 |
| 2014/0142410 A1* | 5/2014 | Erb | ...................... | A61N 1/0456 |
| | | | | 600/383 |
| 2014/0163627 A1* | 6/2014 | Starr | .................. | A61M 5/1723 |
| | | | | 607/45 |
| 2018/0064942 A1 | 3/2018 | Franke et al. | | |
| 2018/0140843 A1* | 5/2018 | Kent | ...................... | A61N 1/025 |
| 2018/0353759 A1* | 12/2018 | Starr | ...................... | A61B 5/369 |
| 2019/0143113 A1* | 5/2019 | Wong | ................ | A61N 1/36014 |
| | | | | 607/48 |
| 2020/0061378 A1* | 2/2020 | Ganguly | ................ | A61B 5/374 |
| 2021/0402172 A1* | 12/2021 | Ross | ........................ | A61H 1/00 |

OTHER PUBLICATIONS

International Preliminary Report on Patentability in PCT/IB2020/056586, dated on Nov. 5, 2021.

\* cited by examiner

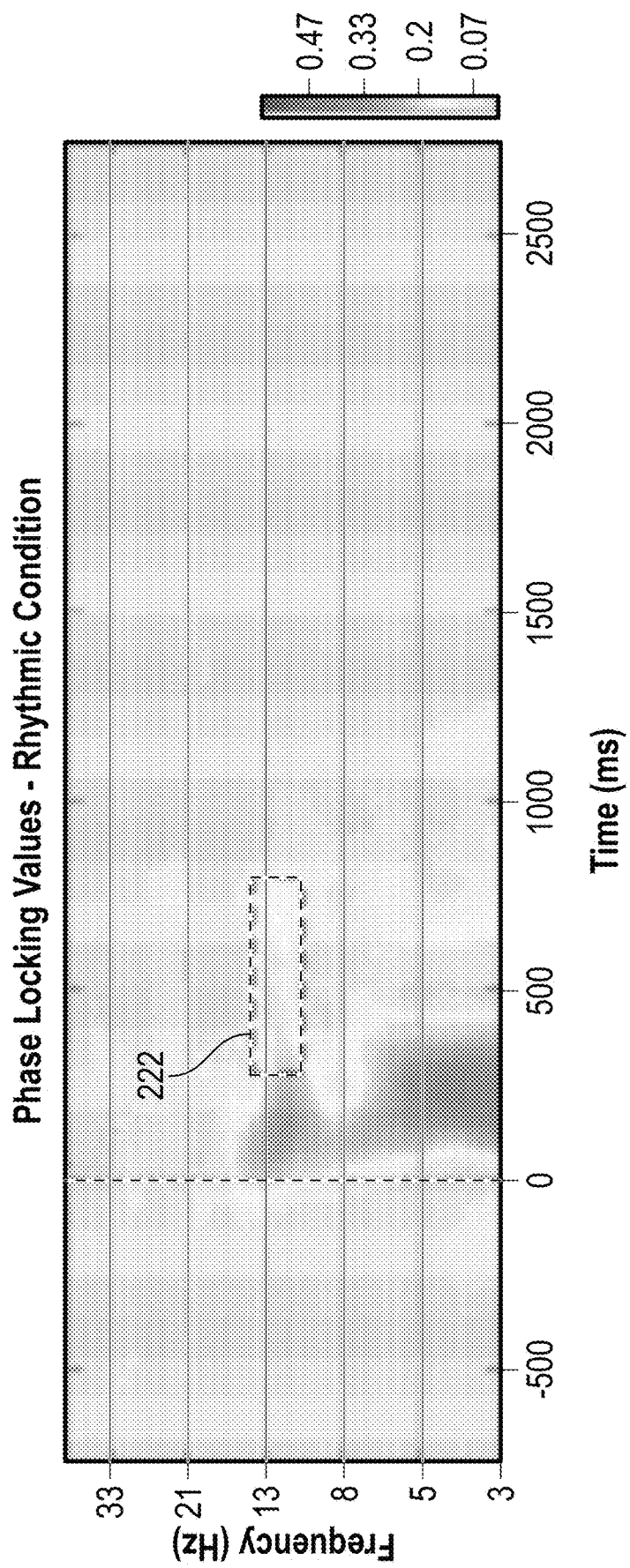

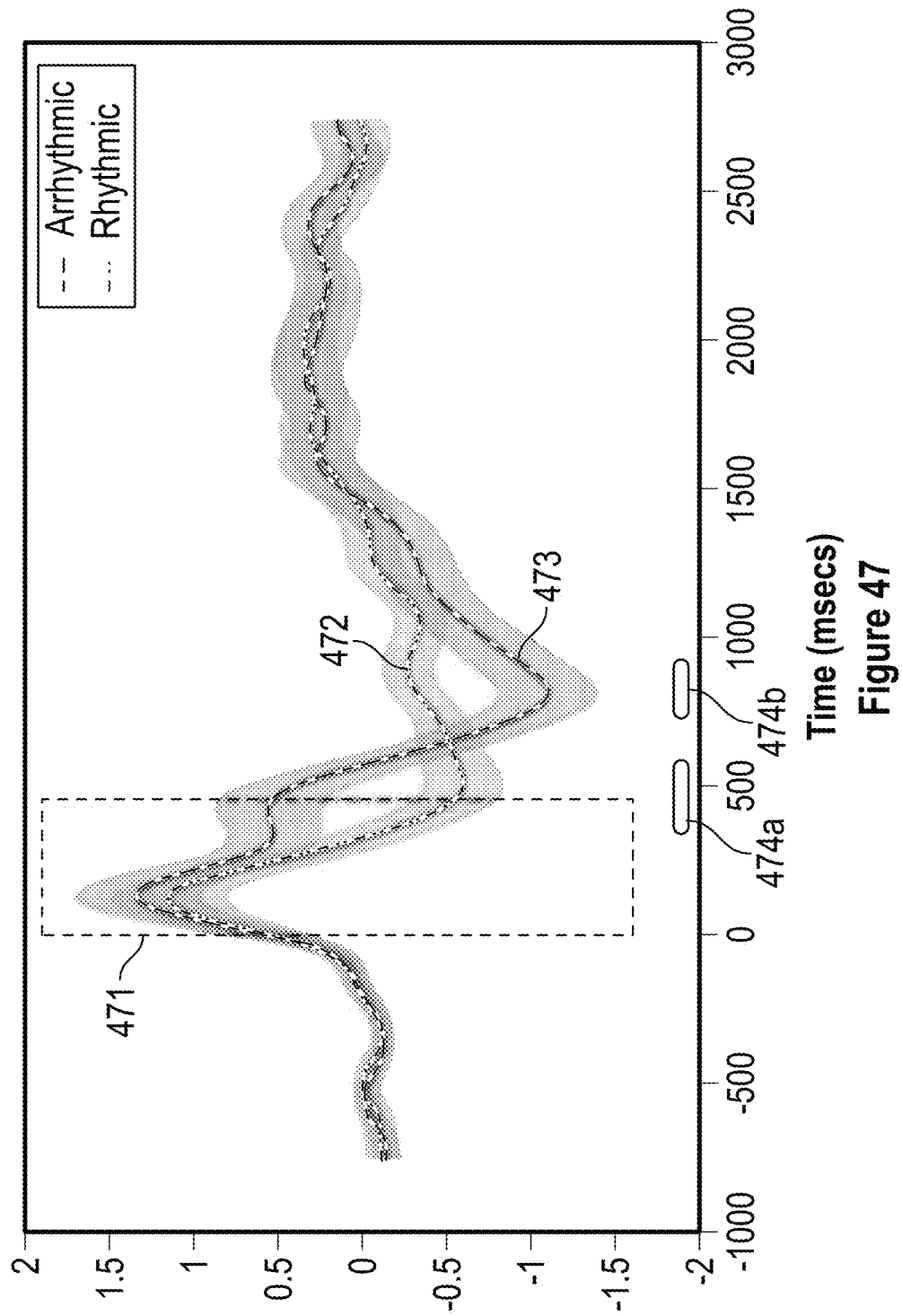

NON-INVASIVE BRAIN STIMULATION

CROSS-REFERENCE TO RELATED APPLICATIONS

The present application is a U.S. National Stage Application under 35 U.S.C. § 3.71 of International Patent Application No. PCT/IB2020/056586, filed on Jul. 13, 2020, which application claims the benefit of priority to GB Patent Application No. 1909983.7 filed on Jul. 11, 2019, and GB Patent Application No. 2007622.0, filed May 21, 2020, which are herein incorporated by reference in their entirety.

TECHNICAL FIELD

The present invention relates to the treatment of neurological disorders through the application of electrical signals to the brain. Embodiments of the invention include an electrical nerve stimulator and a method of using the stimulator.

BACKGROUND

Neural oscillations, or brainwaves, are rhythmic or repetitive patterns of neural activity in the central nervous system which govern the functions of the human body. Neural oscillations occur within different frequency bands. Two of these frequency bands, known as the Alpha/Mu-band (comprising neural oscillations within the range of 8-12 Hz) and the Beta-band (comprising neural oscillations within the range of 13-30 Hz) have long been associated with sensorimotor function. Sensorimotor function involves Alpha/Mu and Beta neural oscillations within the cortico-striato-thalamo-cortical (CSTC) brain circuit.

Motor function is associated with desynchronisation of Alpha/Mu and Beta neural oscillations within the CSTC circuit. Decreased synchronisation of Alpha/Mu-band and Beta-band neural oscillations has been associated with Tourette's syndrome (TS), which is characterised by involuntary movements and utterances, known as tics. In contrast, increased synchronisation of Beta-band neural oscillations has been associated with Parkinson's disease (PD), which is charactarised by loss of motor function (akinesia), slowness of motor function (bradykinesia) and tremors. These conditions have been linked with altered dopamine levels within the brain, with an excess of dopamine being linked to TS and a deficit of dopamine being linked to PD. This may be due to Alpha/Mu-band and/or Beta-band neural oscillations being governed by dopamine. Additional or alternative causes of TS include altered gamma-Aminobutyric acid (GABA) signalling, particularly within the striatum, and striatal disinhibition. This is illustrated in FIG. 1 which shows a striatal disinhibition model.

Modification of neural oscillations using electrical stimulation has previously been undertaken for motor function disorders, such as PD. EP3498332 describes one such device that uses a peripheral nerve stimulator to stimulate a peripheral nerve to treat PD by desynchronising or dephasing brain oscillations thought to drive the tremors.

Similarly, other electrical stimulation devices, such as transcutaneous electrical nerve simulation (TENS) machines focus on blocking signals from nerves from reaching the brain, as evident by their usage in pain management. In effect, TENS machines act on nerves within the spinal cord and block the pain signals. In particular, as described in EP3498332, TENS is thought to excite A-beta neurons that communicate proprioceptive sensory information into the same brain circuits that are abnormal in diseases including essential tremor (ET) and PD. However, brain signals from sufferers of the neurological disorders described above do not show such synchronised brain oscillations and also are not believed to react to such A-beta neurons.

It is therefore an object of the present invention to at least ameliorate the symptoms for suffers of such neurological disorders.

SUMMARY OF INVENTION

According to an aspect of the invention, there is provided an electrical nerve stimulator configured to deliver an electrical signal to a user to entrain Mu-band neural oscillations and/or Beta-band neural oscillations.

The term 'entrain' as used herein refers to an increase in power and synchrony of neural oscillations. Therefore, to 'entrain' Mu-band and/or Beta-band neural oscillations means to increase the power and synchrony of Mu-band and/or Beta-band neural oscillations respectively. The term 'synchrony' may also be referred to as phase alignment.

The present invention acts to entrain movement related brain oscillations to reduce a somatosensory urge that precedes tics in Tourette's syndrome suffers and other somatosensory related illnesses or syndromes.

The electrical nerve stimulator may comprise a power source, a controller, and an electrode. A conducting part of the electrode may comprise stainless steel. The electrode may comprises a bar electrode. The electrode may comprise a first part and a second part separate from the first part. A maximum distance between the first part and the second part may be 30 mm. One or both of the first part and the second part comprises a disc. One or both of the first part and the second part may comprise a diameter of 8 mm.

A maximum distance between the first part and the second part may be within a range of 10-50 mm or 20-40 mm. One or both of the first part and the second part may comprise a diameter within a range of 4-12 mm or 6-10 mm.

This size of electrode can allow the stimulator to be used discretely by a patient.

The electrical nerve stimulator may be wearable on a wrist of a patient. This makes the device portable and convenient for the user. The present invention may provide an inconspicuous 'watch-like' device that could be worn on the wrist and used to deliver bursts of repetitive peripheral nerve stimulation as required.

The electrode may be attachable to a wrist of the user. The electrical nerve stimulator may comprise a wrist strap for attaching the electrical nerve stimulator to a wrist of a user. The wrist strap may be releasable.

The electrical nerve stimulator may be configured to stimulate a median nerve of the user.

The electrical nerve stimulator may be configured to stimulate a trigeminal nerve of the user.

The electrical nerve stimulator may be configured to deliver the electrical signal to a hemisphere of the brain of the user that is contralateral to the median nerve.

The electrical nerve stimulator may be configured to entrain Mu-band neural oscillations at a frequency within the range of 8-12 Hz and/or Beta-band neural oscillations at a frequency within the range of 13-30 Hz.

The electrical signal may comprise a frequency selected from the same frequency range as Mu-band or Beta-band neural oscillations. In other examples, the electrical signal may comprise a frequency selected from a range which falls outside the frequency ranges of Mu-band and Beta-band neural oscillations. An electrical signal comprising a frequency selected from a range which falls outside the frequency ranges of Mu-band and Beta-band neural oscillations may effect changes in neural oscillations outside of the Mu-band and Beta-band frequency ranges, which in turn may modulate Mu-band and/or Beta-band neural oscillations to cause entrainment of Mu-band and/or Beta-band neural oscillations.

The electrical signal may comprise a frequency within the range of 12-20 Hz; an amplitude of 1 mA; and/or a pulse width of 0.2 ms.

The electrical signal may comprise a frequency within the range of 12-30 Hz. The electrical signal may comprise a frequency within the range of 4-30 Hz. A frequency within the range of 12-30 Hz may be appropriate for applications of the invention to treatment of Tourette's syndrome.

The electrical signal may comprise a frequency within a range of 8-12 Hz to entrain Mu-band neural oscillations of the brain of a user. The electrical signal may comprise a frequency of 12 Hz to entrain Mu-band neural oscillations of the brain of a user. The electrical signal may comprise a frequency within a range of 13-30 Hz to entrain Beta-band neural oscillations of the brain of a user. The electrical signal may comprise a frequency of 19 Hz to entrain Beta-band neural oscillations of the brain of a user.

The electrical signal may comprise an amplitude within a range of 0.5-1.5 mA.

The electrical signal may comprise a duration of longer than 200 ms. The electrical signal may comprise more than two pulses. The electrical signal may comprise between three and ten pulses. The electrical signal may comprise any suitable number of pulses required to entrain Mu-band neural oscillations and/or Beta-band neural oscillations.

According to another aspect of the invention, there is provided a method of delivering an electrical signal to a user to entrain Mu-band neural oscillations and/or Beta-band neural oscillations. The electrical signal may comprise a frequency within the range of 12-20 Hz; an amplitude of 1 mA; and/or a pulse width of 0.2 ms. The method may comprise delivering the electrical signal for a duration longer than 200 ms. The method may comprise delivering the electrical signal via a median nerve of the user.

The electrical signal may comprise a frequency within a range of 8-12 Hz to entrain Mu-band neural oscillations of the brain of a user. The electrical signal may comprise a frequency of 12 Hz to entrain Mu-band neural oscillations of the brain of a user. The electrical signal may comprise a frequency within a range of 13-30 Hz to entrain Beta-band neural oscillations of the brain of a user. The electrical signal may comprise a frequency of 19 Hz to entrain Beta-band neural oscillations of the brain of a user.

The electrical signal may comprise an amplitude within a range of 0.5-1.5 mA.

The electrical signal may comprise a duration of longer than 200 ms. The electrical signal may comprise more than two pulses. The electrical signal may comprise between three and ten pulses. The electrical signal may comprise any suitable number of pulses required to entrain Mu-band neural oscillations and/or Beta-band neural oscillations.

According to another aspect of the invention, there is provided an electrical nerve stimulator configured to deliver an electrical signal to a user to reduce the power and/or synchrony of Mu-band neural oscillations and/or Beta-band neural oscillations.

This may act to reduce symptoms of Parkinson's disease, including akinesia, bradykinesia and tremors.

The electrical signal may comprise non-uniform intervals between pulses.

The electrical signal may comprise a frequency within the range of 4-30 Hz. A frequency within the range of 4-30 Hz may be appropriate for applications of the invention to treatment of Parkinson's disease.

The electrical nerve stimulator may comprise a power source, a controller, and an electrode. A conducting part of the electrode may comprise stainless steel. The electrode may comprises a bar electrode. The electrode may comprise a first part and a second part separate from the first part. A maximum distance between the first part and the second part may be 30 mm. One or both of the first part and the second part comprises a disc. One or both of the first part and the second part may comprise a diameter of 8 mm.

A maximum distance between the first part and the second part may be within a range of 10-50 mm or 20-40 mm. One or both of the first part and the second part may comprise a diameter within a range of 4-12 mm or 6-10 mm.

This size of electrode can allow the stimulator to be used discretely by a patient.

The electrical nerve stimulator may be wearable on a wrist of a patient. This makes the device portable and convenient for the user. The present invention may provide an inconspicuous 'watch-like' device that could be worn on the wrist and used to deliver bursts of repetitive peripheral nerve stimulation as required.

The electrode may be attachable to a wrist of the user. The electrical nerve stimulator may comprise a wrist strap for attaching the electrical nerve stimulator to a wrist of a user. The wrist strap may be releasable.

The electrical nerve stimulator may be configured to stimulate a median nerve of the user.

The electrical nerve stimulator may be configured to stimulate a trigeminal nerve of the user.

The electrical nerve stimulator may be configured to deliver the electrical signal to a hemisphere of the brain of the user that is contralateral to the median nerve.

According to another aspect of the invention, there is provided a method of delivering an electrical signal to a user to reduce the power and/or synchrony of Mu-band neural oscillations and/or Beta-band neural oscillations.

Except where mutually exclusive, any of the features of any of the above described aspects may be employed mutatis mutandis in any of the other above described aspects.

BRIEF DESCRIPTION OF THE FIGURES

Embodiments of the invention will now be described, by way of example only, with reference to the accompanying drawings:

FIG. 22b shows a time-frequency analysis of phase locking values (PLV) obtained from neural oscillations of each participant of the first study recorded at electrode C1 before, during and after delivery of a rhythmic pulse train;

FIG. 47 shows mean ERSP, obtained from Mu-band neural oscillations of each participant of the study recorded at electrode C1, against time before, during and after delivery of a rhythmic pulse train and before, during and after delivery of an arrhythmic pulse train.

DETAILED DESCRIPTION

In an example study, each of a plurality of participants completed 10 seconds of continuous first clenching and opening movements followed by 10 seconds of rest. Neural oscillations of each participant were recorded using magnetoencephalography (MEG) during the 10 seconds of movement and 10 seconds of rest. For each participant, event-related spectral perturbation (ERSP) was obtained for each frequency of recorded neural oscillations. ERSP is a measure of power of neural oscillations. Average ERSP, across the participants, for each frequency of recorded neural oscillations was then calculated.

Figure 1:
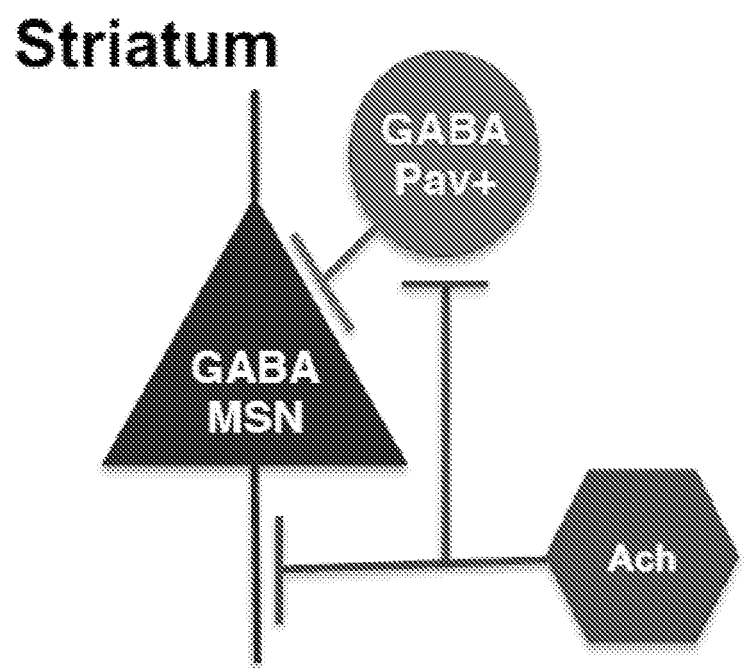
FIG. 1 shows a schematic of the striatal disinhibition model.
Figure 2:
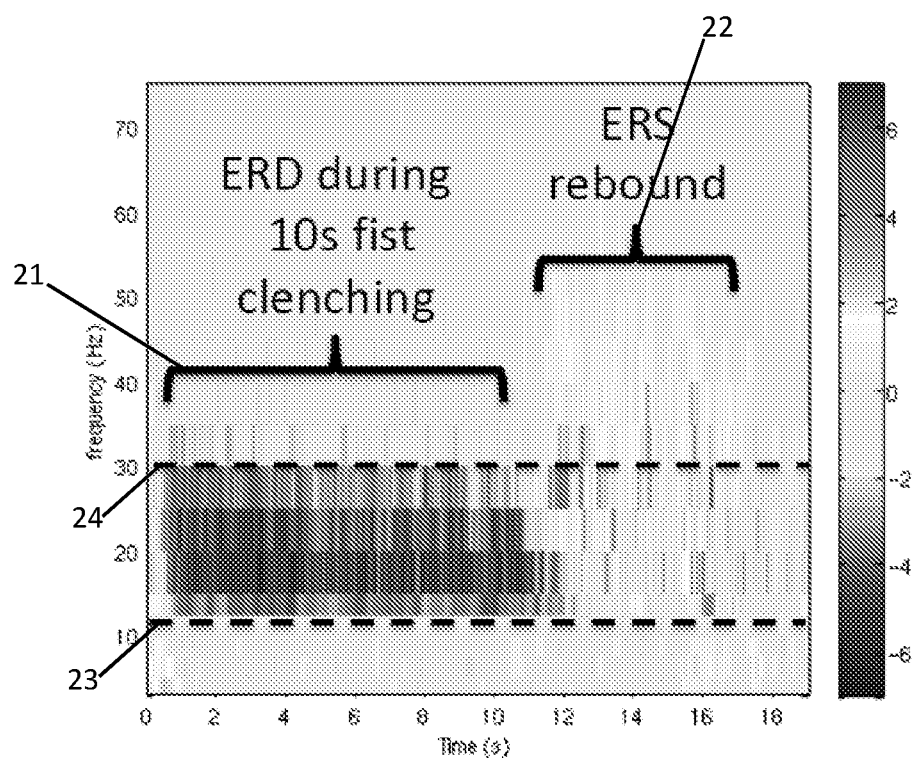
FIG. 2 shows a time-frequency analysis of event-related spectral perturbation (ERSP) obtained from neural oscillations recorded using magnetoencephalography (MEG)
Figure 3:
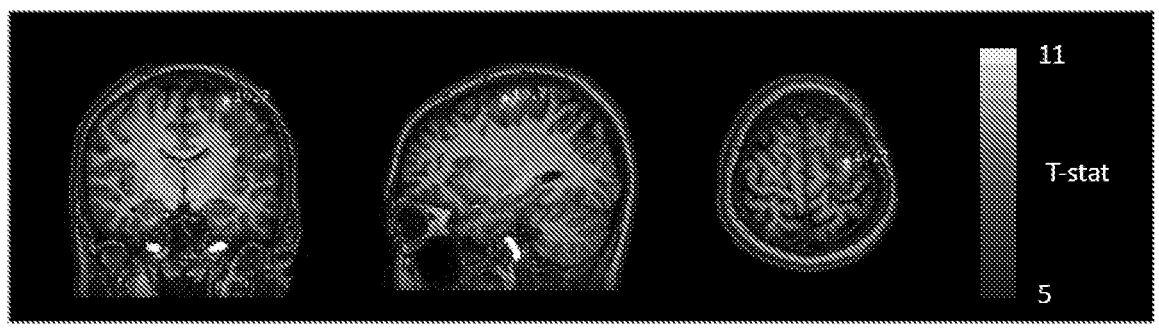
FIG. 3 shows the source of the neural oscillations of FIG. 2.

FIG. 2 shows a time-frequency analysis of average ERSP obtained from the example study. Time is shown on the x-axis and frequency is shown on the y-axis. The colouring of the graph shows ERSP according to the scale shown to the right of the graph. The source of the recorded neural oscillations was localised to the contralateral motor and premotor cortex, as shown in FIG. 3. Contralateral here refers to the motor and premotor cortex of the hemisphere of the brain on the opposite side of the body to that of the first performing the clenching and opening movements. The horizontal dashed lines 23, 24 indicate the frequency range of Beta-band neural oscillations. FIG. 2 shows a period 21 of event-related desynchronisation (ERD) of the neural oscillations during the 10 seconds of continuous first movements, followed by a period 22 of event-related synchronisation (ERS) during the 10 seconds of rest. FIG. 2 illustrates desynchronisation of Beta-band neural oscillations during movement, with synchronisation of Beta-band neural oscillations during a period of rest immediately following movement.

Figure 4:
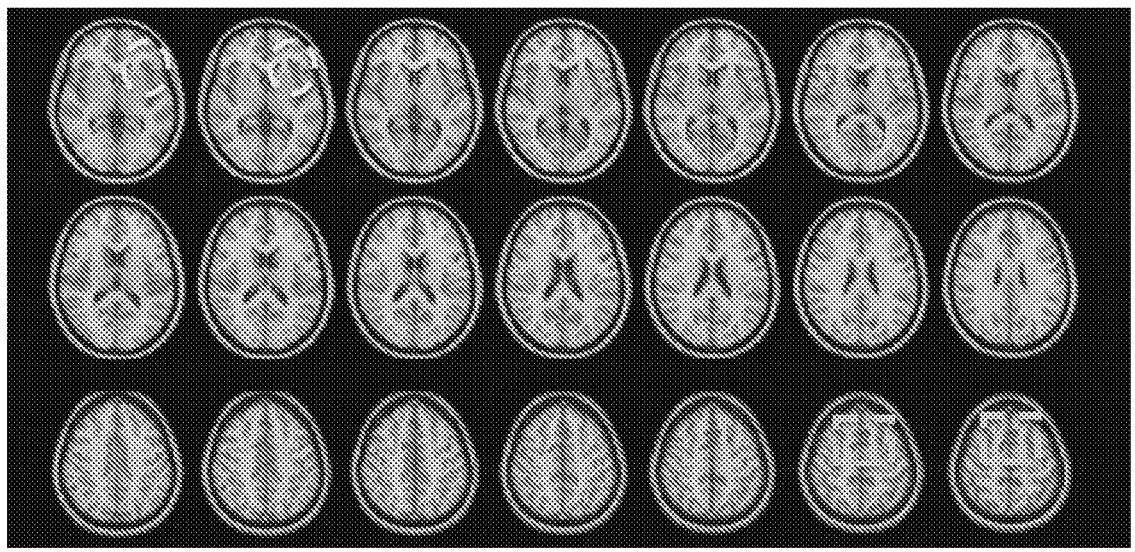
FIG. 4 shows areas of brain activity associated with a strong perceived urge to tic in a patient with Tourette's syndrome.

In another example study, a plurality of participants with TS were asked to indicate when they felt the urge to tic whilst undergoing an fMRI BOLD (blood oxygenation level dependent functional Magnetic Resonance Imaging) scan. The participants were asked to suppress the urge to tick throughout the scan. FIG. 4 shows a magnetic resonance image of the brain of each participant captured when the respective participant indicated that they felt the urge to tic. The brain areas that were monitored during the study included the contralateral primary motor cortex, bilateral supplementary motor area (SMA)/anterior cingulate cortex, right caudate nucleus, and bilateral insula cortex. FIG. 4 shows areas of increased brain activity including the primary and supplementary motor cortex regions.

Figure 5:
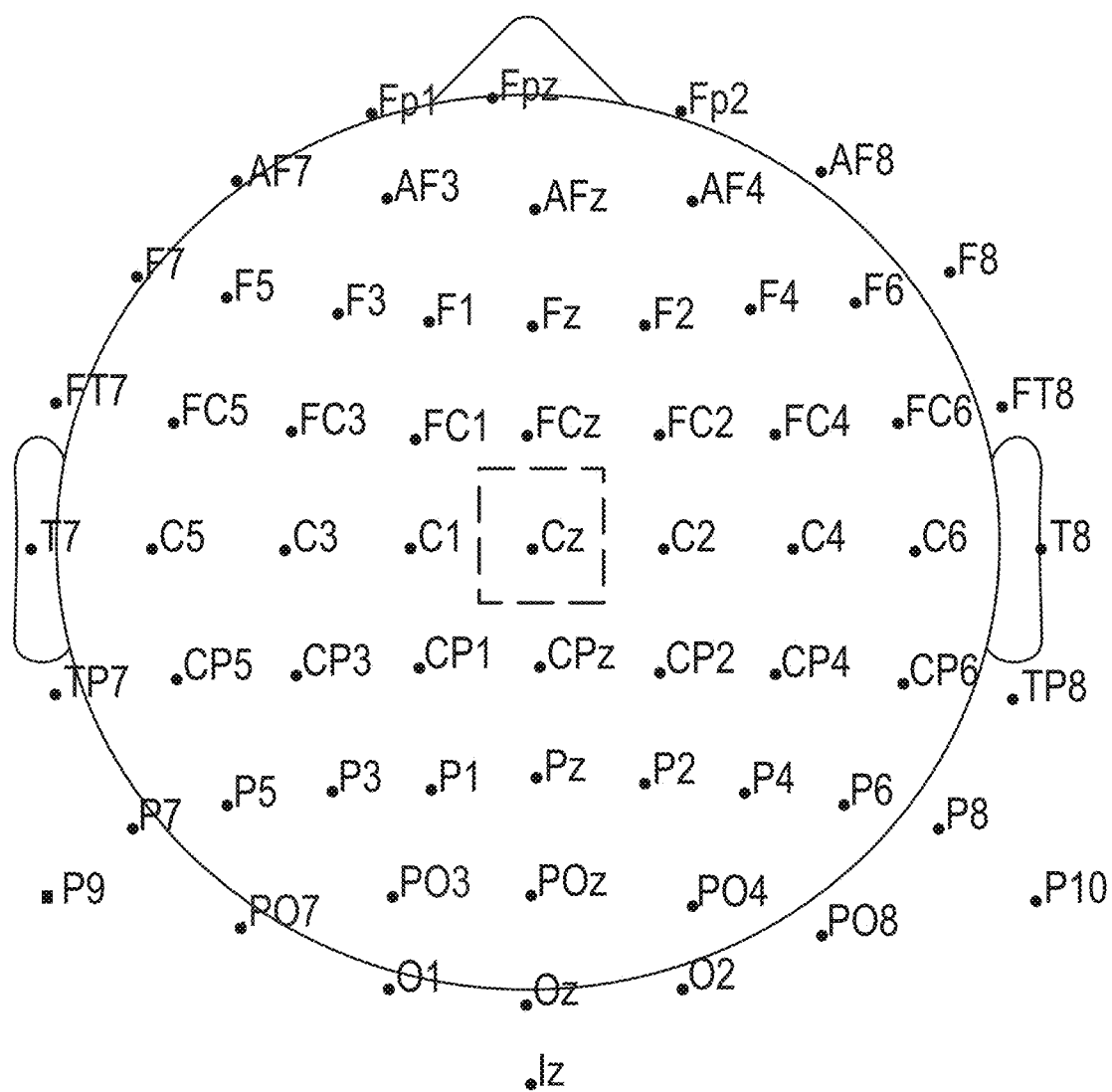
FIG. 5 shows the location of an array of electrodes, used to monitor brain activity using electroencephalography (EEG), with respect to a human scalp with one of the electrodes highlighted.
Figure 6:
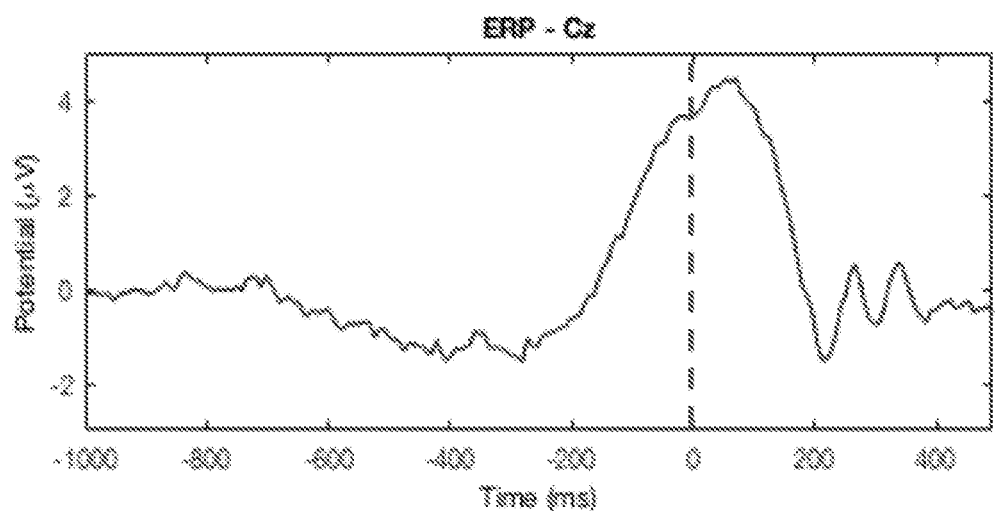
FIG. 6 shows event-related potential (ERP) over time obtained from neural oscillations recorded at the electrode highlighted in FIG. 5, with a volitional movement occurring at time=0.

FIG. 5 shows the location of 64 electrodes used to monitor a participant's brain activity using electroencephalography (EEG). Highlighted in FIG. 5 is one of these electrodes Cz. The electrode Cz is generally centred on the top of the participant's head and can be used to measure electrical signals linked to sensorimotor function. FIG. 6 shows a graph with event-related potential (ERP) shown on the y-axis and time shown on the x-axis. The ERP values were obtained from neural oscillations recorded at the electrode Cz over a time period extending from t=−1000 to t=500. At time=0, the participant completed a volitional movement.

Figure 7:
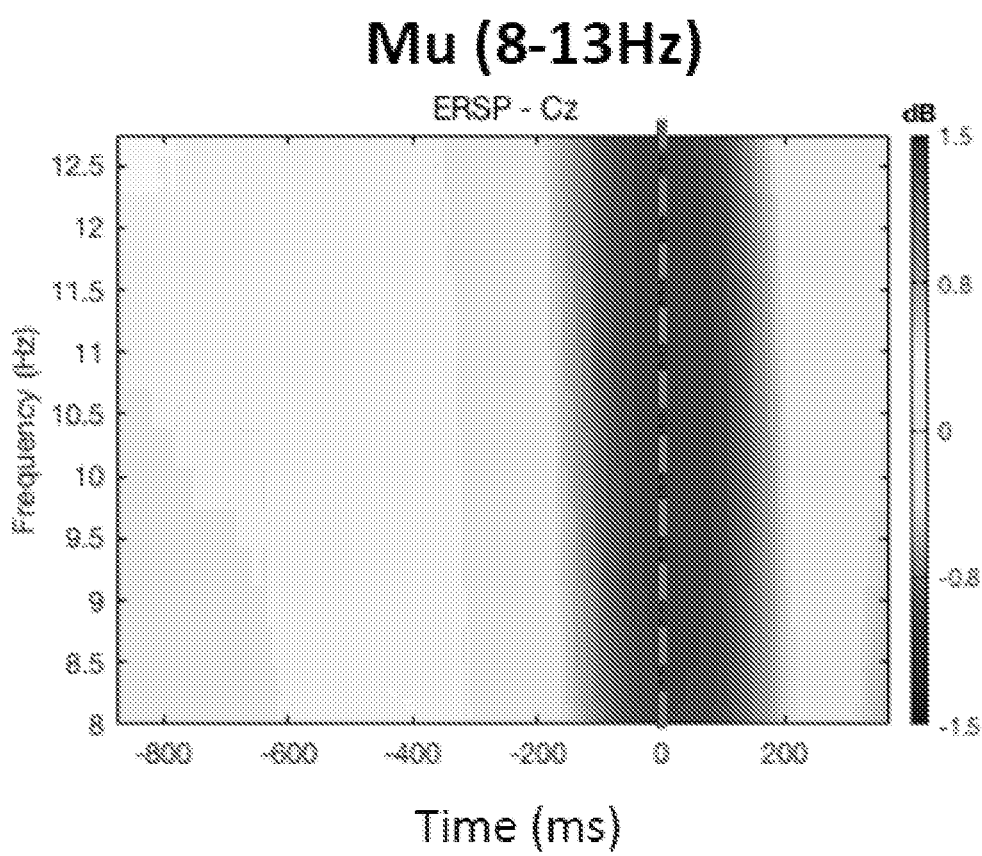
FIG. 7 shows a time-frequency analysis of ERSP obtained from Mu-band neural oscillations recorded at the electrode highlighted in FIG. 5 over the same time period as FIG. 6.
Figure 8:
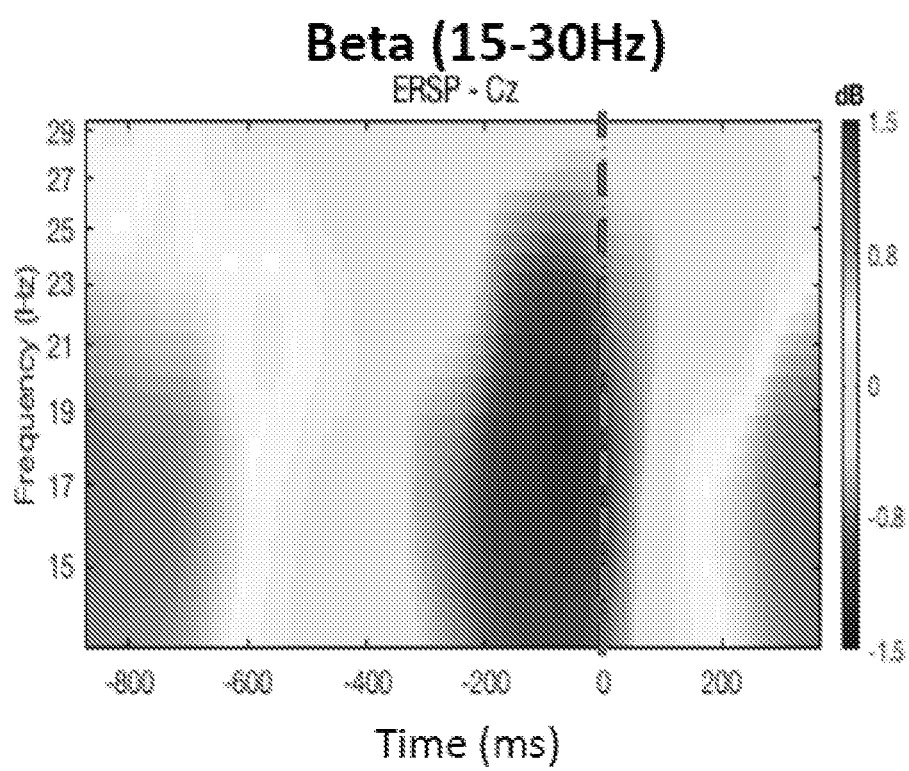
FIG. 8 shows a time-frequency analysis of ERSP obtained from Beta-band neural oscillations recorded at the electrode highlighted in FIG. 5 over the same time period as FIG. 6.

FIG. 7 shows a time-frequency analysis of ERSP obtained from Mu-band neural oscillations recorded at electrode Cz during the same time period, with the volitional movement occurring at t=0. Time is shown on the x-axis and frequency is shown in the y-axis. FIG. 8 shows a time-frequency analysis of ERSP obtained from Beta-band neural oscillations recorded at electrode Cz, during the same time period, with the volitional movement occurring at t=0.

Figure 9:
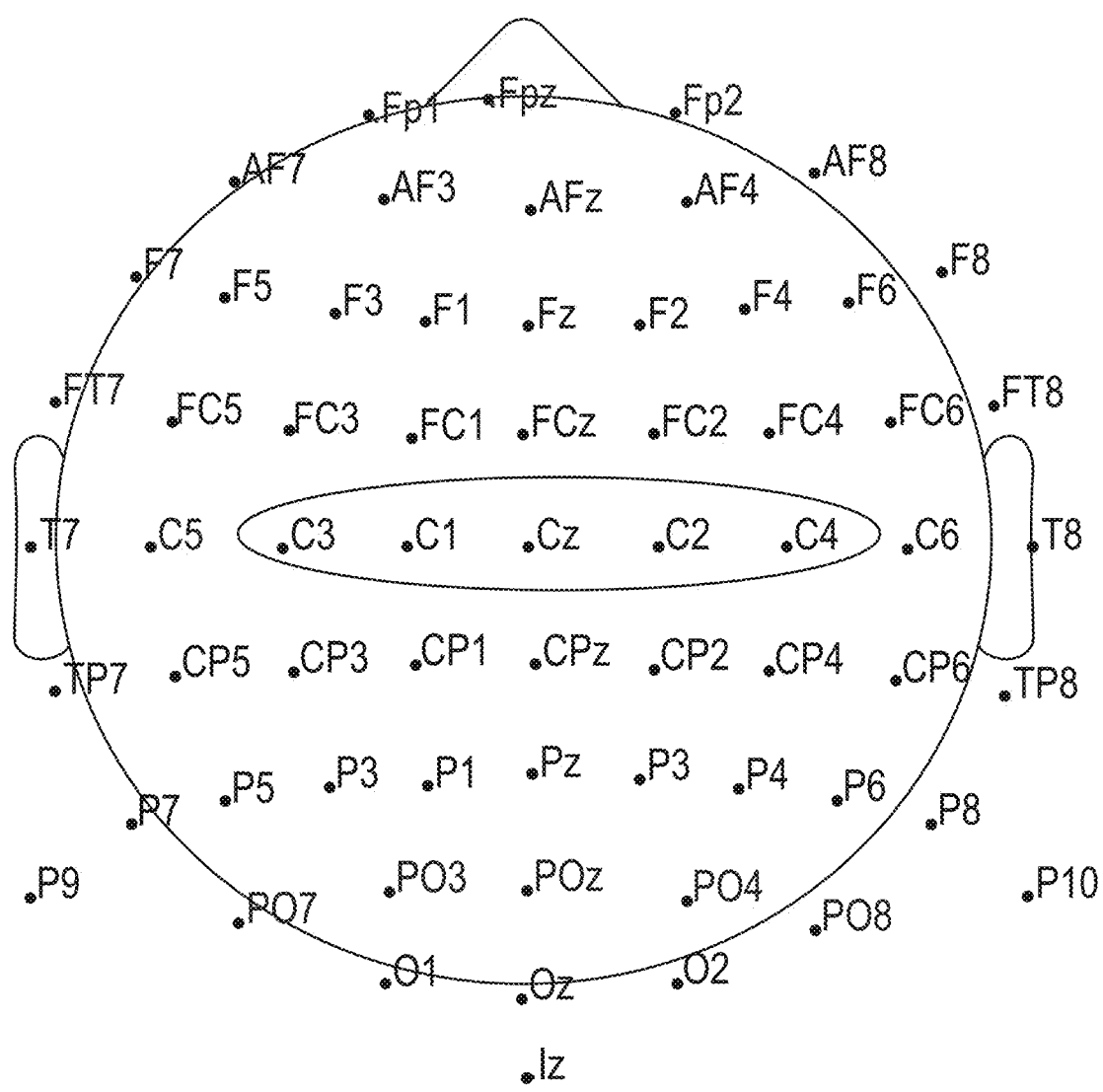
FIG. 9 shows the array of electrodes of FIG. 5 with a group of the electrodes highlighted.
Figure 10:
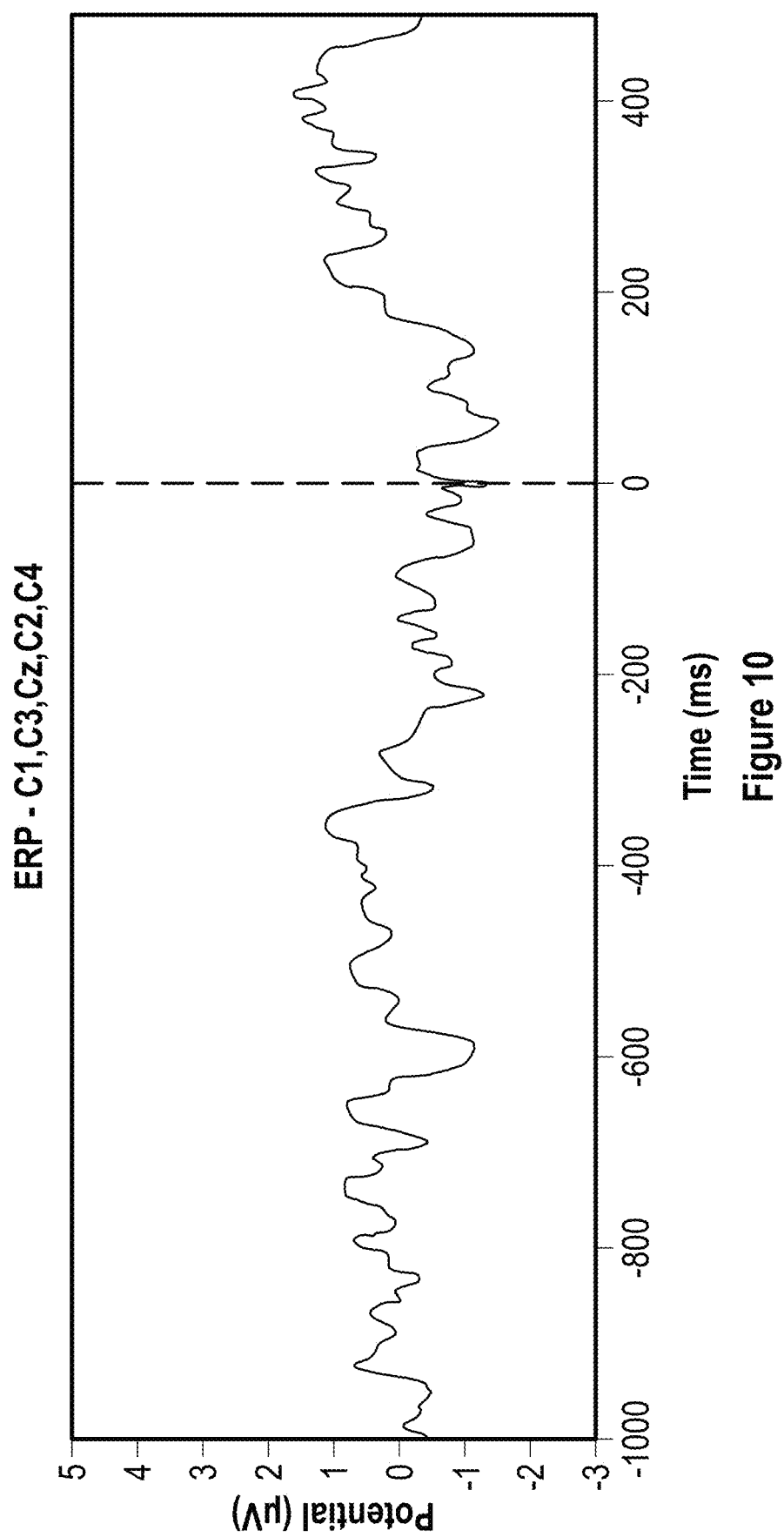
FIG. 10 shows ERP over time obtained from neural oscillations recorded at the electrodes highlighted in FIG. 9, with a tic occurring at time=0.
Figure 11:
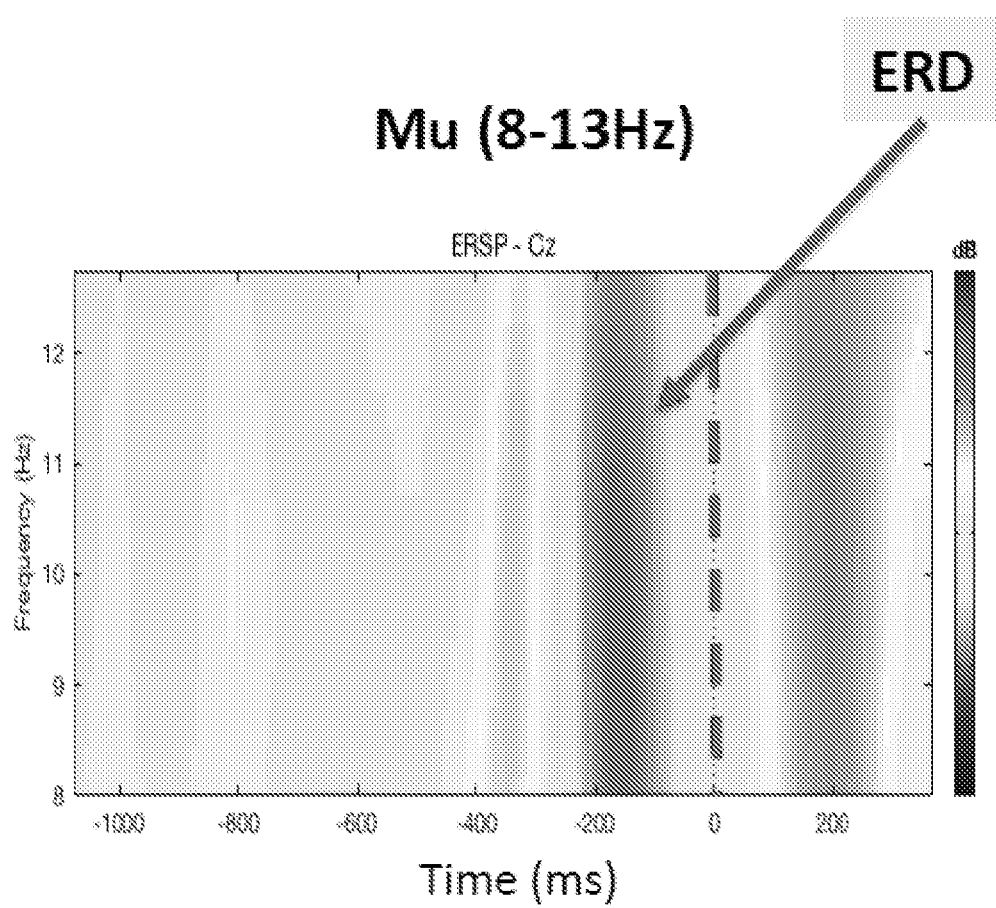
FIG. 11 shows a time-frequency analysis of ERSP obtained from Mu-band neural oscillations recorded at the electrode highlighted in FIG. 5 over the same time period as FIG. 10.
Figure 12:
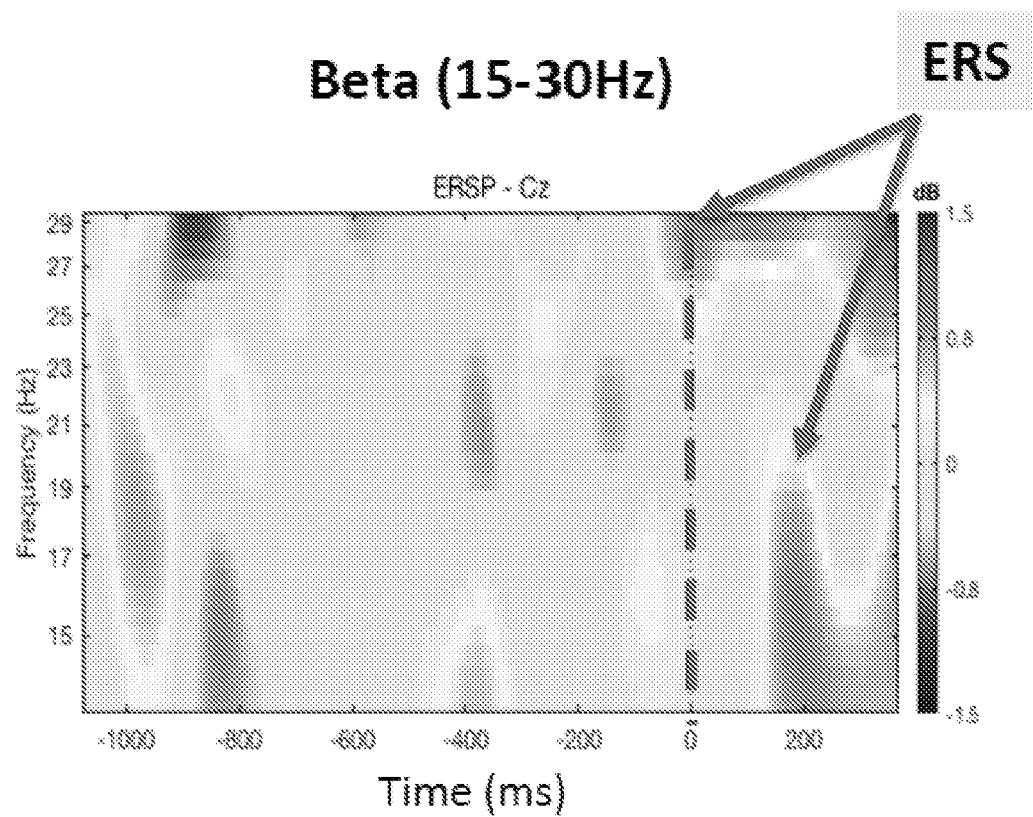
FIG. 12 shows a time-frequency analysis of ERSP obtained from Beta-band neural oscillations recorded at the electrode highlighted in FIG. 5 over the same time period as FIG. 10.

FIG. 9 shows the same 64 electrodes as shown in FIG. 5. Highlighted in FIG. 9 is a group of five of the electrodes C3, C1, Cz, C2, C4. FIG. 10 shows a graph FIG. 10 shows a graph with ERP shown on the y-axis and time shown on the x-axis. The ERP values of FIG. 10 were obtained from the average ERP obtained from neural oscillations measured at the electrodes C3, C1, Cz, C2, C4 over a time period extending from t=−1000 to t=500. At time=0, the participant experienced a tic. FIG. 11 shows a time-frequency analysis of ERSP of Mu-band neural oscillations recorded at electrode Cz during the same time period, with the tic occurring at time=0. FIG. 12 shows a time-frequency analysis of ERSP of Beta-band neural oscillations recorded at electrode Cz over the same time period, with the tic occurring at time=0. Labelled on FIG. 11 is a period of ERD preceding the tic, and labelled on FIG. 12 are two points of ERS immediately following the tic.

FIG. 6 shows an increase in ERP over the motor cortex, measured at electrode Cz, in the approximately 200 ms preceding the volitional movement. FIGS. 7 and 8 show ERD of Mu-band and Beta-band neural oscillations immediately preceding (by approximately 200 ms) the volitional movement, followed by a period of ERS of Beta-band neural oscillations within the approximately 300 ms following the onset of the volitional movement. In contrast, FIG. 10 shows no increase in ERP over the motor cortex during the approximately 200 ms preceding the tic. FIGS. 11 and 12 show ERD of Mu-band neural oscillations during the approximately 200 ms preceding the tic, and ERS of Beta-band neural oscillations at the onset of the tic and approximately 200 ms after tic onset.

Figure 13A:
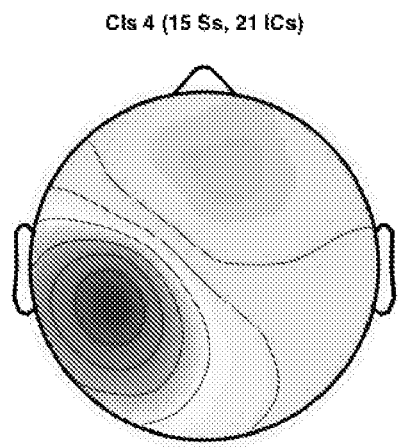
FIG. 13a shows scalp topography of ERP obtained from Mu-band neural oscillations recorded using the electrodes shown in FIGS. 5 and 9.
Figure 13B:
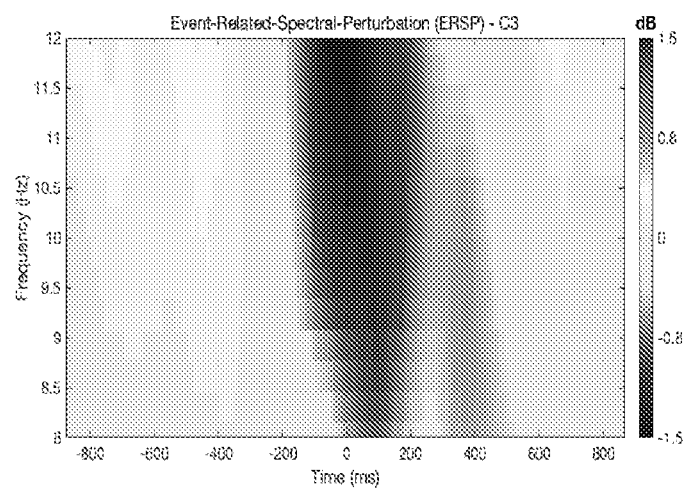
FIG. 13b shows a time-frequency analysis of ERSP obtained from Mu-band neural oscillations recorded at the electrode labelled C3 in FIGS. 5 and 9, with a tic occurring at time=0.
Figure 14:
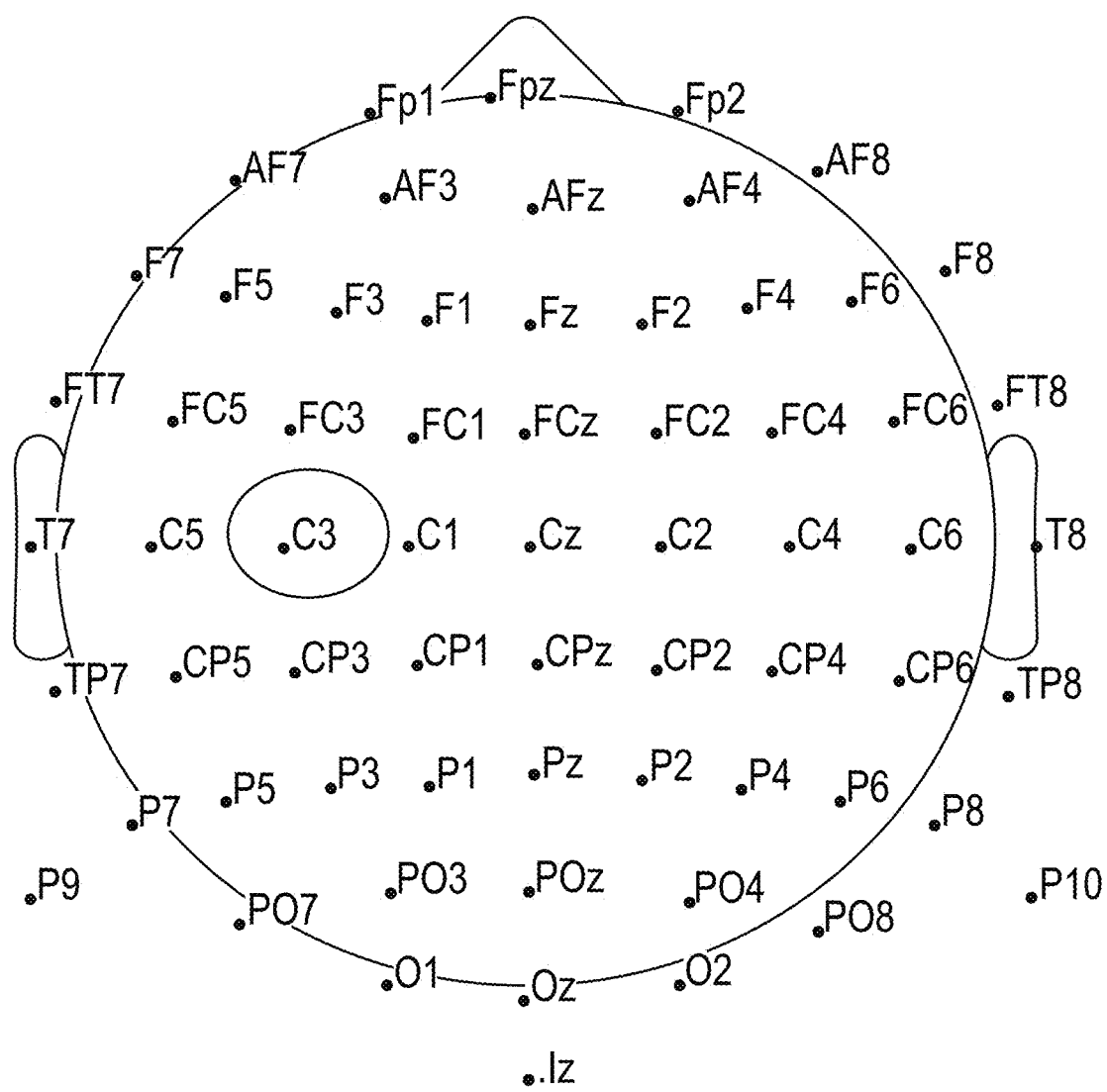
FIG. 14 shows the location of electrode C3.
Figure 15:
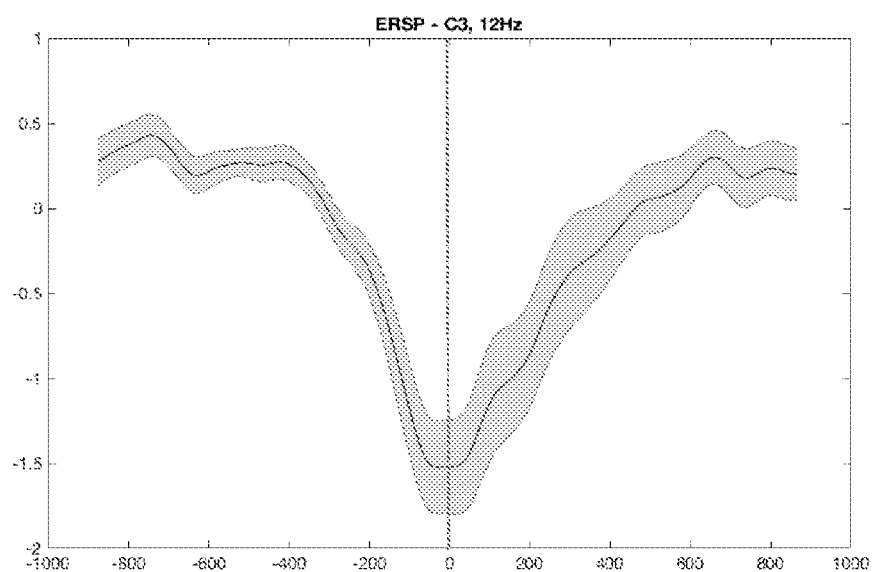
FIG. 15 shows ERSP obtained from 12 Hz neural oscillations recorded at electrode C3 over the same time period as FIG. 13b.

FIG. 13a shows scalp topography of the participant at the time of onset of a tic. The topography shows ERP obtained from Mu-band neural oscillations recorded using the electrodes shown in FIGS. 5 and 9. Darker areas indicate the location of greater ERP compared to other areas. FIG. 13a shows greater ERP at the location of electrode C3 (highlighted in FIG. 14 for clarity). FIG. 13b shows a time-frequency analysis of ERSP of Mu-band neural oscillations recorded at electrode C3 immediately before and after a tic (the tic occurring at time=0). FIG. 15 shows ERSP of 12 Hz neural oscillations observed immediately before and after the tic (the tic occurring at time=0). FIGS. 13a-b and 15 show increased ERSP of Mu-band neural oscillations during stable posture (i.e. not moving) preceding a tic, followed by decreased ERSP and increased ERP of Mu-band neural oscillations during tic movement. This suggests desynchronisation of Mu-band neural oscillations during a tic. The decrease in ERSP of Mu-band neural oscillations is associated with increased cortical excitability.

Figure 16:
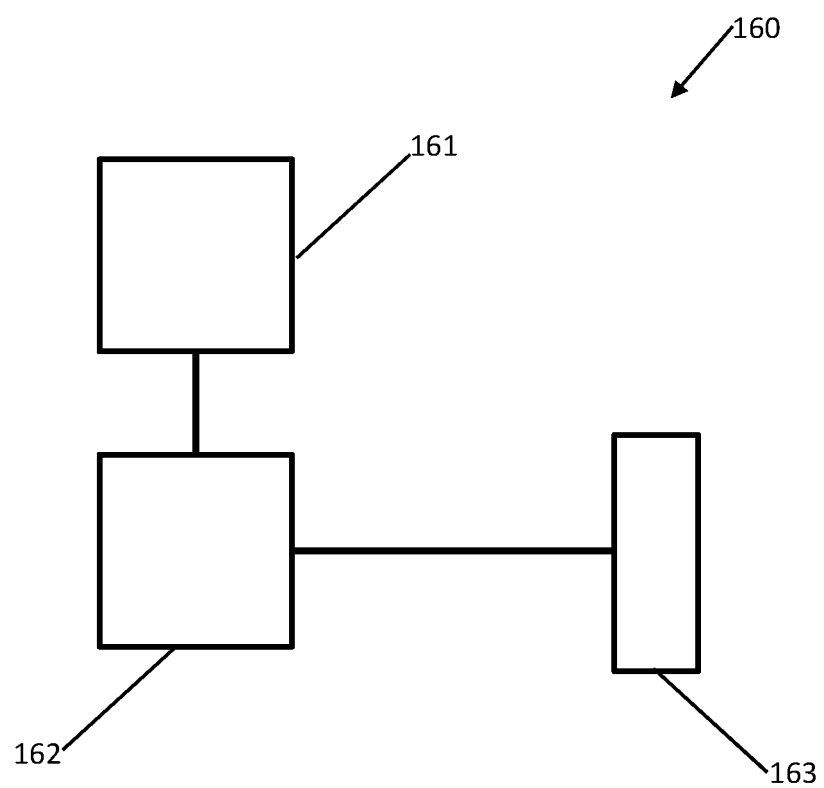
FIG. 16 shows a schematic representation of an electrical nerve stimulator according to an embodiment of the invention.

FIG. 16 shows an electrical nerve stimulator 160 according to an embodiment of the invention. The electrical nerve stimulator 160 comprises a power source 161, a controller 162 and an electrode 163. The power source 161 is configured to deliver electrical power to the electrode 163. The controller 162 is configured to control the delivery of electrical power from the power source 161 to the electrode 163. The electrode 163 is configured to deliver electrical stimulation to a user.

In some embodiments, the electrode 163 may be attachable to a wrist of the user. For example, the electrical nerve stimulator 160 may comprise a wrist strap for attaching the electrical nerve stimulator 160 to a wrist of a user. The wrist strap may be releasable. In other embodiments, the electrical nerve stimulator 160 may be configured to stimulate a trigeminal nerve of a user. Where the electrical nerve stimulator 160 is attachable to a wrist of a user, the electrode 163 may be configured to deliver electrical stimulation to a median nerve of the user. In some embodiments, the electrode 163 may comprise a bar electrode. A conducting part of the electrode may comprise stainless steel. The electrode 163 may comprise a first part and a second part separate from the first part. The first part and the second part may be arranged such that a maximum distance between first part and the second part is within a range of 10-50 mm or 20-40 mm. A maximum distance between first part and the second part may be 30 mm. One or both of the first part and the second part may comprise a disc. One or both of the first part and the second part may comprise a diameter within a range of 4-12 mm or 6-10 mm. One or both of the first part and the second part may comprise a diameter of 8 mm. The electrode 163 may comprise an anode and a cathode. Where the electrode 163 comprises a first part and a second part, the first part may comprise an anode and the second part may comprise a cathode. The anode and the cathode may be arranged such that when the electrode 163 is attached to a wrist of the user, the anode is located between the cathode and the hand of the user associated with the wrist.

In some embodiments, the power source 161 may comprise a portable power source, such as a battery. The power source 161 and the controller 162 may be packaged together. The controller 162 may be configured to deliver an electrical pulse to the electrode 163 comprising a duration, or pulse width, up to 0.2 ms. The controller 162 may be configured to deliver an electrical pulse to the electrode 163 comprising a square wave electrical pulse. The controller 162 may be configured to deliver an electrical pulse to the electrode 163 comprising an amplitude within a range of 0.5-1.5 mA. The controller 162 may be configured to deliver an electrical pulse to the electrode 163 comprising an amplitude of 1 mA. The controller 162 may be configured to deliver a sequence of electrical pulses, i.e. an electrical signal, to the electrode 163 at a frequency within a range of 8-12 Hz to entrain Mu-band neural oscillations of the brain of a user. The controller 162 may be configured to deliver a sequence of electrical pulses to the electrode 163 at a frequency of 12 Hz to entrain Mu-band neural oscillations of the brain of a user. The controller 162 may be configured to deliver a sequence of electrical pulses to the electrode 163 at a frequency within a range of 13-30 Hz to entrain Beta-band neural oscillations of the brain of a user. The controller 162 may be configured to deliver a sequence of electrical pulses to the electrode 163 at a frequency of 19 Hz to entrain Beta-band neural oscillations of the brain of a user.

In an example study, an electrical nerve stimulator according to an embodiment of the invention was used to deliver a plurality of electrical square wave pulses, or 'trains' of electrical square wave pulses, to each of a plurality of participants of the study. In the example study, the controller of the electrical nerve stimulator comprised a Digitimer DS7A HV Current Stimulator (available from Digitimer Ltd, Hertfordshire, UK). In other example implementations of the electrical nerve stimulator, any suitable controller may be used. The electrode of the electrical nerve stimulator comprised a bar electrode comprising two stainless steel disk electrodes, comprising an anode and a cathode, with a diameter of 8 mm separated by 30 mm. Following the application of conductive gel, the anode was placed most proximal to the hand and the cathode was placed most proximal to the arm.

Figure 17:
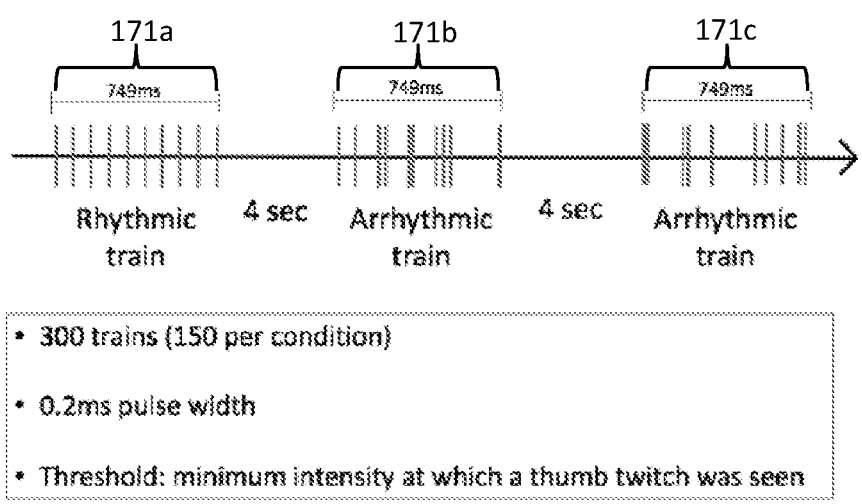
FIG. 17 shows three groups, or 'trains', of electrical pulses delivered to each of a plurality of participants of a first study.

In the example study, 300 trains were delivered to the median nerve at the right-hand wrist of each participant. FIG. 17 shows a schematic illustration of three of the trains 171a-c. Stimulation of the median nerve through the delivery of electrical pulses is referred to herein as Median Nerve Stimulation (MNS). A four second break was provided between delivering each train, and an extended break was provided every 75 trains. Each electrical pulse, indicated in FIG. 17 by the vertical lines intersecting the horizontal arrow at right angles, lasted 0.2 ms, i.e. had a pulse width of 0.2 ms, and was delivered with the minimum intensity required to generate a thumb twitch in each participant. Each pulse train comprised 10 individual pulses delivered within a window of 749 ms, and was either rhythmic (with 83 ms between each pulse, i.e. a frequency of 12 Hz) or arrhythmic (i.e. with non-uniform intervals between each pulse). 150 rhythmic pulse trains and 150 arrhythmic pulse trains were delivered, the order of rhythmic and arrhythmic pulses being random. The pulses were delivered at an amplitude of 1 mA. The frequency of rhythmic stimulation (12 Hz) was selected from the same frequency range as Mu-band neural oscillations to determine if the stimulation could be used to entrain with Mu-band neural oscillations.

EEG data was recorded using the same 64 electrodes shown in FIGS. 5 and 9 with an initial sampling rate of 1024 Hz, later down-sampled to 128 Hz. The impedance of the electrodes was kept under 30 μV in all participants. Reference electrodes were placed on the left and right mastoids. Bipolar vertical and horizontal electrooculography (EOG) electrodes were also used to record data.

The EEG data was low-pass filtered at 45 Hz and high-pass filtered at 1 Hz. Channels (i.e. data from individual electrodes) showing aberrant behaviour were deleted and noisy channels were interpolated. No more than 3 channels were deleted from participants. Automatic Artefact Removal (AAR) was used to remove EOG artefacts using recursive least squares regression. Time-windows of −1 to 3 seconds, time-locked to the first pulse of the train were extracted. The whole second before the start of the stimulation was used as baseline. Epochs showing abnormal trends or excessive noise were rejected: those epochs showing a signal amplitude at +−100 μV in one or more channels were rejected; those epochs with signal slopes exceeding a threshold of 50 μV in one or more channels were rejected; those epochs with 5 times the standard deviation in the probability distribution were rejected; and those epochs which their kurtosis statistic was larger than 5 times of the standard deviation of the data were rejected. The average number of epochs between participants was 125 in the rhythmic condition (i.e. in response to the rhythmic pulses) and 123 in the arrhythmic condition (i.e. in response to the arrhythmic pulses). Artefacts were detected by running Independent Component Analysis (ICA) and components were rejected with the use of Multiple Artefact Rejection Algorithm (MARA) and visual inspection.

Mu-band neural oscillations obtained from the EEG data were plotted for every pulse of stimulation from data low-pass filtered at 13 Hz and high-pass filtered at 8 Hz. Scalp maps were plotted using whole scalp electrodes. Scalps were plotted using the 5 electrodes situated over the left motor cortex (FC1, FC3, C1, C3, CP3 as shown in FIGS. 5 and 9).

Figure 18:
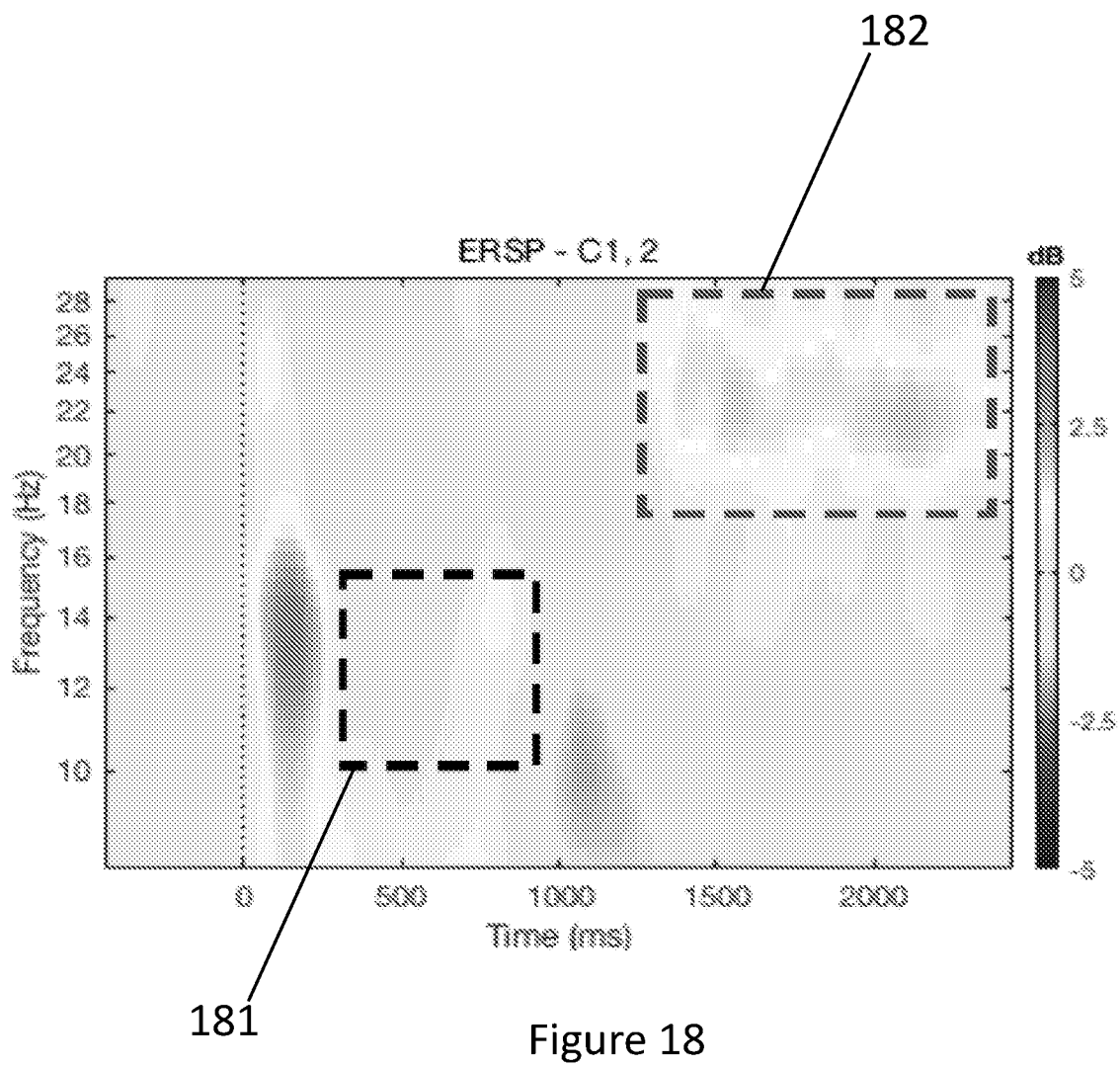
FIG. 18 shows a time-frequency analysis of average ERSP obtained from neural oscillations of each participant of the first study recorded at electrode C1 before, during and after delivery of an arrhythmic pulse train.

FIG. 18 shows a time-frequency analysis of average ERSP obtained from neural oscillations of each participant of the study recorded at electrode C1 (as shown in FIGS. 5 and 9) before, during and after delivery of an arrhythmic pulse train. Time is shown on the x-axis and frequency is shown on the y-axis. The colouring of the graph shows ERSP according to the scale shown to the right of the graph. Time=0 represents the onset of the arrhythmic pulse train. The graph shows an increase in ERSP in the 10-15 Hz frequency range of neural oscillations during an initial period of time following the onset of delivery of the arrhythmic pulse train. However, this increase in ERSP was not sustained following this initial period of time, as shown by the area of the graph labelled 181. By contrast, there is an increase in ERSP of neural oscillations in the 20-26 Hz range, indicated by 182, during a period of time after delivery of the arrhythmic pulse train (i.e. after 749 ms).

Figure 19:
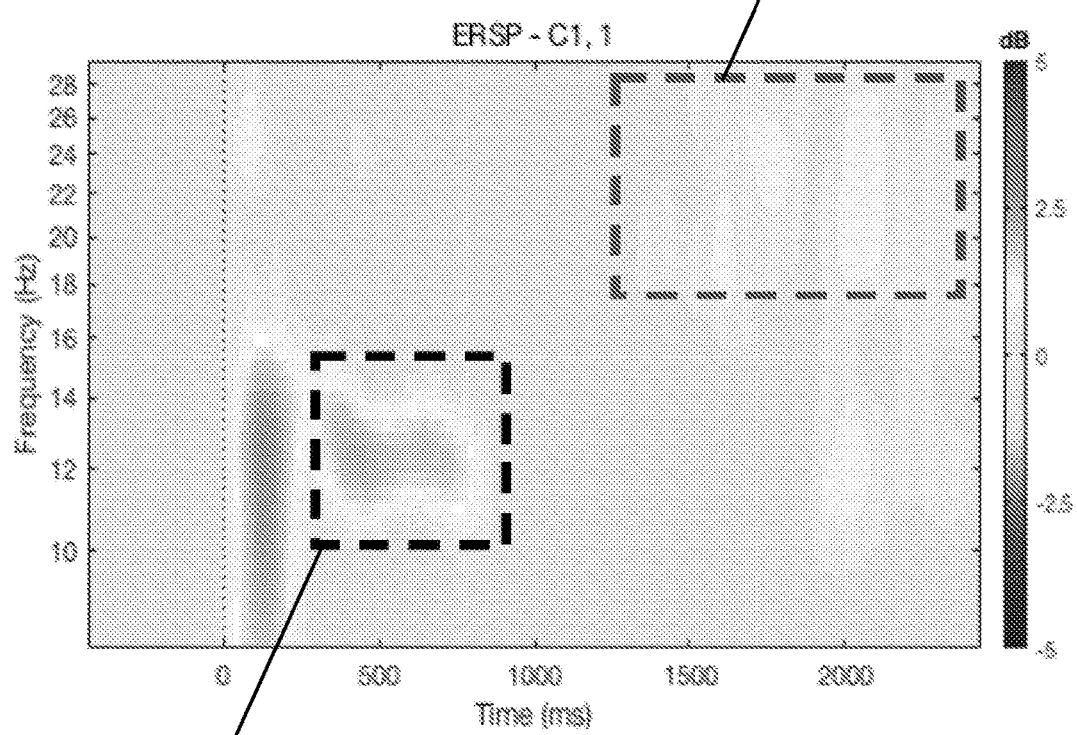
FIG. 19 shows a time-frequency analysis of average ERSP obtained from neural oscillations of each participant of the first study recorded at electrode C1 before, during and after delivery of a rhythmic pulse train.

FIG. 19 shows a time-frequency analysis of average ERSP obtained from neural oscillations of each participant of the study recorded at electrode C1 (as shown in FIGS. 5 and 9) before, during and after delivery of a rhythmic pulse train. Time is shown on the x-axis and frequency is shown on the y-axis. The colouring of the graph shows ERSP according to the scale shown to the right of the graph. Time=0 represents the onset of the rhythmic pulse train. The area of the graph labelled 191 shows an increase in ERSP for neural oscillations at 12 Hz frequency during a period of time extending from 250 ms to 900 ms. By contrast, an increase in ERSP in the 20-26 Hz range, indicated by 192, after delivery of the rhythmic pulse train (i.e. after 749 ms) is absent.

Figure 20A:
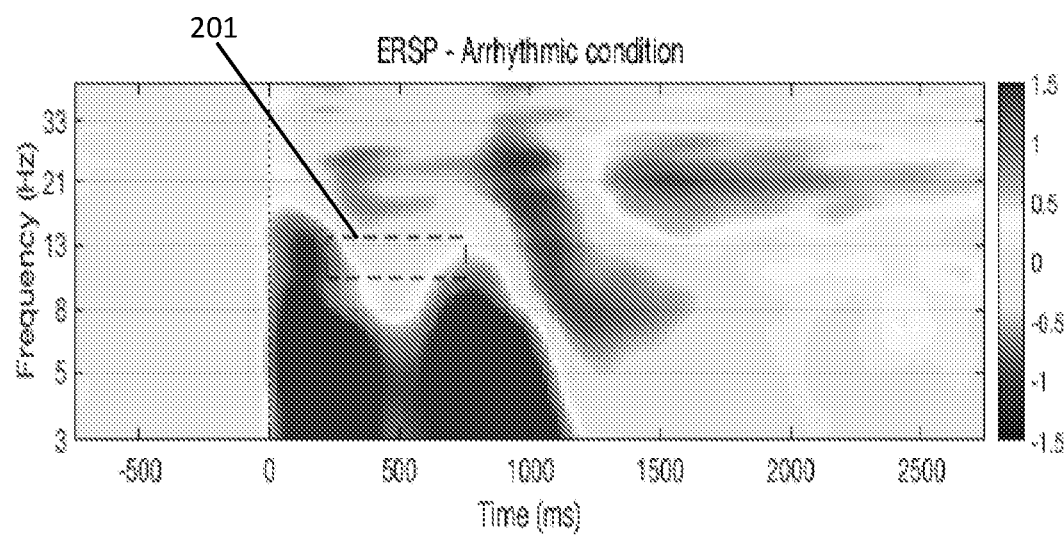
FIG. 20a shows the results of FIG. 18 at a higher resolution of ERSP.
Figure 20B:
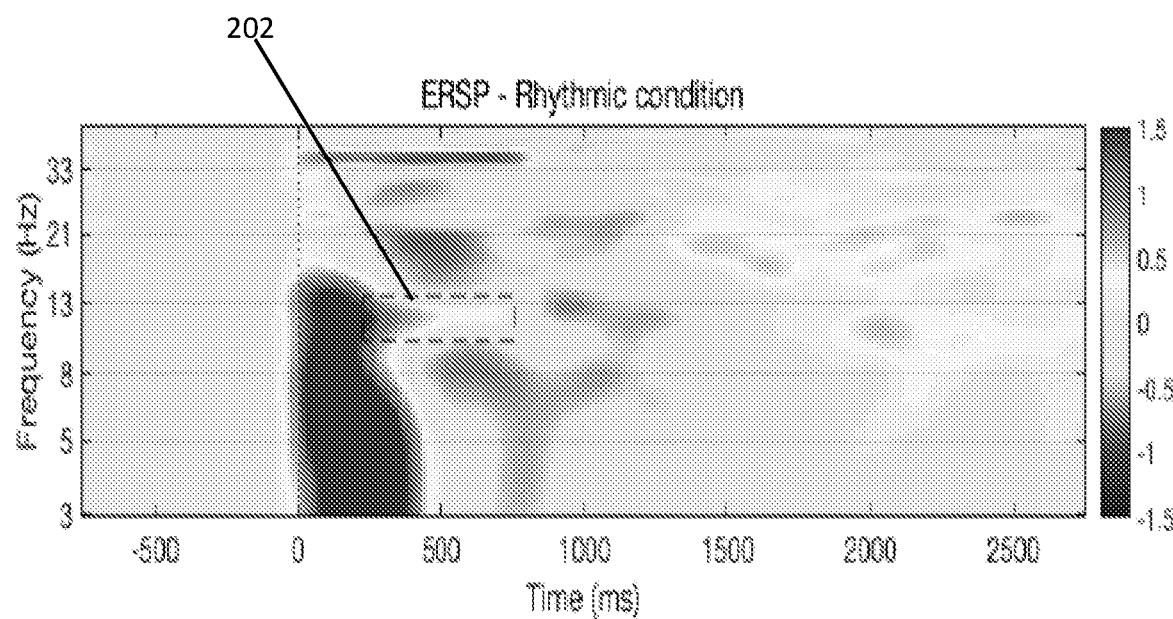
FIG. 20b shows the results of FIG. 19 at a higher resolution of ERSP.
Figure 20C:
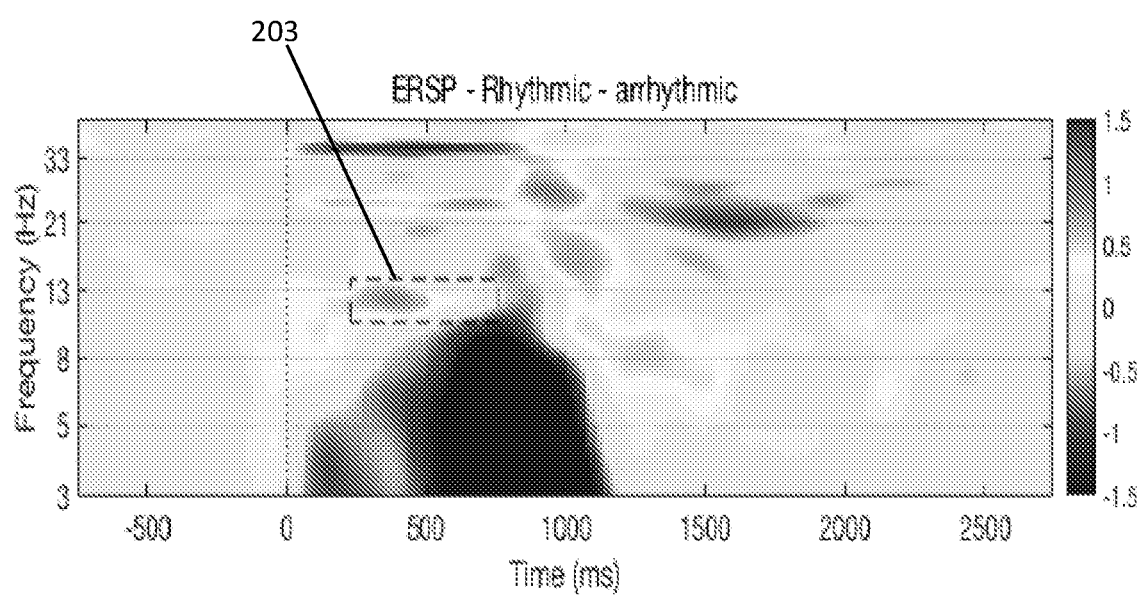
FIG. 20c shows the ERSP values of FIG. 20a subtracted from the ERSP values of FIG. 20b across the same time and frequency range.

FIG. 20a shows the results of FIG. 18 at a higher resolution of ERSP, and FIG. 20b shows the results of FIG. 19 at a higher resolution of ERSP. FIG. 20c shows the ERSP values of FIG. 20a subtracted from the ERSP values of FIG. 20b across the same time and frequency range. These results show an increase in ERSP in the initial 1-3 pulses (0-249 ms) of both an arrhythmic pulse train (FIG. 20a) and a rhythmic pulse train (FIG. 20b) for different neural oscillation frequency bands, including Theta-band (4-7 Hz), and Mu- and Beta-bands. This is represented by the darker areas of the FIGS. 20a and 20b extending from t=0. During pulses 4-10 (250-832 ms), an increase in ERSP of Mu-band neural oscillations is shown in the rhythmic pulse train in a narrow frequency band that peaks at the frequency of the stimulation, i.e. 12 Hz (illustrated by area 202). This increase in ERSP is significant ($p<0.05^{FDR\text{-}corrected}$) relative to the ERSP obtained for the same time period during the arrhythmic pulse train, as shown by areas 201 and 203 in FIGS. 20a and 20c respectively.

Figure 21:
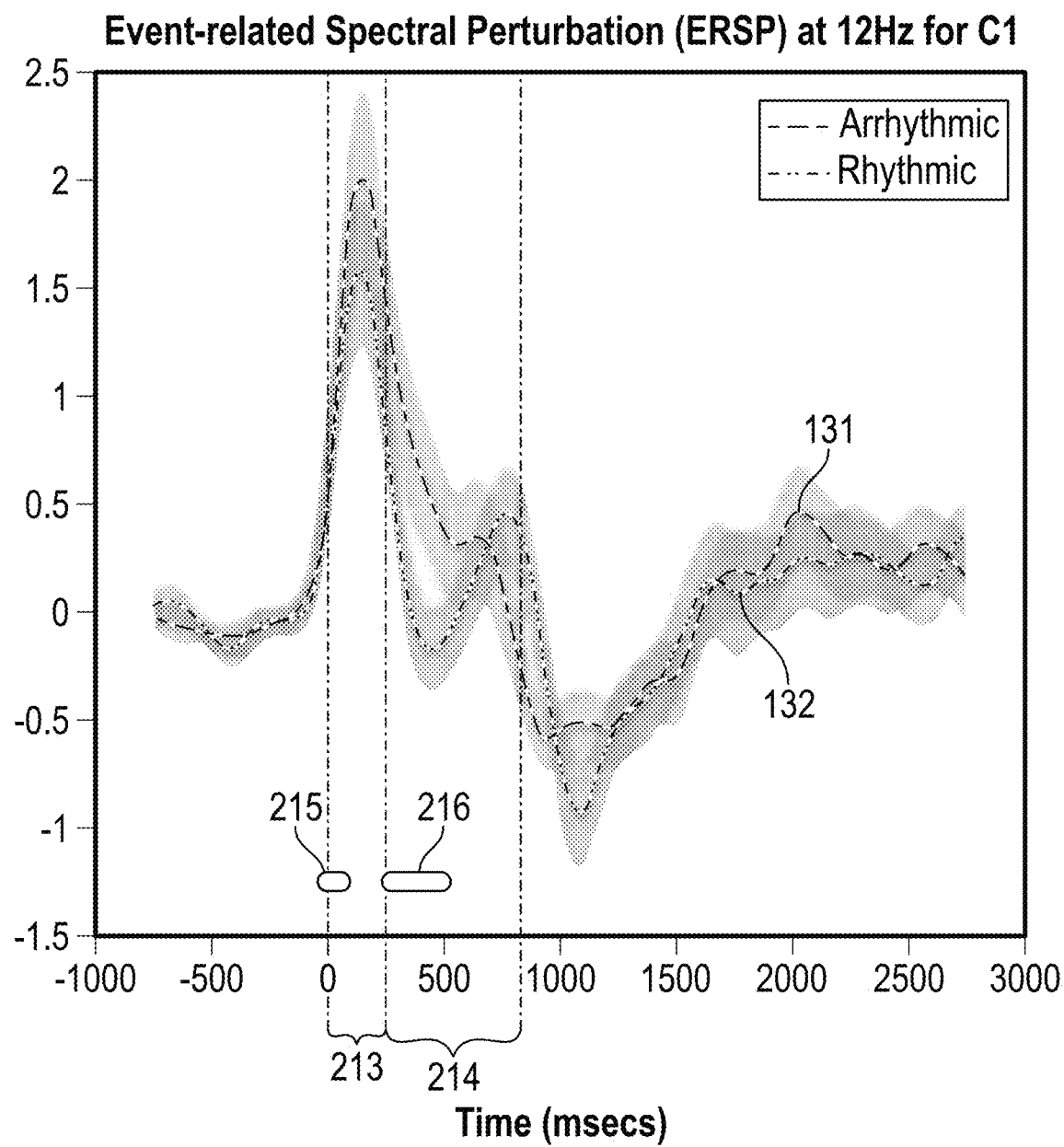
FIG. 21 shows average ERSP, obtained from 12 Hz neural oscillations of each participant of the first study recorded at electrode C1, against time before, during and after delivery of a rhythmic pulse train and before, during and after delivery of an arrhythmic pulse train.

FIG. 21 shows average ERSP obtained from 12 Hz neural oscillations of each participant of the study recorded at electrode C1 against time before, during and after delivery of a rhythmic pulse train (line 131) and before, during and after delivery of an arrhythmic pulse train (line 132). Time is shown on the x-axis and ERSP is shown on the y-axis. Time=0 represents the onset of the respective pulse train. The area labelled 213 indicates the initial 1-3 pulses of the respective pulse train and the area labelled 214 indicates pulses 4-10 of the respective pulse train. The bars labelled 215 and 216 indicate periods of time during which the difference between ERSP for the rhythmic pulse train and the arrhythmic pulse train was statistically significant. FIG. 21 shows a significantly greater average ERSP of 12 Hz neural oscillations during rhythmic stimulation compared to during arrhythmic stimulation.

Figure 22A:
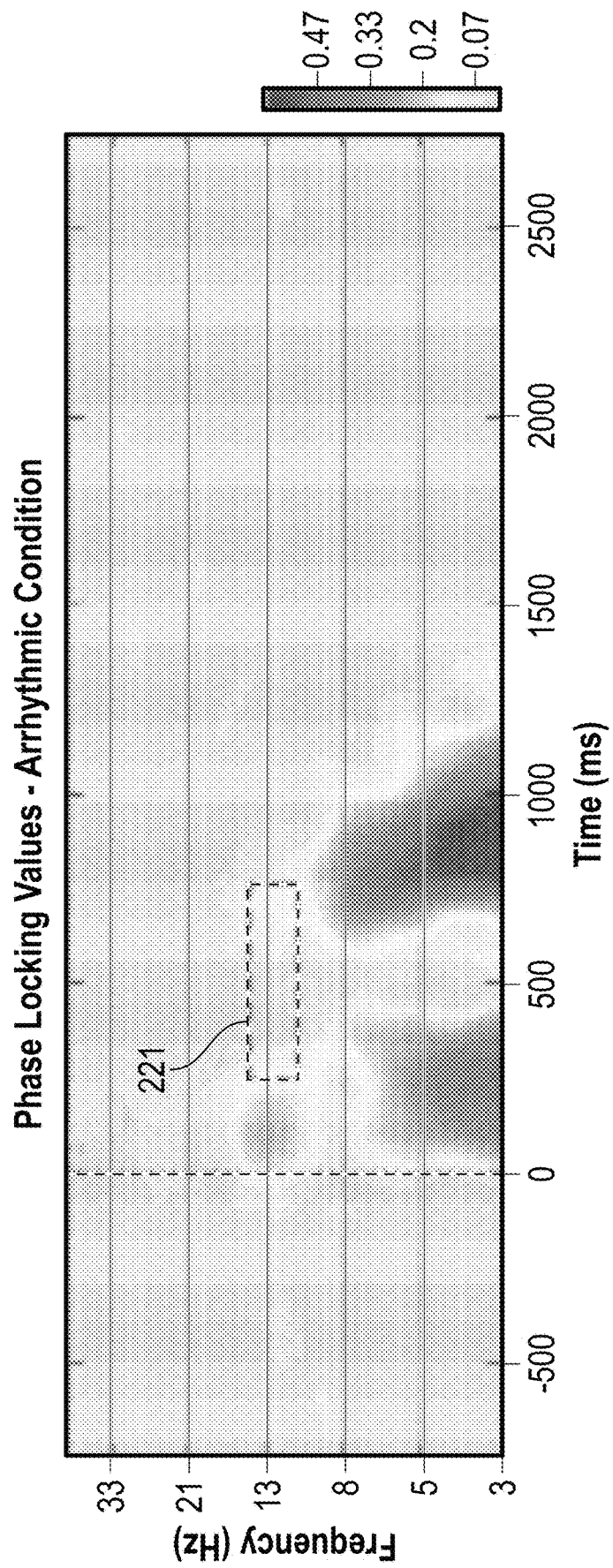
FIG. 22a shows a time-frequency analysis of phase locking values (PLV) obtained from neural oscillations of each participant of the first study recorded at electrode C1 before, during and after delivery of an arrhythmic pulse train.
Figure 22C:
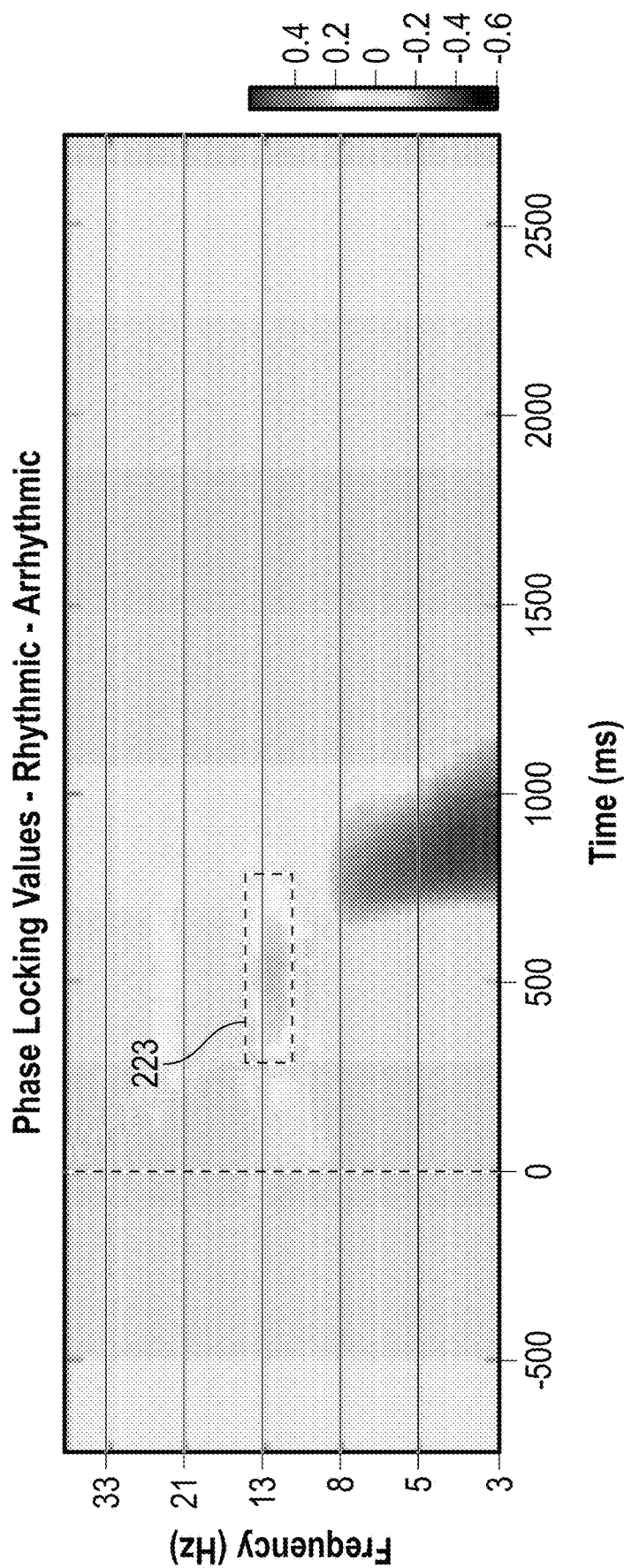
FIG. 22c shows PLV of FIG. 22a subtracted from PLV of FIG. 22b across the same time and frequency range.

FIG. 22a shows a time-frequency analysis of phase locking values (PLV) obtained from neural oscillations of each participant of the study recorded at electrode C1 (as shown in FIGS. 5 and 9) before, during and after delivery of an arrhythmic pulse train. FIG. 22*b* shows a time-frequency analysis of phase locking values (PLV) obtained from neural oscillations of each participant of the study recorded at electrode C1 (as shown in FIGS. 5 and 9) before, during and after delivery of a rhythmic pulse train. Time is shown on the x-axis and frequency is shown on the y-axis in each of FIGS. 22*a* and 22*b*. The colouring of the graphs shows PLV according to the scale shown. Time=0 represents the onset of respective pulse train. FIG. 22*c* shows the PLV values of FIG. 22*a* subtracted from the PLV values of FIG. 22*b* across the same time and frequency range.

PLV is a measure of inter-trial coherence (ITC). PLV quantifies the consistency in which oscillations fluctuate at the same phase and rhythm across trials and is used as a measure of phase alignment or phase synchrony. High PLV values correspond to high consistency.

As shown in FIGS. 22*a*-*c*, an increase in PLV was observed during the initial 1-3 pulses of both the arrhythmic and rhythmic trains, and an increase in PLV was observed during pulses 4-10 of the rhythmic train (shown by area 222 in FIG. 22*b*) which was absent in the arrhythmic train (shown by area 221 in FIG. 22*a*). This is further demonstrated by FIG. 22*c* (shown by area 223), and is consistent with the results of FIGS. 19*a*-*c*. These results show evidence of entrainment after the first 3 pulses of the train.

Figure 23:
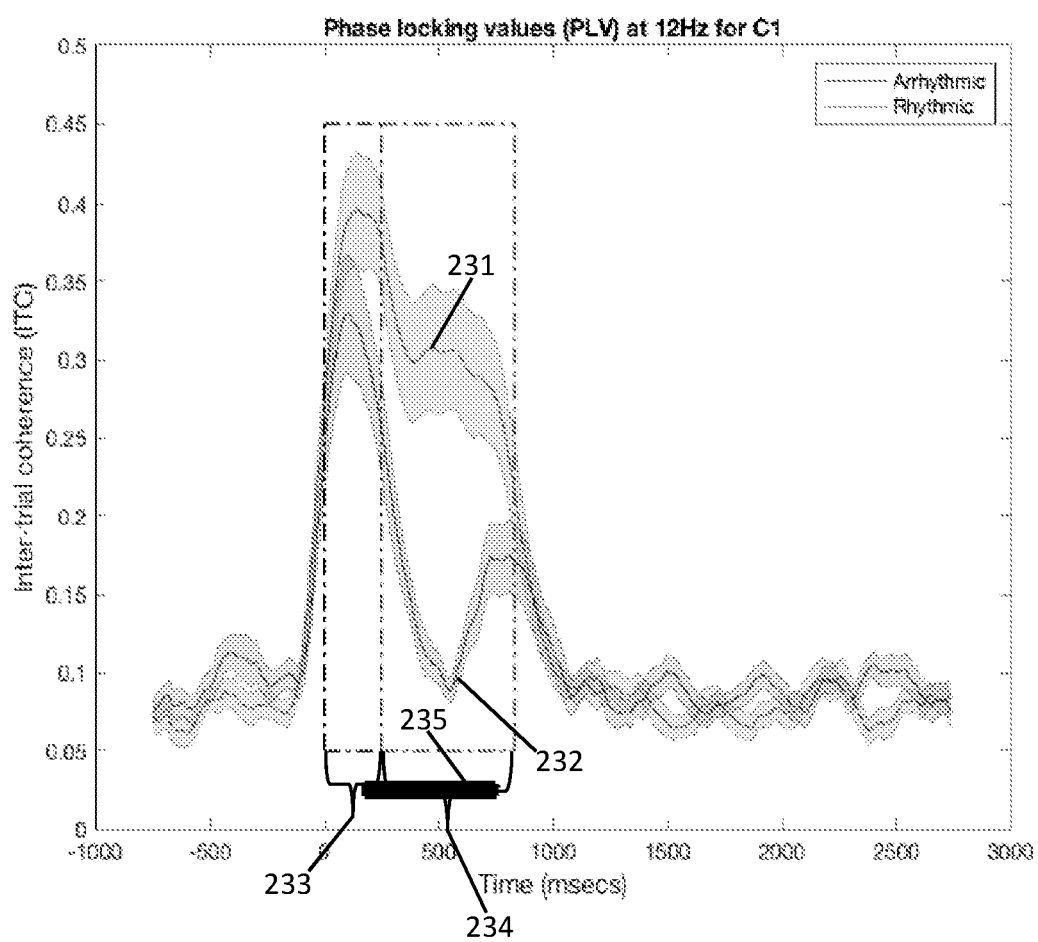
FIG. 23 shows PLV, obtained from 12 Hz neural oscillations of each participant of the first study recorded at electrode C1, against time before, during and after delivery of a rhythmic pulse train and before, during and after delivery of an arrhythmic pulse train.

FIG. 23 shows PLV across each participant of the study, obtained from 12 Hz neural oscillations recorded at electrode C1, against time before, during and after delivery of a rhythmic pulse train (line 231) and before, during and after delivery of an arrhythmic pulse train (line 232). Time is shown on the x-axis and PLV is shown on the y-axis. Time=0 represents the onset of the respective pulse train. The area labelled 233 indicates the initial 1-3 pulses of the respective pulse train and the area labelled 234 indicates pulses 4-10 of the respective pulse train. The bar labelled 235 indicates a period of time during which the difference between PLV for the rhythmic pulse train and the arrhythmic pulse train was statistically significant. FIG. 23 shows a significant difference in PLV between the arrhythmic and rhythmic trains during pulses 1-3 and pulses 4-10.

Figure 24:
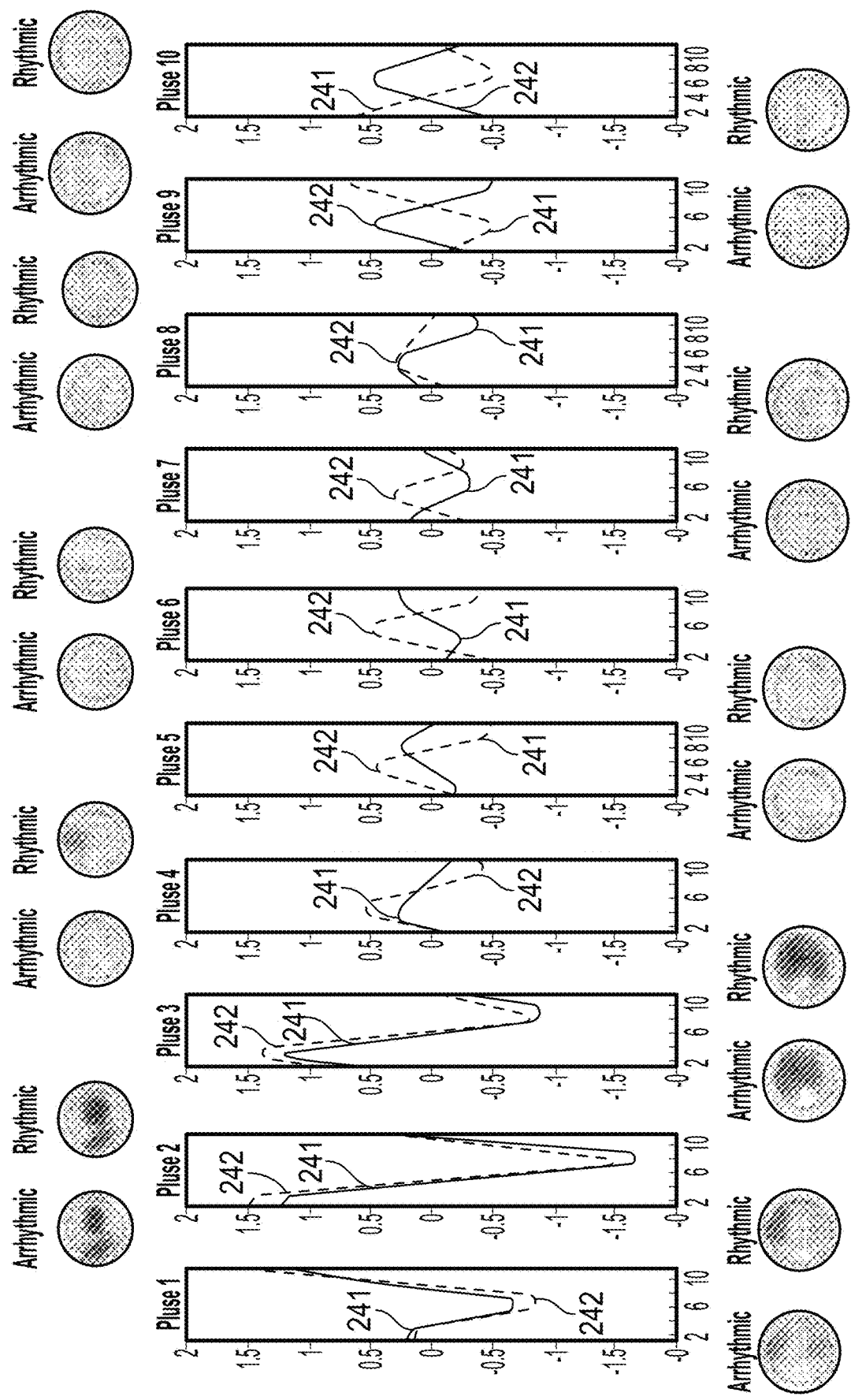
FIG. 24 shows a plot of 12 Hz neural oscillations of each participant of the first study recorded during each of the 10 pulses of both an arrhythmic train and a rhythmic train.

FIG. 24 shows a plot of average neural oscillations at 12 Hz recorded across the participants during each of the 10 pulses of both an arrhythmic train (line 241) and a rhythmic train (line 242). FIG. 24 suggests that stimulation during a rhythmic train leads to the re-setting of the phase occurring after every pulse of the train. This phase-reset is only seen for the first 3 pulses in an arrhythmic train.

FIGS. 18 to 24 demonstrate that the application of rhythmic electrical signals at a frequency within the range of 12-20 Hz, with an amplitude of 1 mA for a period of 0.2 ms, delivered via MNS can be used to entrain Mu-band neural oscillations within the brain at a frequency within the range of 8-12 Hz.

Figure 25A:
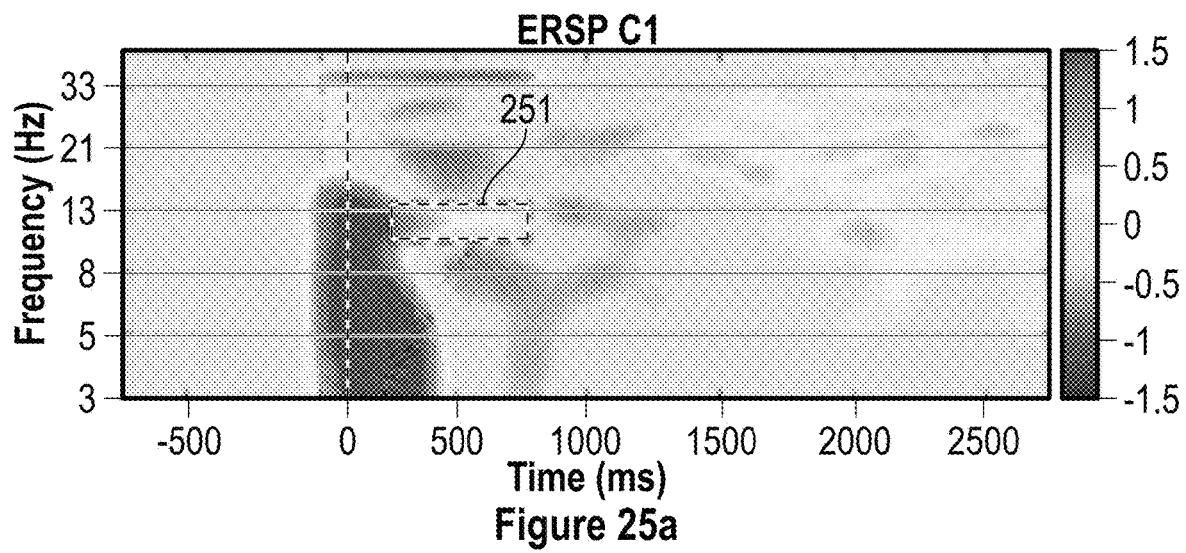
FIG. 25a shows a time-frequency analysis of average ERSP obtained from neural oscillations of each participant of the first study recorded at electrode C1 before, during and after delivery of a rhythmic pulse train.
Figure 25B:
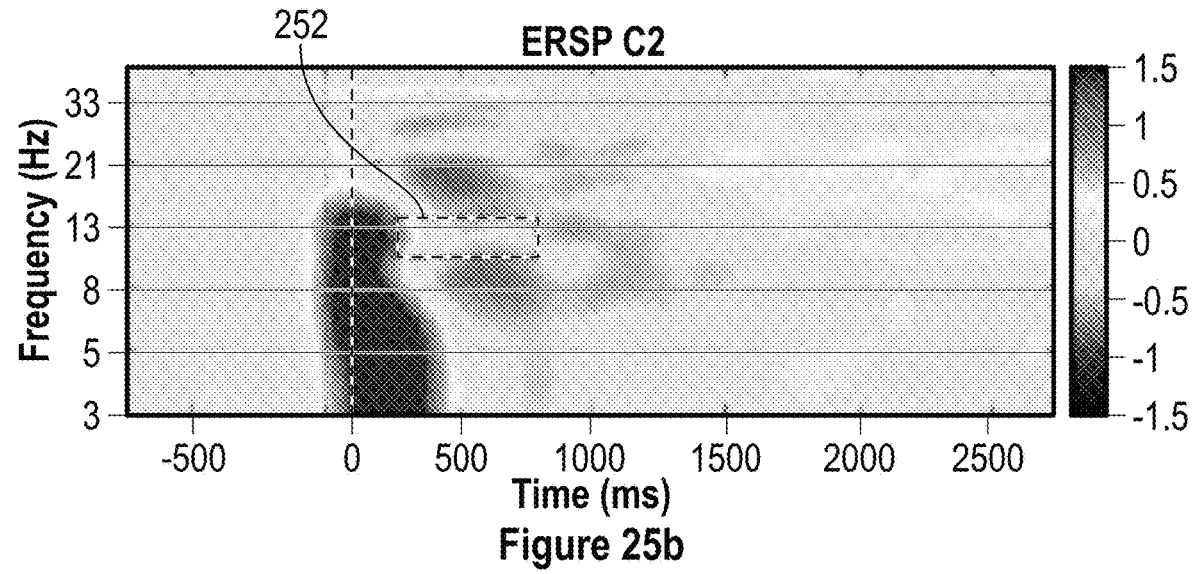
FIG. 25b shows a time-frequency analysis of average ERSP obtained from neural oscillations of each participant of the first study recorded at electrode C2 before, during and after delivery of a rhythmic pulse train.
Figure 25C:
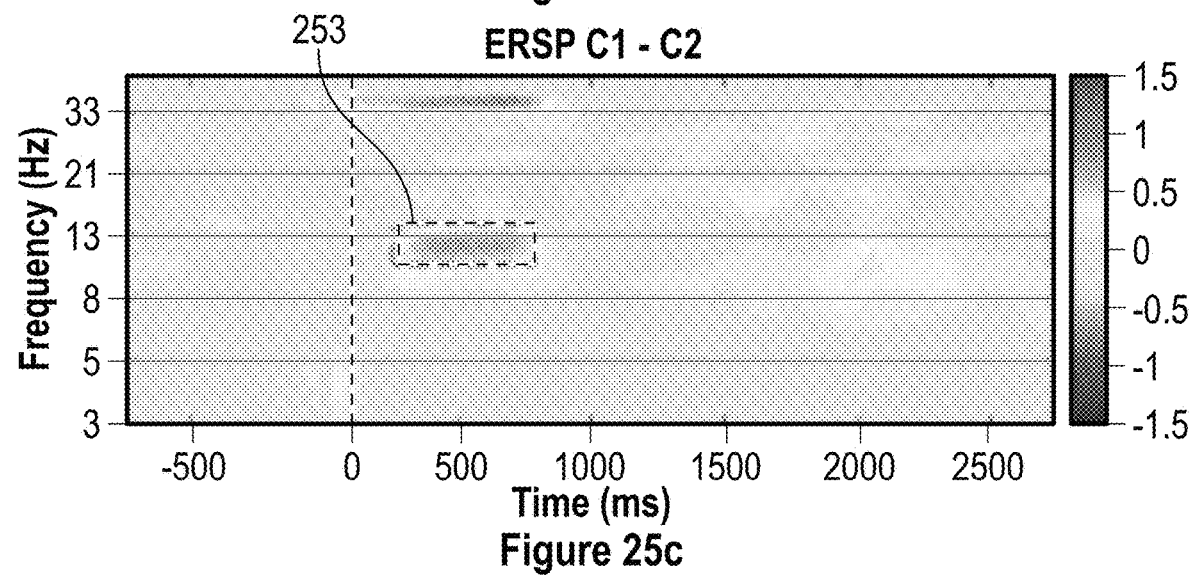
FIG. 25c shows the ERSP values of FIG. 25b subtracted from the ERSP values of FIG. 25a across the same time and frequency range.

FIG. 25*a* shows a time-frequency analysis of average ERSP obtained from neural oscillations of each participant of the study recorded at electrode C1 (as shown in FIGS. 5 and 9) before, during and after delivery of a rhythmic pulse train. Time is shown on the x-axis and frequency is shown on the y-axis. The colouring of the graph shows ERSP according to the scale shown to the right of the graph. Time=0 represents the onset of the arrhythmic pulse train. FIG. 25*b* shows a time-frequency analysis of average ERSP obtained from neural oscillations of each participant of the study recorded at electrode C2 (as shown in FIGS. 5 and 9) before, during and after delivery of a rhythmic pulse train. Time is shown on the x-axis and frequency is shown on the y-axis. The colouring of the graph shows ERSP according to the scale shown to the right of the graph. Time=0 represents the onset of the arrhythmic pulse train. FIG. 25*c* shows the ERSP values of FIG. 25*b* subtracted from the ERSP values of FIG. 25*a* across the same time and frequency range.

Electrode C2 corresponds to the ipsilateral hemisphere of the brain of each participant, i.e. the hemisphere of the brain on the same side of the body as the wrist to which the electrical stimulation is delivered. Electrode C1 corresponds to the contralateral hemisphere of the brain, i.e. the opposite hemisphere.

In FIGS. 25*a*-*c*, a widespread increase in ERSP during pulses 1-3 is seen in both the contralateral and ipsilateral hemispheres during rhythmic stimulation, but an increase in ERSP during pulses 4-10 is only seen in the contralateral hemisphere (shown by area 251 in FIG. 25*a*) and not in the ipsilateral hemisphere (shown by area 252 in FIG. 25*b*). This is also indicated by the area 253 in FIG. 25*c*.

Figure 26A:
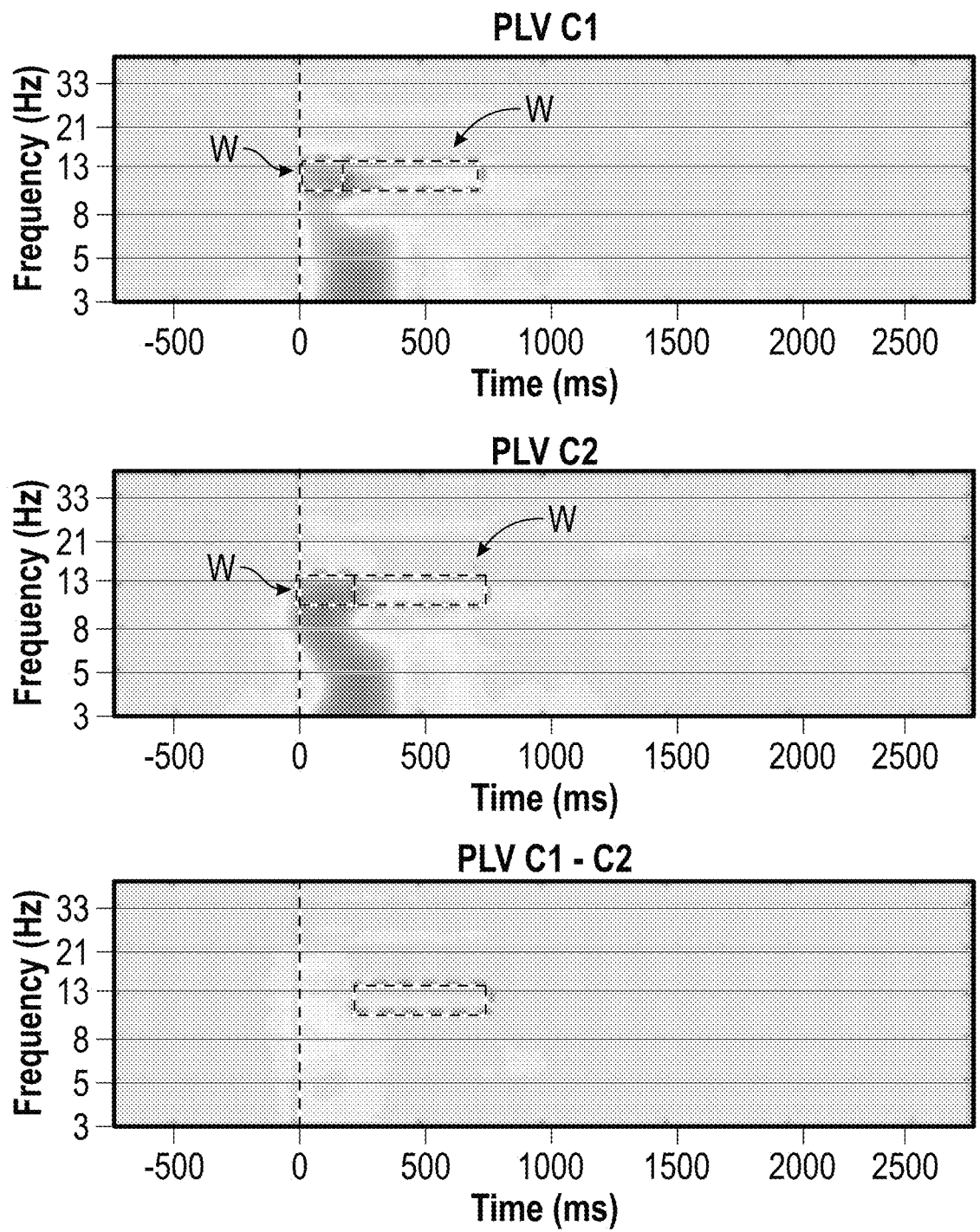
FIG. 26a shows a time-frequency analysis of PLV obtained from neural oscillations of each participant of the first study recorded at electrode C1 before, during and after delivery of a rhythmic pulse train, a time-frequency analysis of PLV obtained from neural oscillations of each participant of the first study recorded at electrode C2 before, during and after delivery of a rhythmic pulse train, and the difference in PLV obtained from neural oscillations of each participant of the first study recorded at electrode C1 and PLV obtained from neural oscillations of each participant of the first study recorded at electrode C2 across the same time and frequency range.

The top graph of FIG. 26*a* shows a time-frequency analysis of PLV obtained from neural oscillations of each participant of the study recorded at electrode C1 (as shown in FIGS. 5 and 9) before, during and after delivery of a rhythmic pulse train. The middle graph of FIG. 26*a* shows a time-frequency analysis of PLV obtained from neural oscillations of each participant of the study recorded at electrode C2 (as shown in FIGS. 5 and 9) before, during and after delivery of a rhythmic pulse train. Time is shown on the x-axis and frequency is shown on the y-axis in each graph. The colouring of the graphs indicates PLV, with darker colouring indicating greater PLV. Time=0 represents the onset of the respective pulse train. The bottom graph of FIG. 26*c* shows the PLV values of the middle graph of FIG. 26*a* subtracted from the PLV values of the top graph of FIG. 26*a* across the same time and frequency range.

Figure 26B:
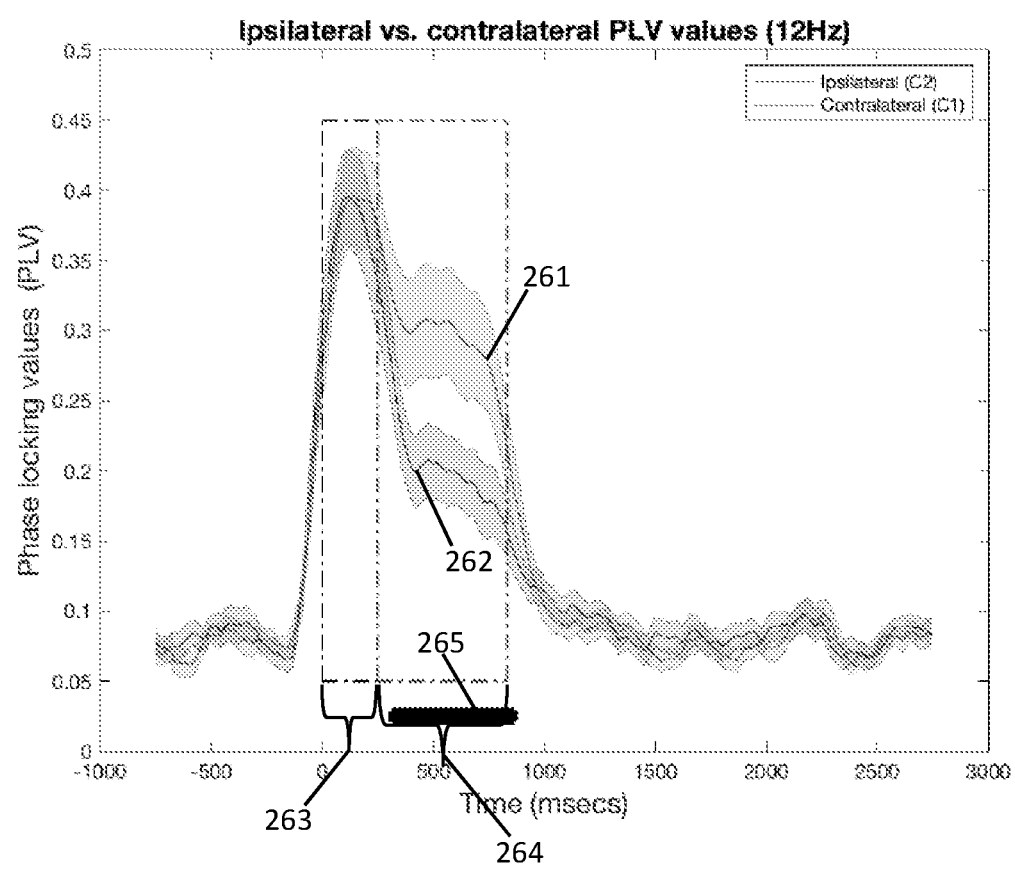
FIG. 26b shows PLV, obtained from 12 Hz neural oscillations of each participant of the first study, against time before, during and after delivery of a rhythmic pulse train measured at electrode C1 and at electrode C2.

FIG. 26*b* shows PLV across each participant of the study, obtained from 12 Hz neural oscillations, against time before, during and after delivery of a rhythmic pulse train measured at electrode C1 (line 261) and at electrode C2 (line 262). Time is shown on the x-axis and PLV is shown on the y-axis. Time=0 represents the onset of the respective pulse train. The area labelled 263 indicates the initial 1-3 pulses of the respective pulse train and the area labelled 264 indicates pulses 4-10 of the respective pulse train. The bar labelled 265 indicates a period of time during which the difference between PLV for electrode C1 and electrode C2 was statistically significant.

FIGS. 26*a*-*b* demonstrate that the first 3 stimulation pulses create a general effect that occurs in both hemispheres (as shown in the area 263 in FIG. 26*b*) but the entrainment effect seen in pulses 4-10 is more specific to the contralateral hemisphere and this is significantly different (as shown in the area 264 in FIG. 26*b*). PLV increased substantially for both hemispheres coincident with the onset of rhythmic stimulation (as shown in the area 263 in FIG. 26*b*). However, after the initial 1-3 pulses it reduced over the ipsilateral hemisphere but was sustained over the contralateral hemisphere (as shown in the area 264 in FIG. 26*b*) until stimulation ceased. The difference in PLV at the ipsilateral versus contralateral hemispheres was only statistically significant ($p<0.05^{FDR\text{-}corrected}$) during the latter period of stimulation (area 264 in FIG. 26*b*).

The results of FIGS. 25*a* to 26*b* demonstrate an initial (during pulses 1-3) broad increase in ERSP and PLV in response to both rhythmic and arrhythmic stimulation in both the ipsilateral and contralateral hemispheres. This effect is followed (during pulses 4-10) by a more specific increase in ERSP and PLV following rhythmic stimulation, which is specific to the contralateral hemisphere. These results suggest that unilateral MNS, i.e. MNS applied at only one side of the body, may be sufficient to provide the entrainment effects required to treat TS.

Figure 27:
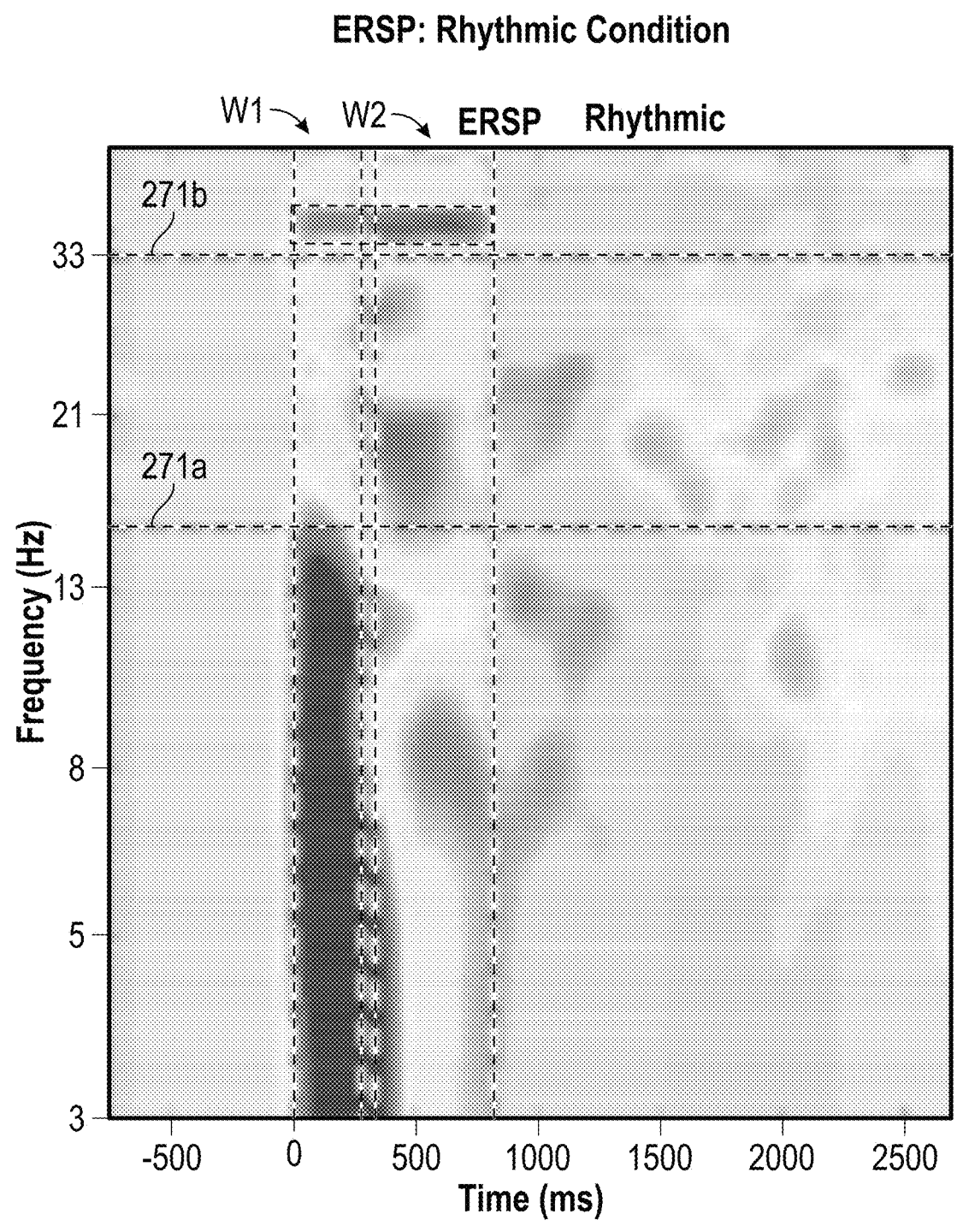
FIG. 27 shows a time-frequency analysis of average ERSP obtained from neural oscillations of each participant of the first study recorded at electrode C1 before, during and after delivery of a rhythmic pulse train.
Figure 28:
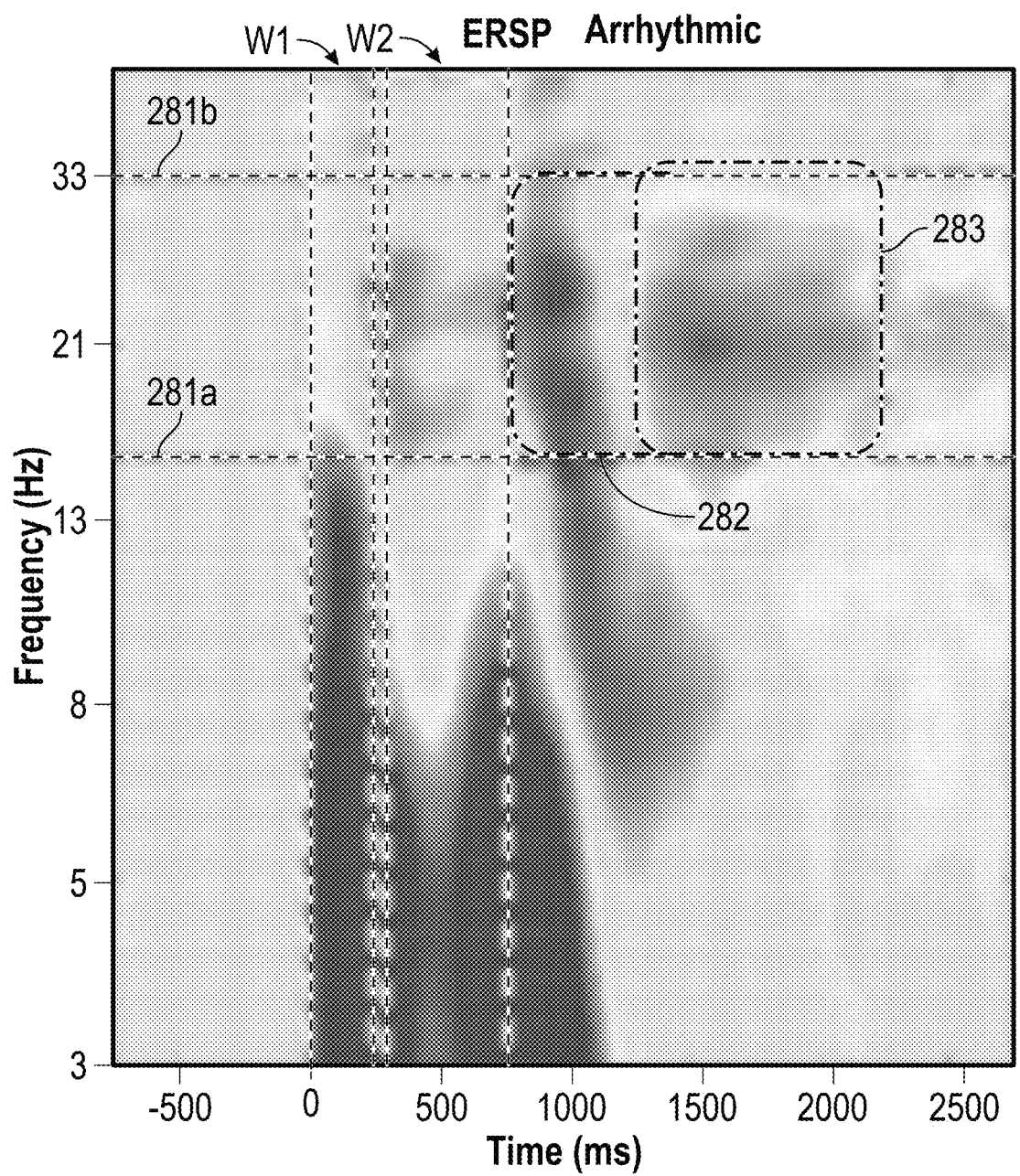
FIG. 28 shows a time-frequency analysis of average ERSP obtained from neural oscillations of each participant of the first study recorded at electrode C1 before, during and after delivery of an arrhythmic pulse train.

FIG. 27 shows a time-frequency analysis of average ERSP obtained from neural oscillations of each participant of the study recorded at electrode C1 (as shown in FIGS. 5 and 9) before, during and after delivery of a rhythmic pulse train. Time is shown on the x-axis and frequency is shown on the y-axis. The colouring of the graph shows ERSP, with darker colouring indicating greater ERSP. Time=0 represents the onset of the rhythmic pulse train. FIG. 28 shows a time-frequency analysis of average ERSP obtained from neural oscillations of each participant of the study recorded at electrode C1 (as shown in FIGS. 5 and 9) before, during and after delivery of an arrhythmic pulse train. Time is shown on the x-axis and frequency is shown on the y-axis. The colouring of the graph shows ERSP, with darker colouring indicating greater ERSP. Time=0 represents the onset of the arrhythmic pulse train.

ERD (indicated by area 282 in FIG. 28) is shown in the 15-30 Hz frequency range (between lines 271a and 271b, and 281a and 281b of FIGS. 27 and 28 respectively) following pulse 10 of both the rhythmic and arrhythmic pulse trains. This was followed by a rebound, i.e. ERSP not returning to baseline levels but instead overshooting and increasing beyond baseline levels, (indicated by area 283 in FIG. 28) in the 15-30 Hz frequency range after the arrhythmic train. A rebound following the rhythmic train is absent. It is believed that the rebound following the arrhythmic train may reflect GABA-dependent inhibitory activity that cancels out movement-related processes. As such, ERD may be linked to movement and subsequent ERS, i.e. the rebound following the arrhythmic train, may be associated with movement suppression.

FIGS. 27 and 28 also show that for a period of time W1 immediately following the delivery of the first pulse of a train, during the delivery of pulses 1-3, there is an increase in ERSP of brain oscillations in both the rhythmic and arrhythmic cases. This increase in ERSP is believed to represent an initial response to the stimulation train rather than true entrainment. In contrast, for a period of time W2 following the delivery of the initial pulses, during delivery of pulses 4-10, an increase in ERSP of brain oscillations may be observed in the arrhythmic case but not in the rhythmic case. This increase is believed to reflect entrainment, and was observed in the contralateral hemisphere of the brain.

Figure 29:
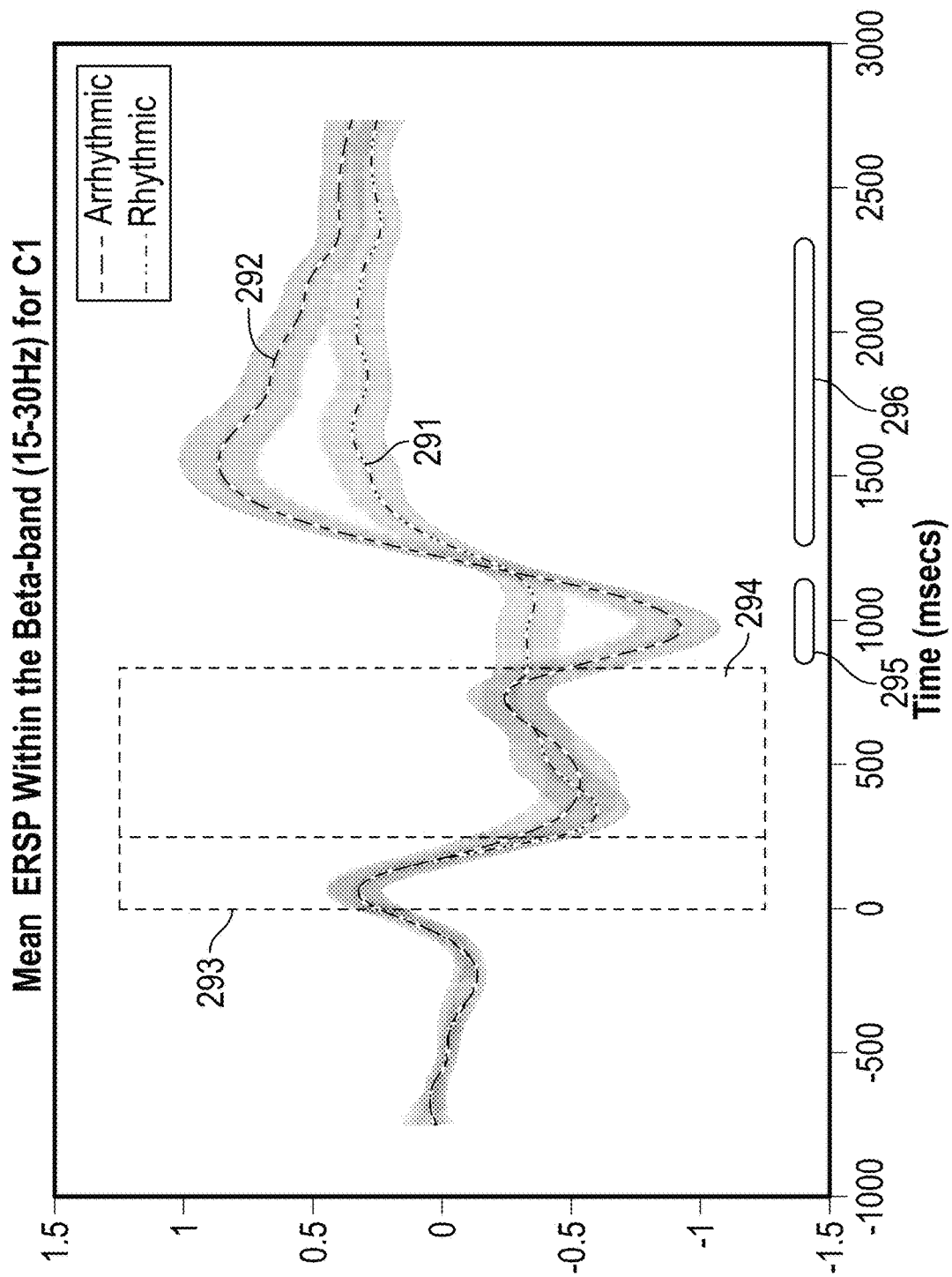
FIG. 29 shows average ERSP obtained from Beta-band neural oscillations of each participant of the first study recorded at electrode C1 against time before, during and after delivery of a rhythmic pulse train and before, during and after delivery of an arrhythmic pulse train.

FIG. 29 shows average ERSP obtained from Beta-band neural oscillations of each participant of the study recorded at electrode C1 against time before, during and after delivery of a rhythmic pulse train (line 291) and before, during and after delivery of an arrhythmic pulse train (line 292). Time is shown on the x-axis and ERSP is shown on the y-axis. Time=0 represents the onset of the respective pulse train. The area labelled 293 indicates the initial 1-3 pulses of the respective pulse train and the area labelled 294 indicates pulses 4-10 of the respective pulse train. The bars labelled 295 and 296 indicate a periods of time during which the difference between ERSP for the rhythmic and arrhythmic pulse trains was statistically significant.

Figure 30:
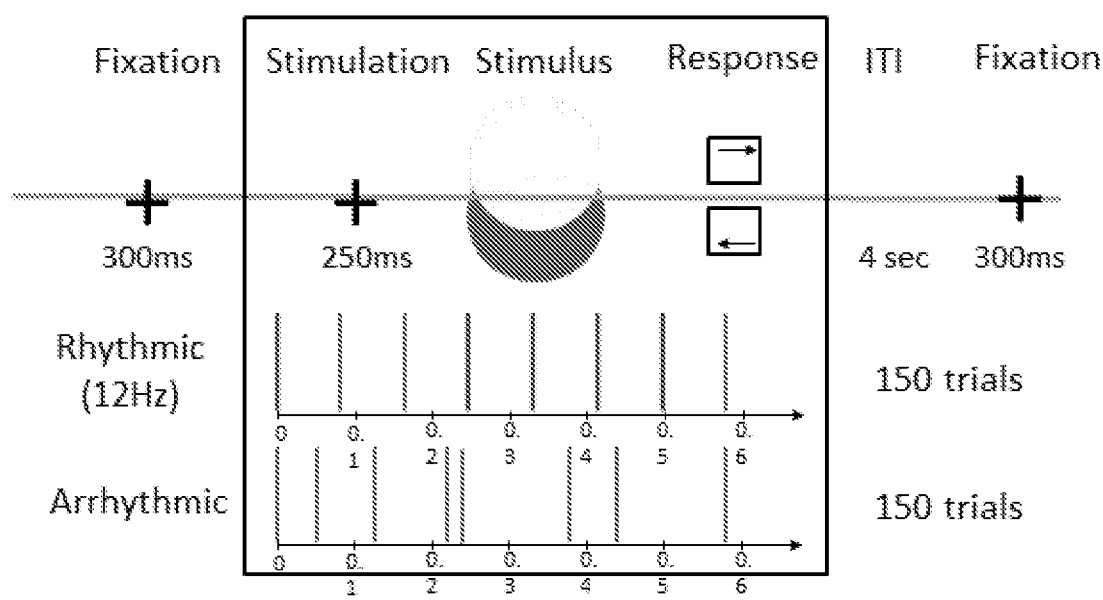
FIG. 30 illustrates the design of a second study.

FIG. 30 illustrates the design of another example study. In the study, an electrical nerve stimulator according to an embodiment of the invention was used to deliver electrical square wave pulses to the median nerve of the right wrist of each of a plurality of participants. 150 pulse trains each at a frequency of 12 Hz (rhythmic pulse trains) and 150 pulse trains with a non-uniform interval between each pulse (arrhythmic pulse trains) were delivered to each participant. Each pulse train comprised 8 pulses and a gap of 4 seconds was provided between the delivery of each pulse train. The delivery of pulses at a frequency of 12 Hz is referred to as rhythmic stimulation and the delivery of pulses with a non-uniform interval between each pulse is referred to as arrhythmic stimulation. Each pulse lasted 250 ms. The reaction time of each participant during a task involving keypress responses using the right hand during both rhythmic and arrhythmic stimulation was measured.

Figure 31:
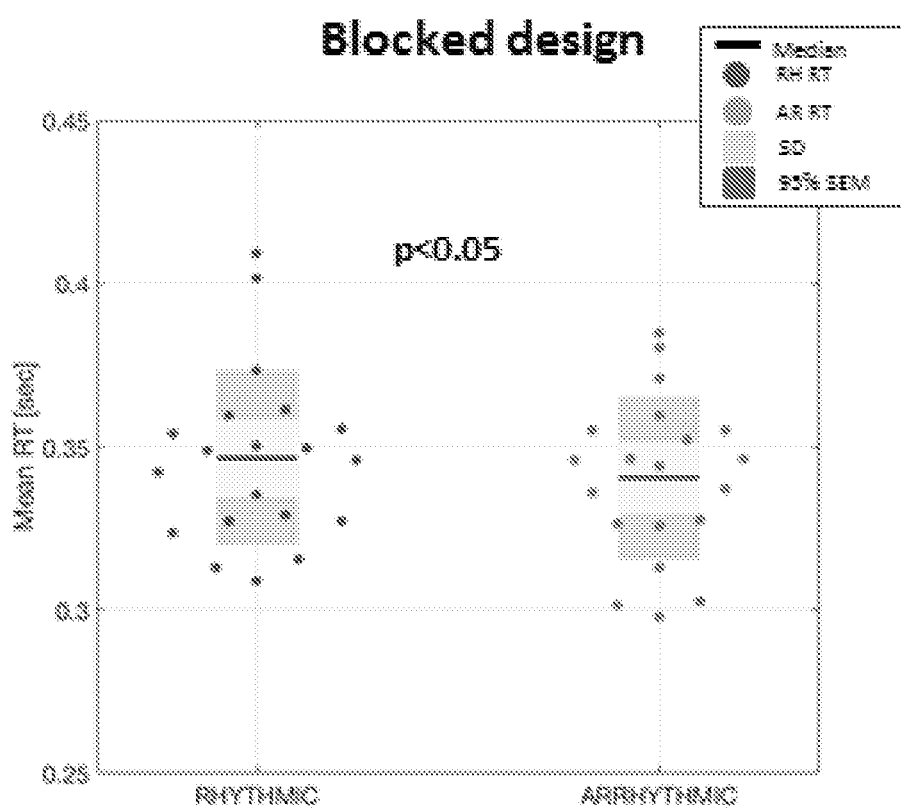
FIG. 31 shows a graph of mean reaction time recorded during the second study during rhythmic stimulation and arrhythmic stimulation for blocked stimulation.
Figure 32:
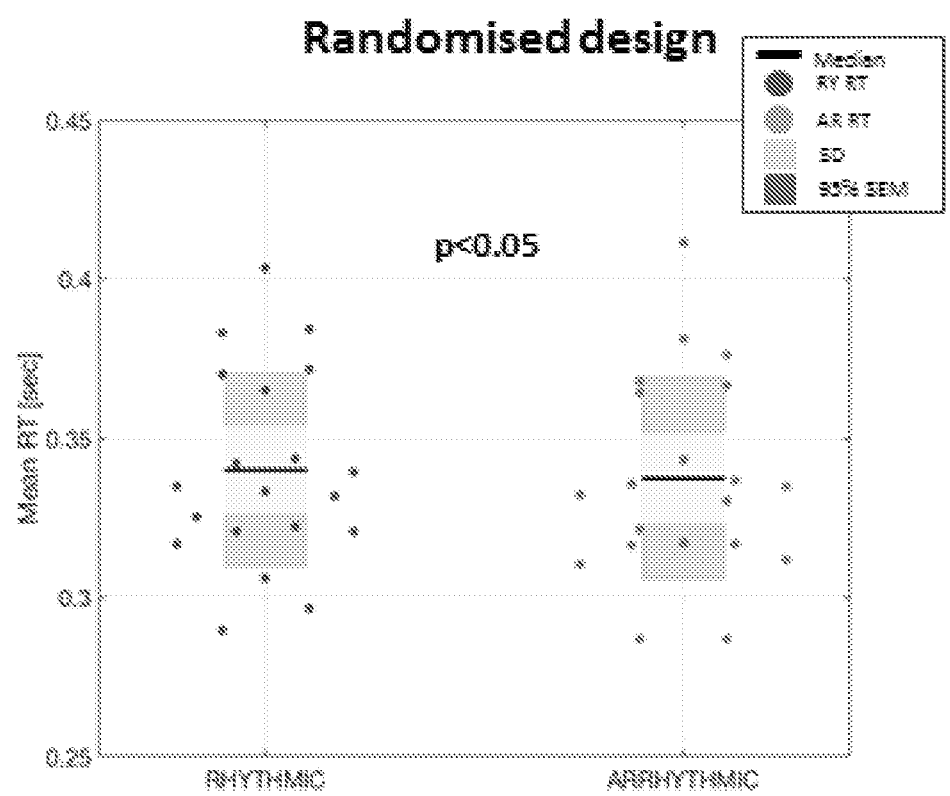
FIG. 32 shows a graph of mean reaction time recorded during the second study during rhythmic stimulation and arrhythmic stimulation for randomised stimulation.

FIG. 31 shows a graph of mean reaction time (y-axis) during rhythmic stimulation (left-hand plot) and arrhythmic stimulation (right-hand plot) for blocked stimulation, i.e. for the case in which the 150 rhythmic pulse trains were delivered during a different time period to the delivery of the 150 arrhythmic pulses. FIG. 32 shows a graph of mean reaction time (y-axis) during rhythmic stimulation (left-hand plot) and arrhythmic stimulation (right-hand plot) for randomised stimulation, i.e. for the case in which delivery of the rhythmic pulse trains was interspersed with the delivery of the arrhythmic pulse trains such that the order in which rhythmic and arrhythmic pulse trains were delivered was randomised. Each point on the graph represents the mean reaction time of one of the participants. Median reaction time is indicated by the solid horizontal line on the respective plot. For the results shown, $p<0.5$. The results illustrate how rhythmic stimulation induces a significant (but small) slowing of the average choice reaction time relative to arrhythmic stimulation.

Figure 33A:
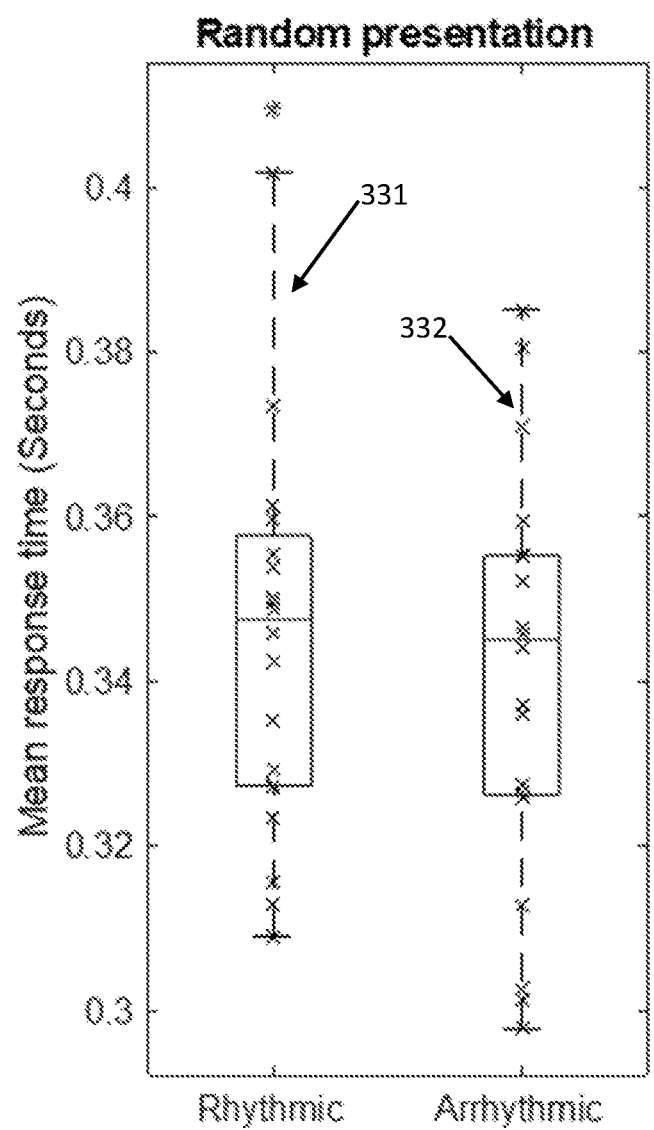
FIG. 33a shows a first plot of mean reaction time (RT) during rhythmic stimulation and a second plot of RT recorded during arrhythmic stimulation during randomised delivery of pulse trains recorded during a third study.
Figure 33B:
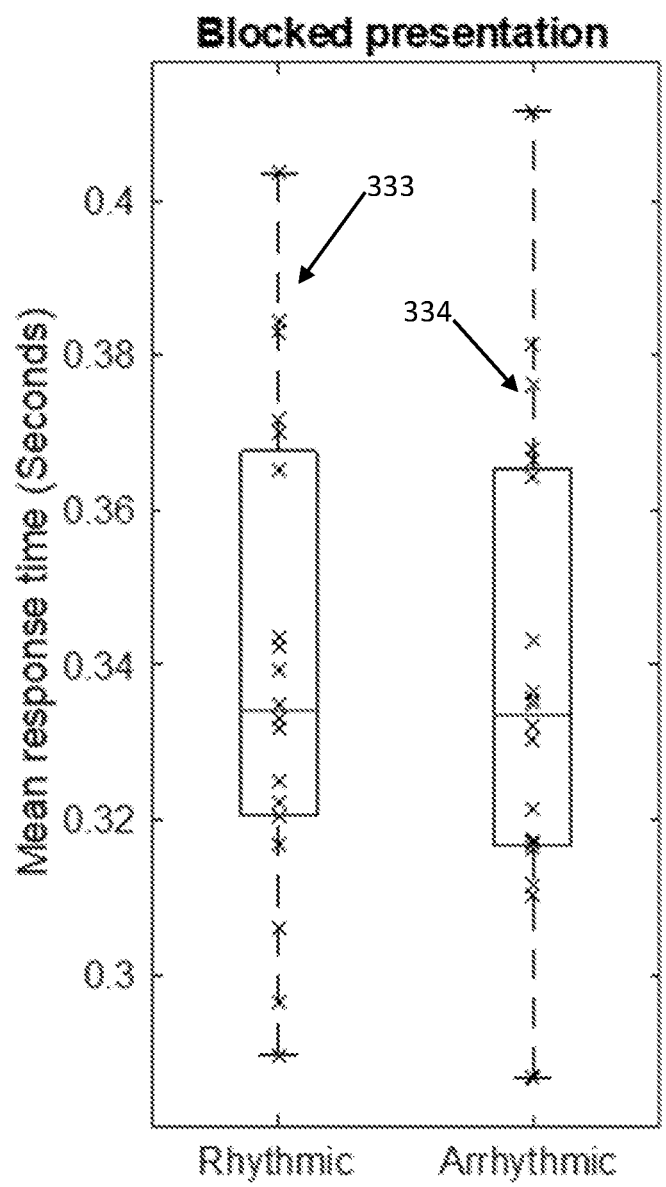
FIG. 33b shows a third plot of mean RT recorded during rhythmic stimulation and a fourth plot of RT recorded during arrhythmic stimulation during blocked delivery of pulse trains recorded during the third study.

FIGS. 33a and 33b show the results of another example study in which an electrical nerve stimulator according to an embodiment of the invention was used to deliver rhythmic and arrhythmic stimulation to each of a plurality of participants. FIG. 33a shows results for randomised stimulation and FIG. 33b shows results for blocked stimulation. Each participant completed a choice reaction time (CRT) test during both rhythmic and arrhythmic stimulation and the reaction time (RT) of each correct trial, i.e. each time a participant selected the correct choice of the CRT, was recorded.

FIG. 33a shows a first plot 331 of mean RT (y-axis) of each of the participants when exposed to rhythmic stimulation, and a second plot 332 of mean RT (y-axis) of each of the participants when exposed to arrhythmic stimulation. FIG. 33b shows a third plot 333 of mean RT (y-axis) of each of the participants when exposed to rhythmic stimulation, and a fourth plot 334 of mean RT (y-axis) of each of the participants when exposed to arrhythmic stimulation. FIGS. 33a and 33b show that mean RT for correct trials was significantly slowed by rhythmic stimulation compared to arrhythmic stimulation in both studies (Randomised presentation (first study—FIG. 33a): $t(19)=2.01$, $p=0.029$, effect-size (Hedges' g)=0.23; Blocked presentation (second study—FIG. 33b): $t(19)=2.56$, $p<0.01$, effect-size (Hedges' g)=0.08). Although these results demonstrate that rhythmic stimulation resulted in a statistically significant slowing of mean RT relative to arrhythmic stimulation, the magnitude of this effect is very small. Rhythmic stimulation led to no material impairment in the execution of volitional movements.

Figure 34:
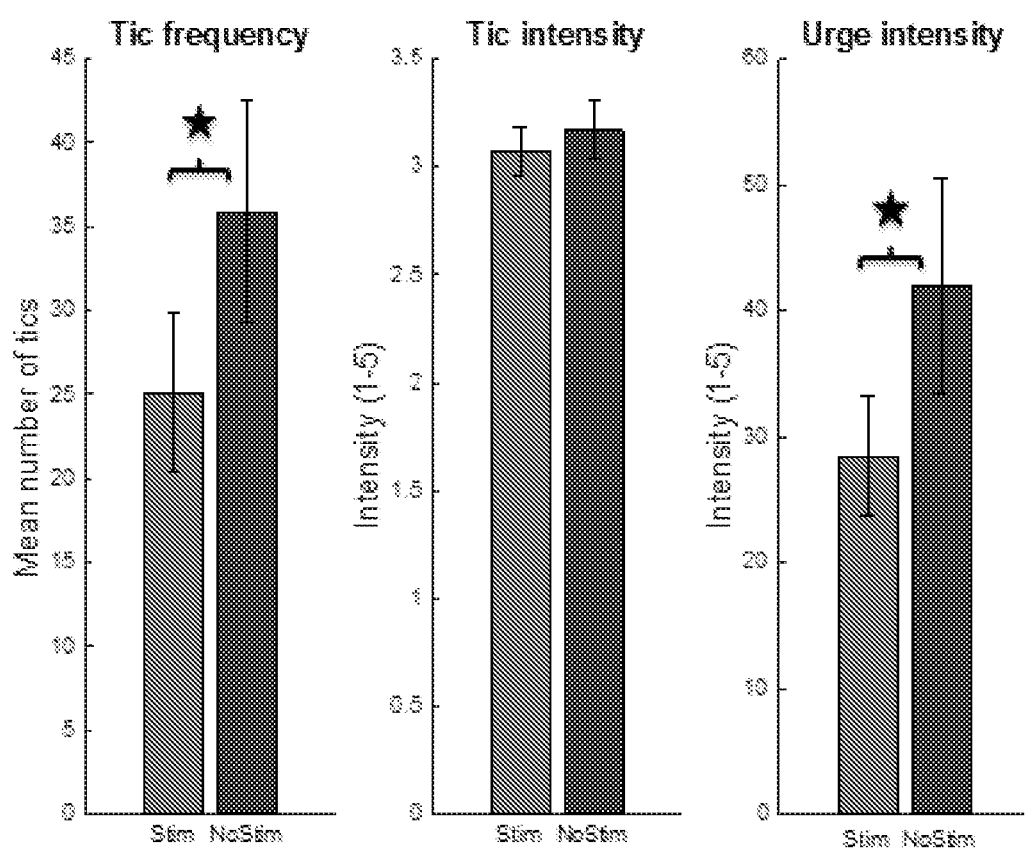
FIG. 34 shows tic frequency, tic intensity and the intensity of urges to tic recorded during rhythmic stimulation during a fourth study.

FIG. 34 shows the results of another example study in which an electrical nerve stimulator according to an embodiment of the invention was used to deliver rhythmic stimulation, at a frequency selected from the same frequency range as Mu-band neural oscillations, to each of a plurality of participants having Tourette's syndrome. The results show reductions in tic frequency, tic intensity and the intensity of urges to tic when the stimulation is administered (results shown in left-hand bar of each chart of FIG. 34) compared to when no stimulation is administered (results shown in right-hand bar of each chart of FIG. 34). Tic frequency was reduced by 30.15%, tic intensity was reduced by 3.08% and urge intensity was reduced by 32.35%.

Figure 35A:
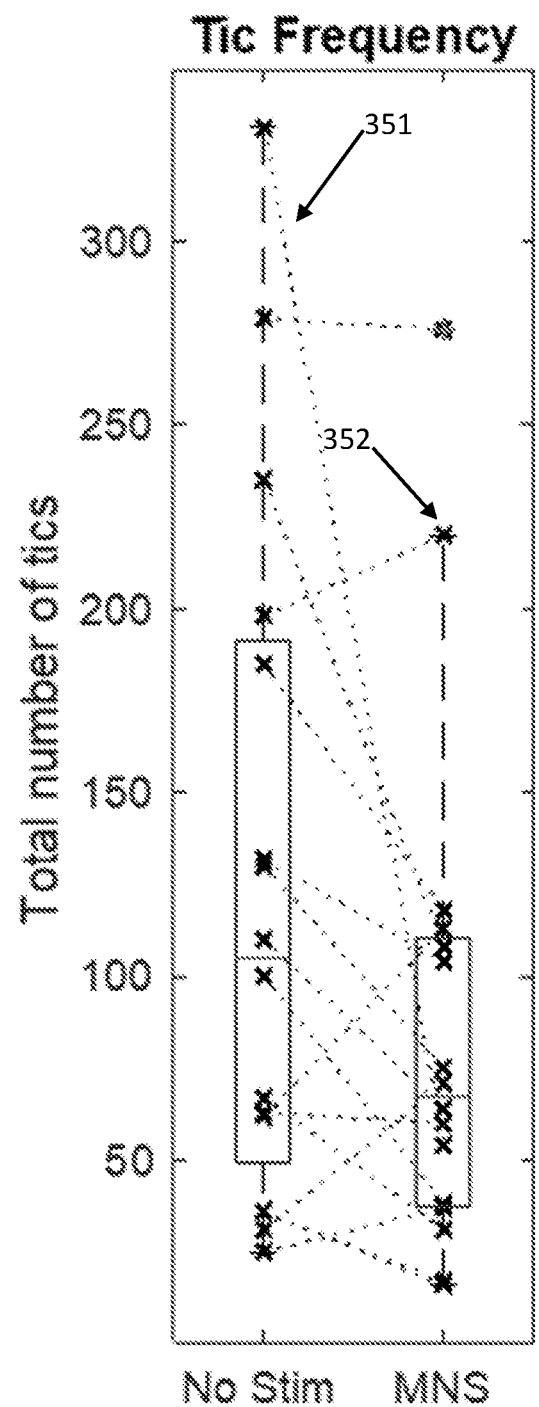
FIG. 35a shows a first plot of total number of tics recorded during a period of no stimulation and second plot of total number of tics recorded during a period of rhythmic stimulation recorded during a fifth study.
Figure 35B:
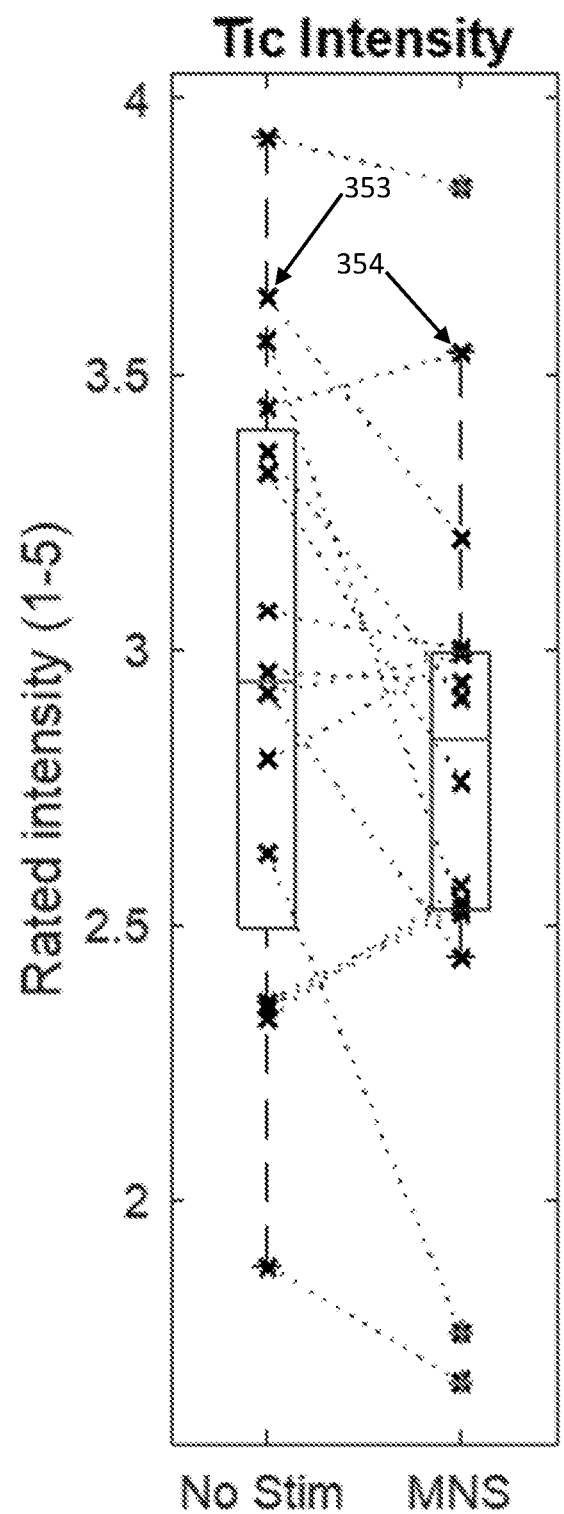
FIG. 35b shows a third plot of rated tic intensity recorded during a period of no stimulation and fourth plot of rated tic intensity recorded during a period of rhythmic stimulation recorded during the fifth study.
Figure 35C:
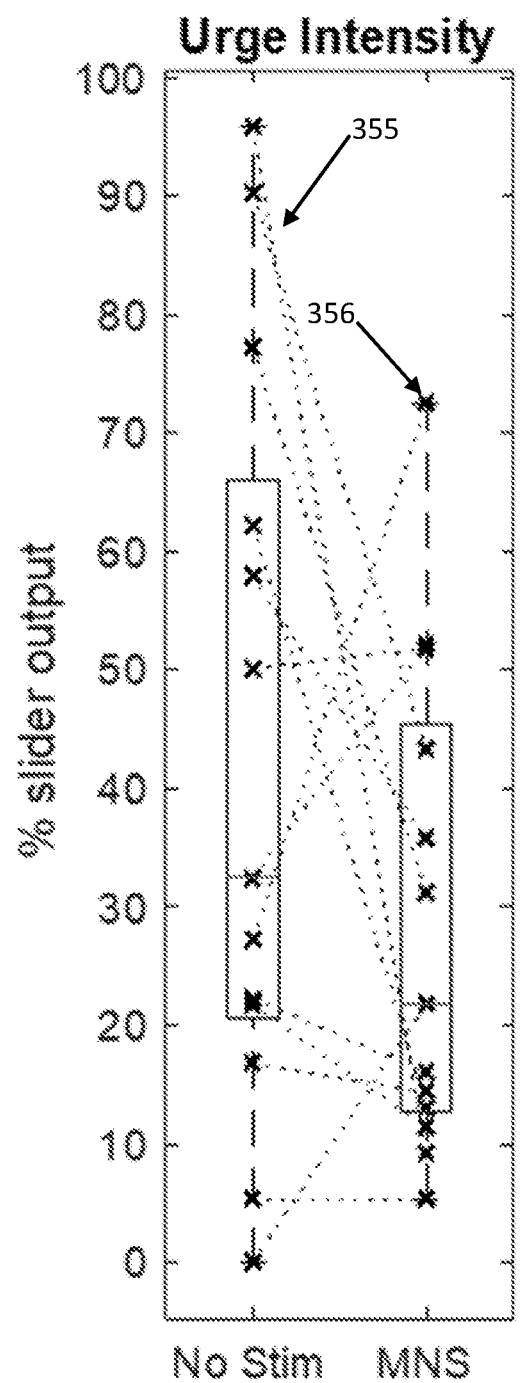
FIG. 35c shows a fifth plot of self-estimated urge-to-tic reported during a period of no stimulation and a sixth plot of self-estimated urge-to-tic reported during a period of rhythmic stimulation recorded during the fifth study.

FIGS. 35a-c show the results of another example study in which an electrical nerve stimulator according to an embodiment of the invention was used to deliver rhythmic stimulation, at a frequency selected from the same frequency range as Mu-band neural oscillations, to each of a plurality of participants having Tourette's syndrome. The frequency of stimulation was selected as 10 Hz and MNS was delivered to the right wrist. During the study, each participant was video recorded while receiving randomly interleaved 1-minute periods of rhythmic MNS versus no stimulation. Throughout the study, participants were required to continuously report their self-estimated urge-to-tic. The video recordings were subject to a carefully conducted, blind, analysis of tic frequency and tic intensity during each 1-minute period of MNS or no stimulation, and self-estimated urge-to-tic ratings were similarly computed for MNS and no stimulation. FIG. 35a shows a first plot 351 of total number of tics (y-axis) for each participant during the study when no MNS was delivered. FIG. 35a further shows a second plot 352 of total number of tics (y-axis) for each participant during the study when MNS was delivered. FIG. 35b shows a third plot 353 of rated tic intensity (y-axis) for each participant during the study when no MNS was delivered. FIG. 35b further shows a fourth plot 354 of rated tic intensity (y-axis) for each participant during the study when MNS was delivered. Tic intensity was rated on the Yale Global Tic Severity Scale (YGTSS). Minimal tics, i.e. tics that are usually not noticed as they involve subtle movements of muscles, scored 1; mild tics, i.e. tics that are usually not noticed but are more forceful than minimal tics, scored 2; moderate tics, i.e. tics that are not outside the range of normal expression, scored 3; marked tics, i.e. tics that are on an exaggerated character, scored 4; and severe tics, scored 5. FIG. 35c shows a fifth plot 355 of reported self-estimated urge-to-tic (y-axis) for each participant during the study when no MNS was delivered. FIG. 35c further shows a sixth plot 356 of reported self-estimated urge-to-tic (y-axis) for each participant during the study when MNS was delivered. FIGS. 35a-c demonstrate that the impact of rhythmic MNS on urge intensity, tic frequency and tic intensity is variable across individuals.

Figure 36A:
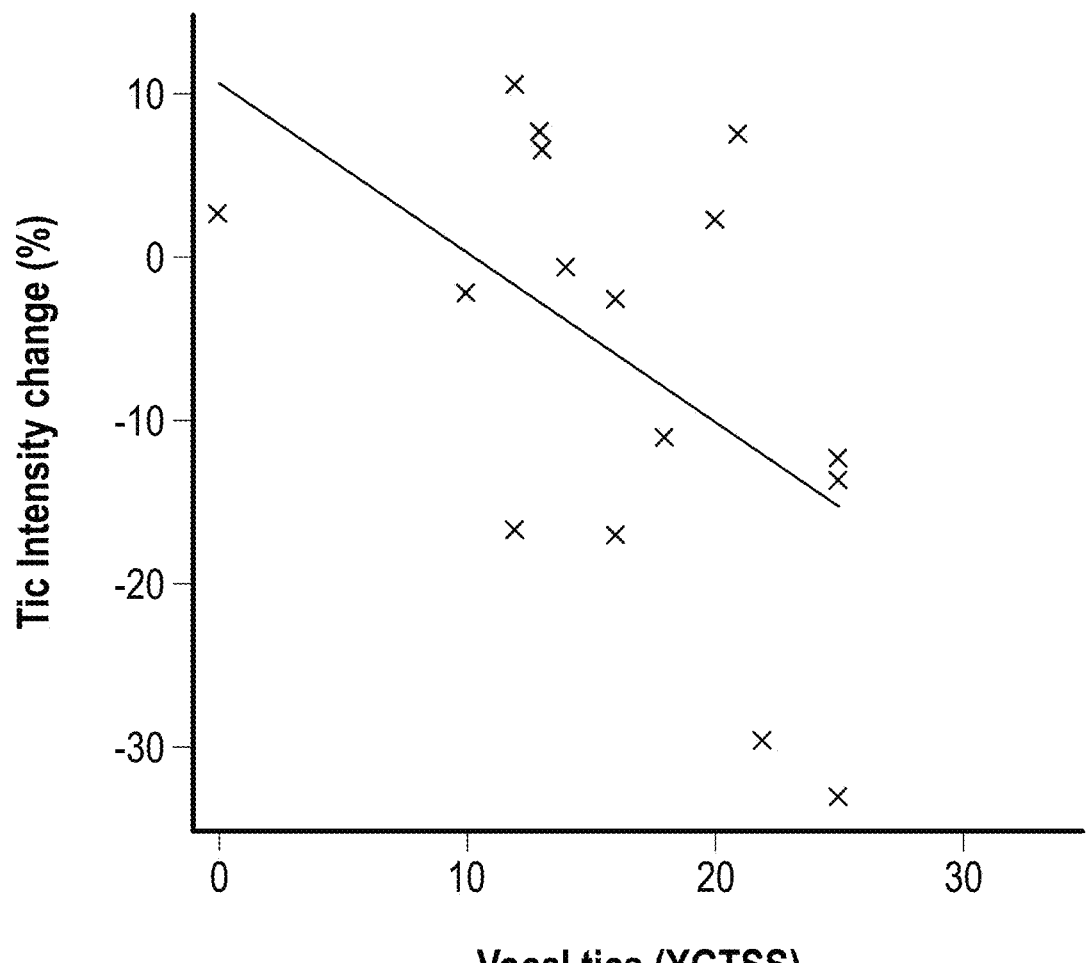
FIGS. 36a-b show the results of multiple regression analyses were conducted on the data shown in FIGS. 35a-c.
Figure 36B:
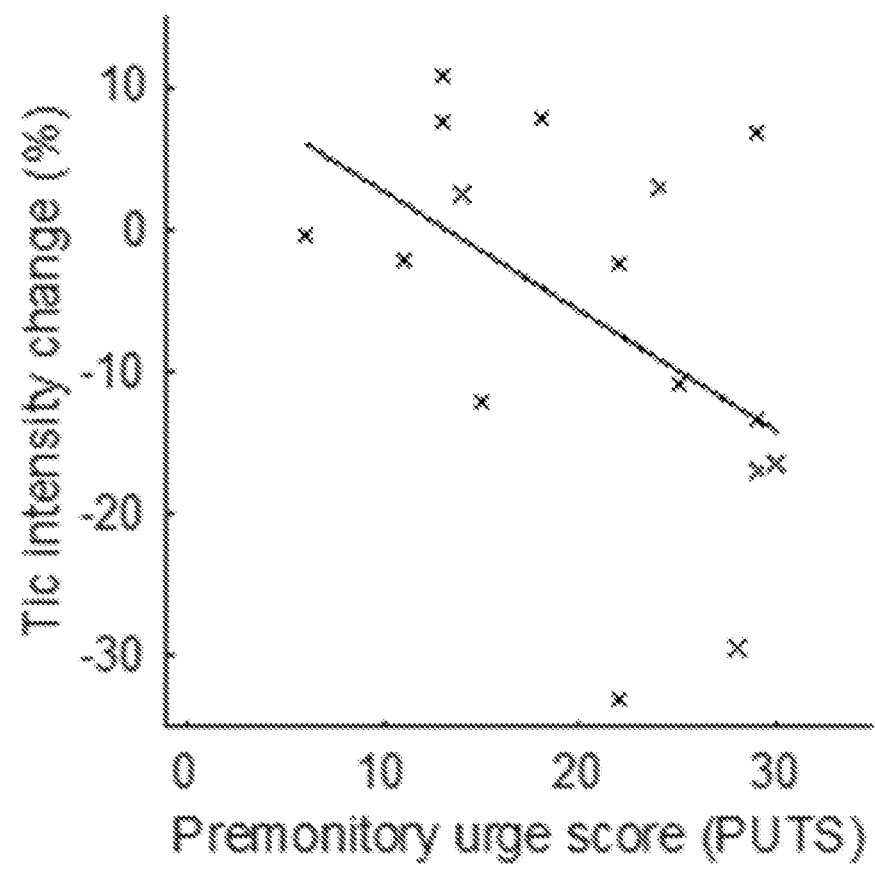

Multiple regression analyses were conducted on the data shown in FIGS. 35a-c. The results of these analyses are presented in FIGS. 36a-b. Separate stepwise multiple regression analyses were conducted in which the following variables: Age, Sex, IQ, Premonitory Urge for Tics Scale (PUTS), Impairment, Motor, Vocal, and YGTSS scores were used to predict the magnitude of the effects of MNS on (a) MNS induced change in tic frequency, (b) MNS induced change in tic intensity, and (c) MNS induced change in urge intensity. The results of these analyses indicated that those individuals who exhibited the most severe clinical symptoms showed the most benefit from rhythmic MNS. Specifically, YGTSS and PUTS scores were significant predictors of the MNS induced change in tic intensity (YGTSS scores: $t(15)=-2.52$, $p<0.26$; PUTS scores: $t(15)=-2.34$, $p<0.36$; $F=6.19$, Adj-Rsq=0.41, $p<0.013$). FIG. 36a shows a scatter plot of change in tic intensity with exposure to rhythmic MNS (y-axis) against YGTSS score (x-axis). FIG. 36b shows a scatter plot of change in tic intensity with exposure to rhythmic MNS (y-axis) against PUTS score (x-axis). In each case, negative values on the y-axis indicate a reduction in clinical symptoms while positive values on the x-axis indicates increase in clinical symptoms.

All participants were asked to comment on their experience of the stimulation and any spontaneous comments were recorded. All participants reported that the stimulation had been effective, and that it had influenced their TS symptoms. Some reported that the stimulation had reduced their tics, and others reported that the stimulation had primarily removed or reduced their urge-to-tic. Others stated that the stimulation had affected both their tics and their urge-to-tic. For example, individual participants stated that: muscles that never relax did so on the during MNS; that stimulation definitely decreased their urges; that MNS stopped them from wanting to tic; that with the stimulation they didn't need to tic as much; and, that during MNS their urges were reduced and their tics weren't on their mind. Three others reported that stimulation made them calmer. One participant said that the stimulation reduced their urges a great deal but not their tics, and so with the stimulation they could no longer tell when their tics were going to happen. Several participants wondered if the reduction of tics they experienced was due to the distracting nature of the stimulation. Three participants stated that the effects of the stimulation lasted for some time after it had ceased. This latter point was confirmed in the video analysis.

FIGS. 34a-c demonstrate that rhythmic MNS can significantly reduce both tic frequency (i.e. the total number of tics recorded over a given period of time) and tic intensity compared to comparable time periods of no stimulation. A mean tic frequency for no stimulation of 87.6 (±71.4) was recorded and a mean tic frequency for rhythmic MNS of 126.3 (±94.5) was recorded for the same time period, where $t(15)=2.36$, $p=0.03$ (see FIG. 34a). A mean tic intensity for no stimulation of 3.0 (±0.6) was recorded and a mean tic intensity for rhythmic MNS of 2.8 (±0.6) was recorded for the same time period, where $t(15)=2.41$, $p=0.03$ (see FIG. 34b). By contrast, the results show only a marginally significant difference between self-estimated urge-to-tic during rhythmic MNS and during no stimulation. A mean self-estimated urge-to-tic for no stimulation of 41.3(±31.7) was recorded and a mean self-estimated urge-to-tic for rhythmic MNS of 29.1 (±20.7) was recorded, where $t(15)=1.83$, $p=0.09$ (see FIG. 34c).

For some participants, the effects of rhythmic MNS were only observed during the stimulation, whereas other participants reported the effects of rhythmic MNS outlasting the period of stimulation itself for some time. This may lead to a potential under-estimation of the beneficial effects of MNS when comparing interleaved periods of MNS with no stimulation.

Pearson correlation and linear regression techniques were used to investigate how MNS-induced changes in tic frequency are associated with alterations in self-estimated urge-to-tic. This analysis revealed a positive correlation ($r=0.75$, $R2=0.56$, $F=12.74$, $p=0.005$), indicating that a reduction in tic frequency was associated with a reduction in self-estimated urge-to-tic experiences, and demonstrated that the observed MNS-induced reduction in tic frequency accounted for approximately 56% of the variance in the self-estimated urge-to-tic.

A further study was carried out to determine if the reduction in tic frequency and intensity observed during rhythmic MNS could in any way be attributed to the stimulation providing a distraction from the urge to tic. The effects of rhythmic MNS on a sample of twenty participants performing an attention-demanding continuous performance task (CPT) were measured. The results of the study demonstrated that MNS had no significant distracting effect on participants performance in the CPT. Specifically, there was no effect of MNS on the number of errors made during MNS relative to the no stimulation condition. A mean of the total number of errors during no stimulation of 11.9 (±5.1) was recorded, and a mean of the total number of errors during rhythmic 12 Hz MNS of 12.3 (±4.9) was recorded, where p=0.65. A mean of commission errors during no stimulation of 10.34 (±4.5) was recorded, and a mean of commission errors during rhythmic 12 Hz MNS of 10.6 (±4.4) was recorded, where p=0.72. A mean of omission errors during no stimulation of 1.56 (±1.3) was recorded, and a mean of omission errors during rhythmic 12 Hz MNS of 1.68 (±1.8) was recorded, where p=0.72. No effect of MNS on mean reaction time (RT) for correct trials during MNS relative to no stimulation (where p=0.35) was observed. An additional Bayesian analysis was conducted to evaluate the likelihood of the null result. This analysis confirmed the non-significant alternative hypothesis for both errors (BF10=0.26) and correct RTs (BF10=0.39) and revealed strong evidence in favour of the null hypothesis for both errors (BF01=3.9) and correct RTs (BF01=2.86).

In another example study, an electrical nerve stimulator according to an embodiment of the invention was used to deliver a plurality of trains of electrical square wave pulses to each of a plurality of participants. In the example study, the controller of the electrical nerve stimulator comprised a Digitimer DS7A HV Current Stimulator (available from Digitimer Ltd, Hertfordshire, UK). In other example implementations of the electrical nerve stimulator, any suitable controller may be used. The electrode of the electrical nerve stimulator comprised a bar electrode comprising two stainless steel disk electrodes, comprising an anode and a cathode, with a diameter of 8 mm separated by 30 mm. Stimulation was delivered in the form of MNS at the right-hand wrist od each participant. The intensity of the stimulation used was the minimum intensity at which a thumb twitch was seen. The stimulator was controlled by a bespoke MATLAB vR2017a script on a Mac Pro computer running High Sierra (v. 10.13.6).

EEG data was recorded using the same 64 electrodes shown in FIGS. 5 and 9 using a BioSemi Active Two system. EEG data was recorded with a sampling rate of 1024 Hz, later downsampled to 128 Hz. The impedance of the electrodes was kept under 30V for all participants. Reference electrodes were placed on the left and right mastoids. Bipolar vertical and horizontal EOG electrodes were also recorded. The central scalp electrode (C1) was located over the left sensorimotor cortical area of each participant.

Figure 37:
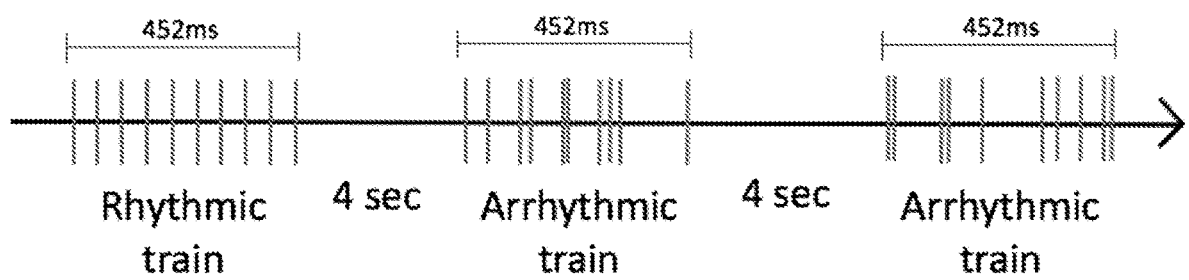
FIG. 37 shows three groups, or 'trains', of electrical pulses delivered to each of a plurality of participants of a sixth study.

In the study 300 pulse trains, each consisting of 10 pulses of MNS, were delivered once every 4 seconds while EEG was being recorded. The duration of each individual pulse, i.e. the pulse width, was 200 µs and the total duration of the pulse trains was 452 ms. Pulse trains were delivered randomly in two different conditions; in a rhythmic condition, wherein pulses were delivered every 52 ms (i.e. at a frequency of 19 Hz), and in an arrhythmic condition, wherein pulses were delivered during the same time window as the rhythmic condition (i.e., 452 ms), but the intervals between individual pulses was not uniform and were selected pseudorandomly for each pulse train. Three of the trains are illustrated in FIG. 37.

EEGlab (14.1.1) was used to pre-process and analyse the EEG recordings. Data were lowpass filtered at 45 Hz and high-pass filtered at 1 Hz. Channels showing aberrant behaviour were deleted and noisy channels were interpolated. Automatic Artefact Removal (AAR) was used to remove EOG artefacts, using recursive least squares regression. Time-windows of −1 to 3 seconds, time-locked to the first pulse of each train were extracted. Epochs showing abnormal trends or excessive noise were rejected. Specifically, epochs showing a signal amplitude at +−100 V in one or more channels were be rejected; those epochs with signal slopes exceeding a threshold of 50 V in one or more channels were be rejected; those epochs with 5 times the standard deviation in the probability distribution were rejected; those epochs which their kurtosis statistic was larger than 5 times of the standard deviation of the data were rejected. Artefacts were detected by running Independent Component Analysis (ICA) and components were rejected with the use of Multiple Artefact Rejection Algorithm (MARA) and visual inspection. In total, based upon these criteria, only one channel was deleted from one participant. The average number of epochs between participants after epoch rejection was 129 in the rhythmic condition and 126 in the arrhythmic condition.

Analyses of the EEG data was performed to obtain ERSP values and PLV for neural oscillations within a frequency range of 18-20 Hz. Beta-band neural oscillations, in the range of 13-30 Hz, were plotted for every stimulation pulse and scalp maps were constructed for the entire scalp. Statistical analyses were performed using a one-tailed, paired-sample, t-test correcting for multiple comparisons using False Discovery Rate (FDR; Benjamini & Hochberg, 1995).

Figure 38A:
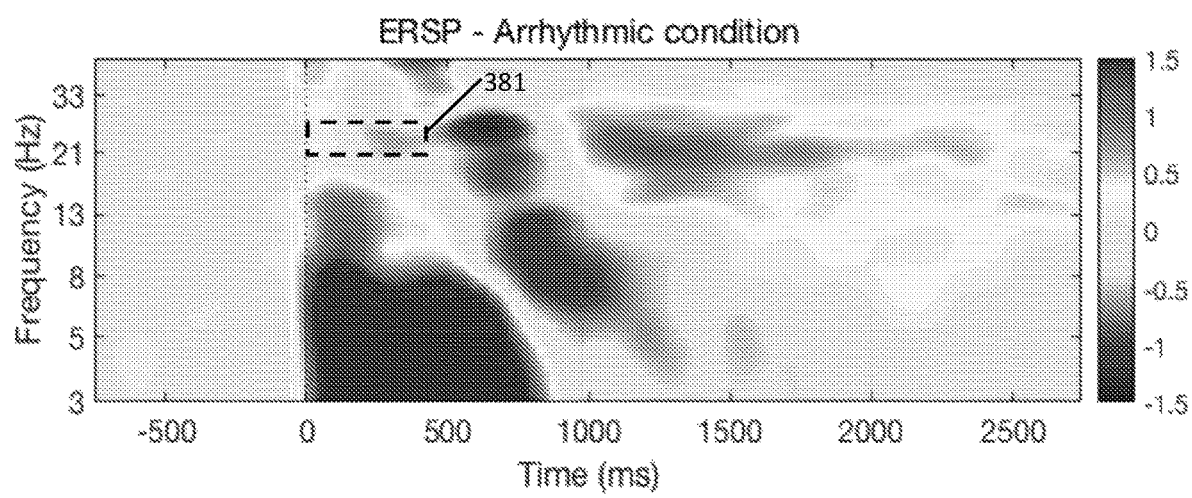
FIG. 38a shows a time-frequency analysis of average ERSP obtained from neural oscillations of each participant of the sixth study recorded at electrode C1 before, during and after delivery of an arrhythmic pulse train.
Figure 38B:
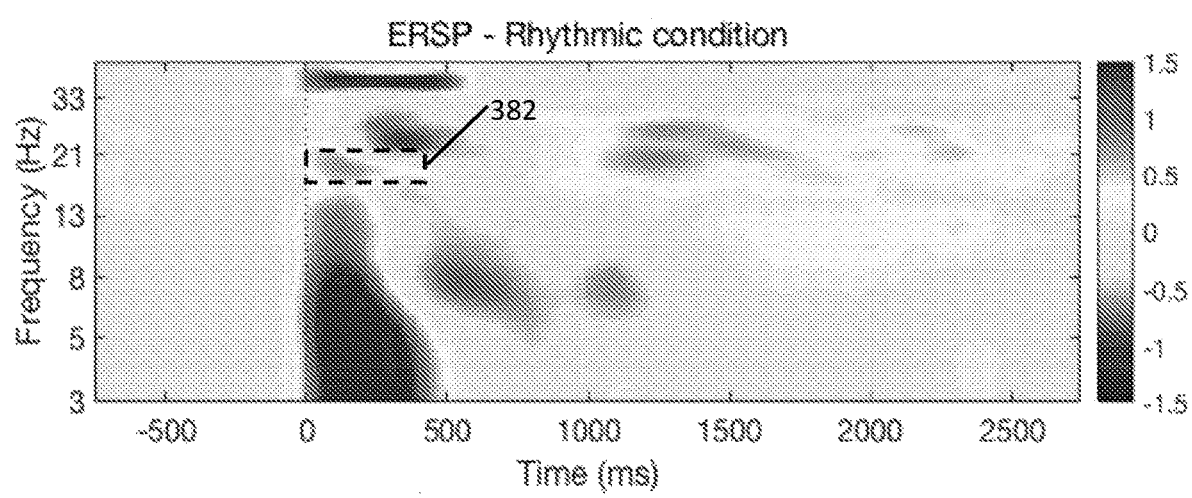
FIG. 38b shows a time-frequency analysis of average ERSP obtained from neural oscillations of each participant of the sixth study recorded at electrode C1 before, during and after delivery of a rhythmic pulse train.
Figure 38C:
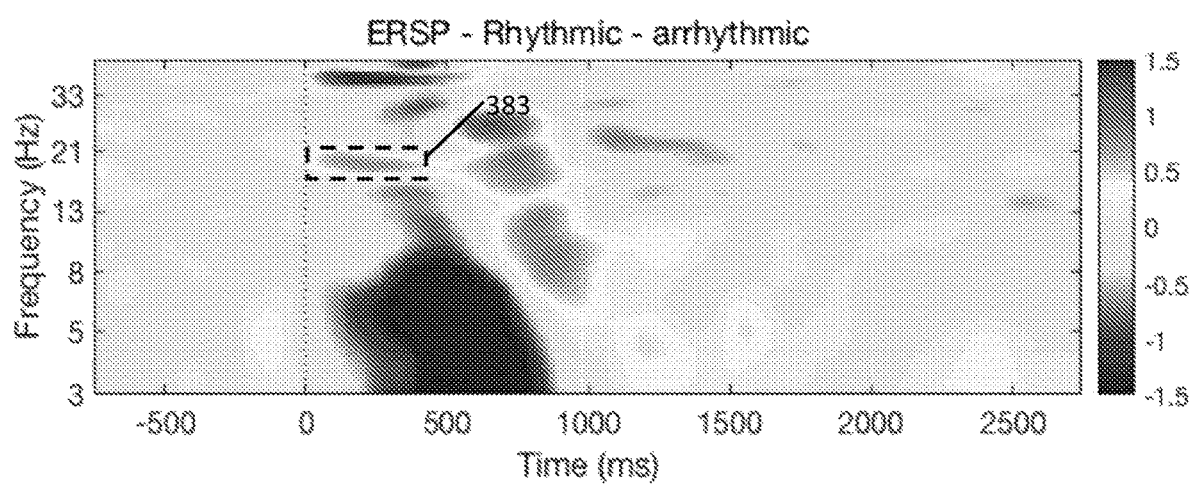
FIG. 38c shows the ERSP values of FIG. 38a subtracted from the ERSP values of FIG. 38b across the same time and frequency range.

FIG. 38*a* shows a time-frequency analysis of average ERSP obtained from neural oscillations of each participant of the study recorded at electrode C1 before, during and after delivery of an arrhythmic pulse train. FIG. 38*b* shows a time-frequency analysis of average ERSP obtained from neural oscillations of each participant of the study recorded at electrode C1 before, during and after delivery of a rhythmic pulse train. FIG. 38*c* shows the ERSP values of FIG. 38*a* subtracted from the ERSP values of FIG. 38*b* across the same time and frequency range. Time is shown on the x-axis and frequency is shown on the y-axis of each of the graphs of FIGS. 38*a-c*. The colouring of the graphs of FIGS. 38*a-c* shows ERSP according to the scale shown. Time=0 on each graph represents the onset of the respective pulse train.

FIGS. 38*a-c* show an increase in ERSP at the beginning of the pulse train for both the rhythmic and arrhythmic conditions that involved both Mu-band (8-12 Hz) and Beta-band (13-30 Hz) neural oscillations. By contrast, after that initial increase in ERSP, there was a sustained increase in ERSP in the rhythmic condition in a narrow band of neural oscillations that peaked at the frequency of the stimulation (i.e. 19 Hz). This is indicated by the area labelled 382 in FIG. 38*b*. This increase in ERSP centred at 19 Hz was absent in the arrhythmic condition, as indicated by the area labelled 381 in FIG. 38*a*. This difference is indicated by the area labelled 383 in FIG. 38*c*.

Figure 39:
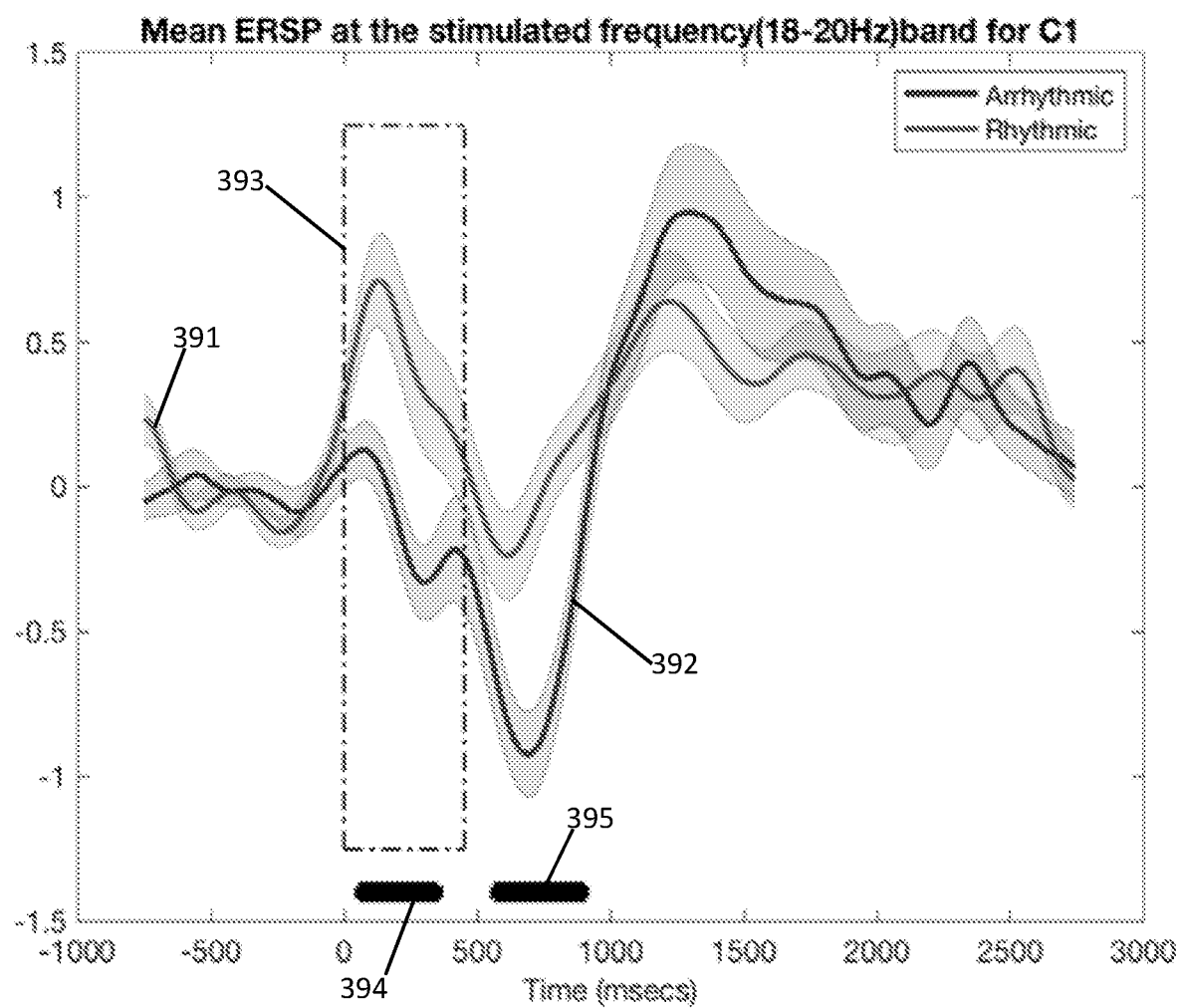
FIG. 39 shows mean ERSP obtained from neural oscillations at the same frequency as the frequency of rhythmic stimulation, i.e. 19 Hz, of each participant of the sixth study recorded at electrode C1 against time.

FIG. 39 shows mean ERSP obtained from neural oscillations at the same frequency as the frequency of rhythmic stimulation, i.e. 19 Hz, of each participant of the study recorded at electrode C1 against time. FIG. 39 shows mean ERSP before, during and after delivery of a rhythmic pulse train (line 391) and before, during and after delivery of an arrhythmic pulse train (line 392). Time is shown on the x-axis and ERSP is shown on the y-axis. Time=0 represents the onset of the respective pulse train. The area labelled 393 indicates the time period of delivery of the respective pulse train. The bars labelled 394 and 395 indicate periods of time during which the difference between ERSP for the rhythmic and arrhythmic pulse trains was statistically significant.

FIG. 39 shows a significant ($p<0.05^{FDR-corrected}$) increase in mean ERSP for rhythmic stimulation relative to arrhythmic stimulation during the period of stimulation from 78 ms to 375 ms (bar 394). FIG. 39 also demonstrates a statistically significant ($p<0.05^{FDR-corrected}$) decrease in mean ERSP for arrhythmic stimulation relative to rhythmic stimulation immediately following the end of the respective period of stimulation (bar 395). This result indicates that rhythmic stimulation at a frequency selected from the same frequency range as Beta-band neural oscillations appears to significantly reduce the magnitude of desynchronization of Beta-band neural oscillations.

Figure 40A:
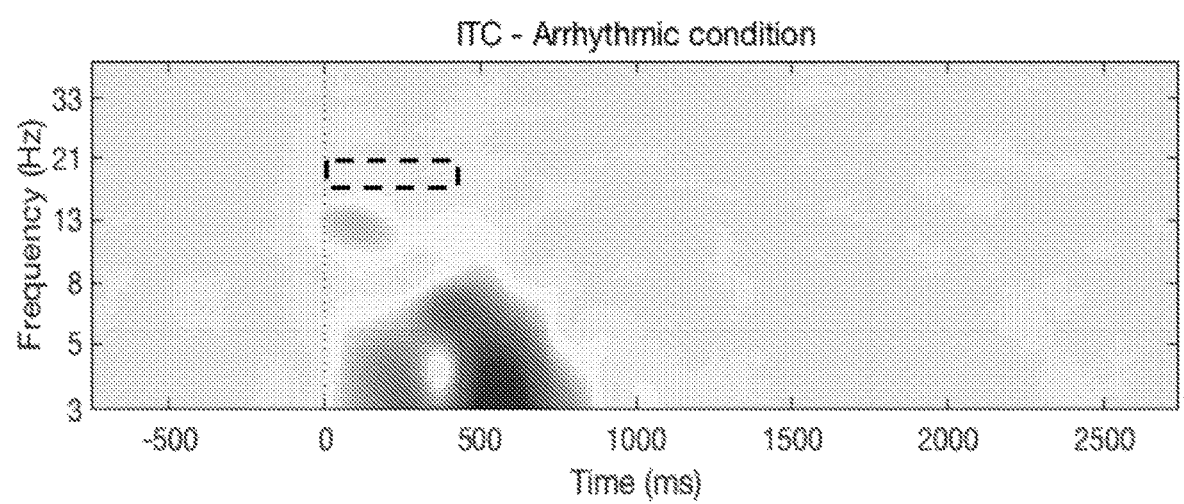
FIG. 40a shows a time-frequency analysis of PLV obtained from neural oscillations of each participant of the sixth study recorded at electrode C1 before, during and after delivery of an arrhythmic pulse train beginning at t=0.
Figure 40B:
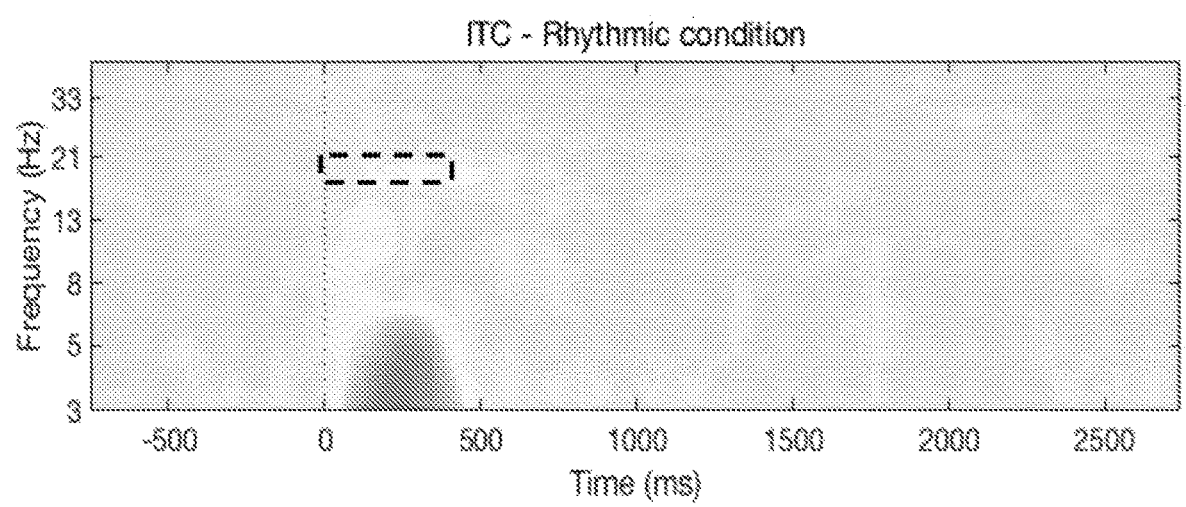
FIG. 40b shows a time-frequency analysis of PLV obtained from neural oscillations of each participant of the sixth study recorded at electrode C1 before, during and after delivery of a rhythmic pulse train beginning at t=0.
Figure 40C:
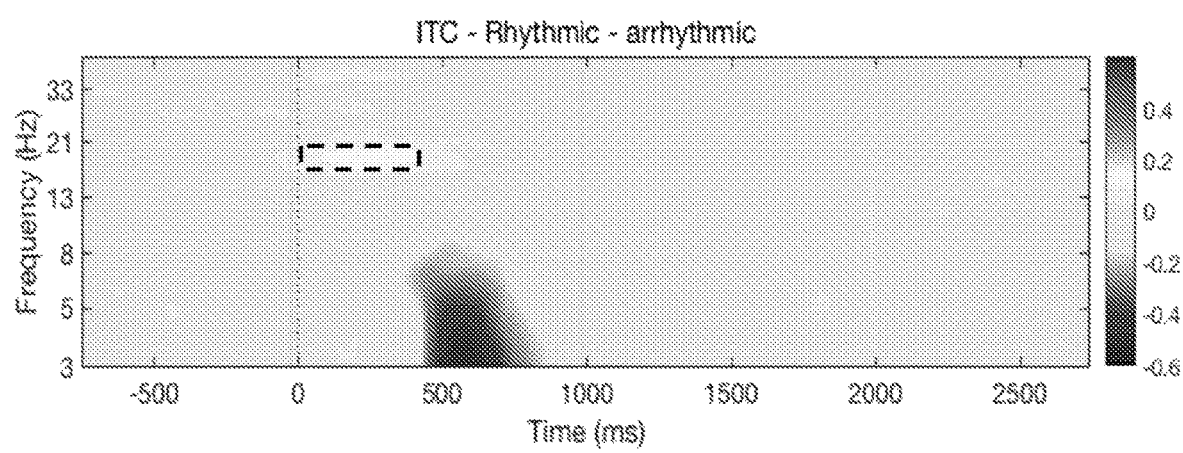
FIG. 40c shows a time-frequency analysis of the PLV values of FIG. 40a subtracted from the PLV values of FIG. 40b over the same time and frequency range.

FIG. 40a shows a time-frequency analysis of PLV obtained from neural oscillations of each participant of the study recorded at electrode C1 before, during and after delivery of an arrhythmic pulse train beginning at t=0. FIG. 40b shows a time-frequency analysis of PLV obtained from neural oscillations of each participant of the study recorded at electrode C1 before, during and after delivery of a rhythmic pulse train beginning at t=0. FIG. 40c shows a time-frequency analysis of the difference between PLV during delivery of an arrhythmic pulse train beginning at t=0 and PLV during delivery of a rhythmic pulse train beginning at t=0. The colouring of the graphs shows PLV (darker colouring showing greater PLV). FIGS. 40a-c demonstrate an increase in PLV (i.e. ITC) at the beginning of the pulse trains for both rhythmic and arrhythmic stimulation that involved both Mu-band and Beta-band neural oscillations. Following this initial phase, an increase in ITC is shown for the rhythmic condition within a narrow band of neural oscillations that peaked at the frequency of the stimulation (i.e. 19 Hz). This increase in ITC centred at 19 Hz was absent in the arrhythmic condition. This difference is shown in FIG. 40c.

Figure 41:
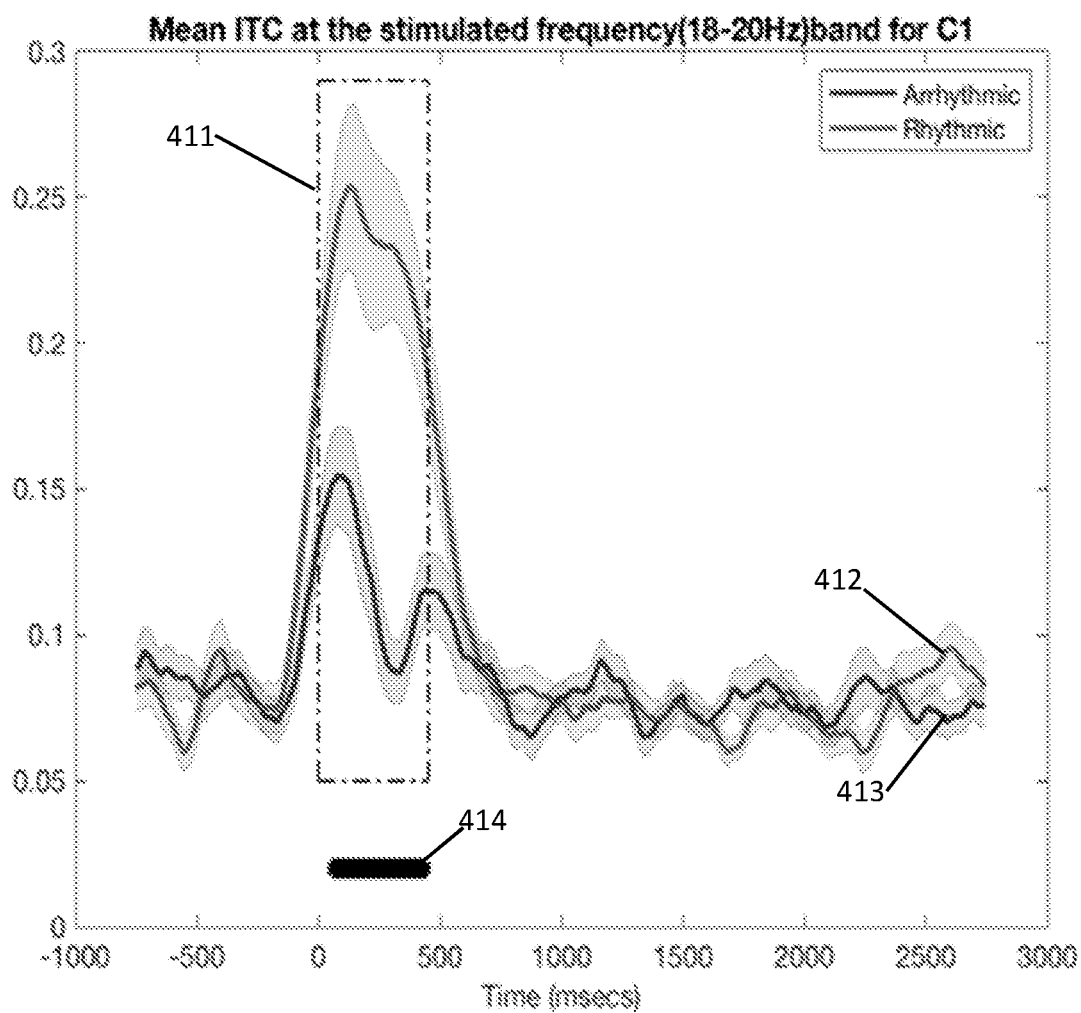
FIG. 41 shows a graph of mean PLV obtained from neural oscillations at the same frequency as the frequency of rhythmic stimulation, i.e. 19 Hz, of each participant of the sixth study recorded at electrode C1 against time.

FIG. 41 shows a graph of mean PLV obtained from neural oscillations at the same frequency as the frequency of rhythmic stimulation, i.e. 19 Hz, of each participant of the study recorded at electrode C1 against time. FIG. 41 shows mean PLV before, during and after delivery of a rhythmic pulse train (line 412) and before, during and after delivery of an arrhythmic pulse train (line 413). Time is shown on the x-axis and PLV is shown on the y-axis. Time=0 represents the onset of the respective pulse train. The area labelled 411 indicates the time period of delivery of the respective pulse train. The bar labelled 414 indicates a period of time during which the difference between PLV for the rhythmic and arrhythmic pulse trains was statistically significant.

FIG. 41 shows a sustained increase in ITC for the rhythmic condition during the time period of stimulation from 54 ms to 460 ms ($p<0.05^{FDR-corrected}$). There is no significant difference between the rhythmic and arrhythmic conditions after the period of stimulation. This suggests that the increased ITC for the rhythmic condition during the time period of stimulation from 54 ms to 460 ms is very likely driven by the individual pulses of the rhythmic pulse train.

Figure 42:
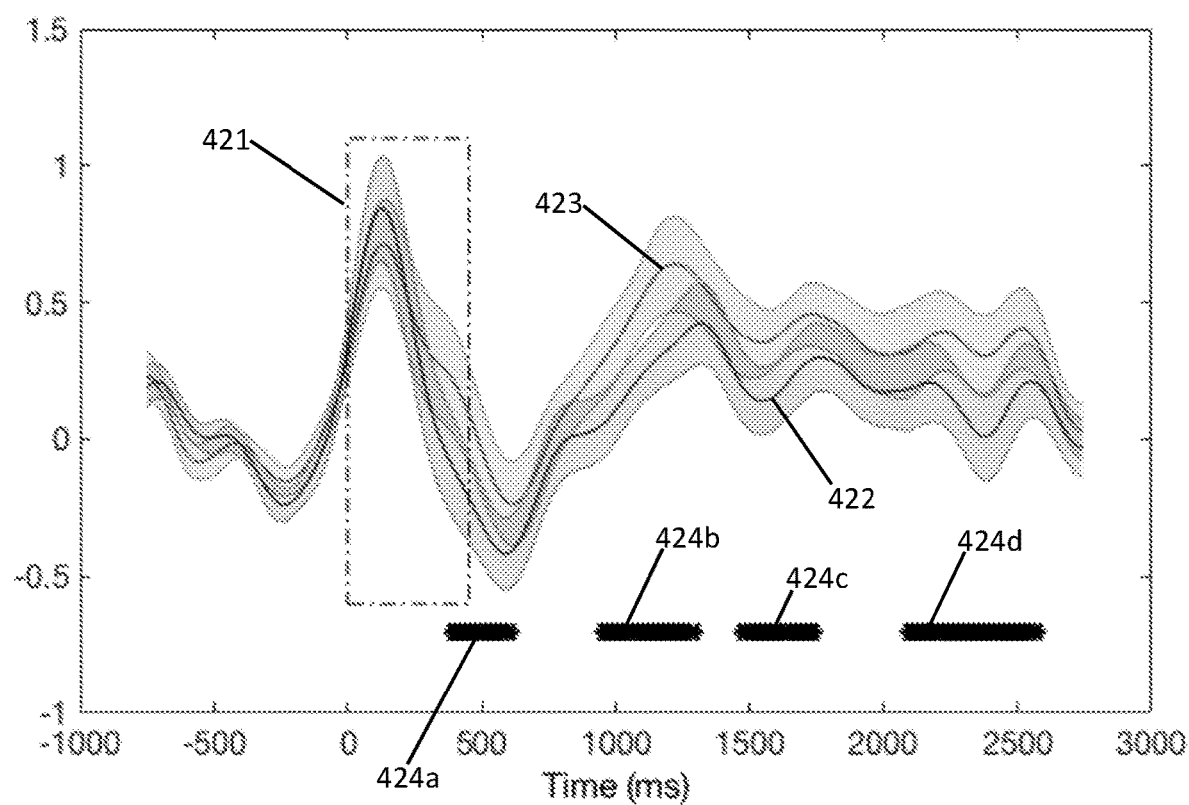
FIG. 42 shows mean ERSP obtained from 19 Hz neural oscillations of each participant of the sixth study before, during and after delivery of a rhythmic pulse train measured at electrode C1 and at electrode C2 (line 413) against time.

FIG. 42 shows mean ERSP obtained from 19 Hz neural oscillations of each participant before, during and after delivery of a rhythmic pulse train measured at electrode C1 (line 423) and at electrode C2 (line 422) against time. Electrode C2 corresponds to the ipsilateral hemisphere of the brain of each participant, i.e. the hemisphere of the brain on the same side of the body as the wrist to which the electrical stimulation is delivered. Electrode C1 corresponds to the contralateral hemisphere of the brain, i.e. the opposite hemisphere. Time is shown on the x-axis and ERSP is shown on the y-axis. Time=0 represents the onset of the respective pulse train. The area labelled 421 indicates the period of delivery of the respective pulse train. The bars labelled 424a-d indicate periods of time during which the difference between ERSP for electrode C1 and electrode C2 was statistically significant.

FIG. 42 shows an initial increase in ERSP at the beginning of the rhythmic pulse train at both the contralateral and ipsilateral hemispheres. However, this is followed by a sustained increase in ERSP at the contralateral hemisphere compared to the ipsilateral hemisphere ($p<0.05^{FDR-corrected}$). This increase in ERSP at the contralateral hemisphere is sustained after stimulation has ceased (i.e., from 984 ms to 1265 ms, from 1476 ms to 1687 ms and from 2093 ms to 2531 ms).

Figure 43:
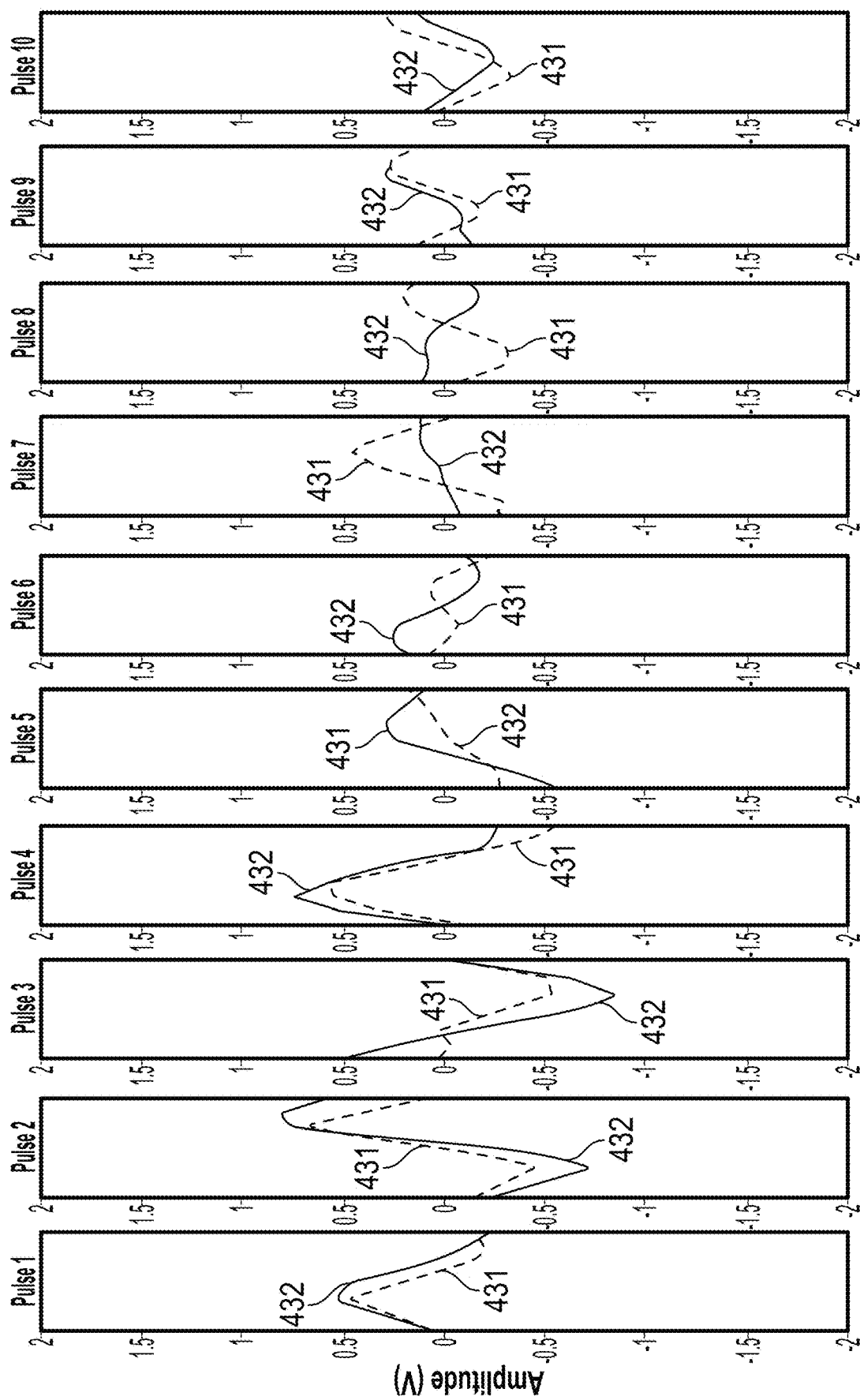
FIG. 43 shows a plot of neural oscillations at 19 Hz recorded during each of the 10 pulses of both an arrhythmic train and a rhythmic train of the sixth study.

FIG. 43 shows a plot of average neural oscillations at 19 Hz across all of the participants recorded during each of the 10 pulses of both an arrhythmic train (line 432) and a rhythmic train (line 431). FIG. 43 shows that stimulation during a rhythmic train leads to the re-setting of the phase occurring after every pulse of the train. This phase-reset is only seen for the first 3 pulses in the arrhythmic train. This is consistent with the increase in ERSP and increase in PLV (ITC) seen at the beginning of the arrhythmic train, and the sustained increase in ERSP and PLV, centred at 19 Hz, for pulses 4-10 only during rhythmic stimulation.

Figure 44:
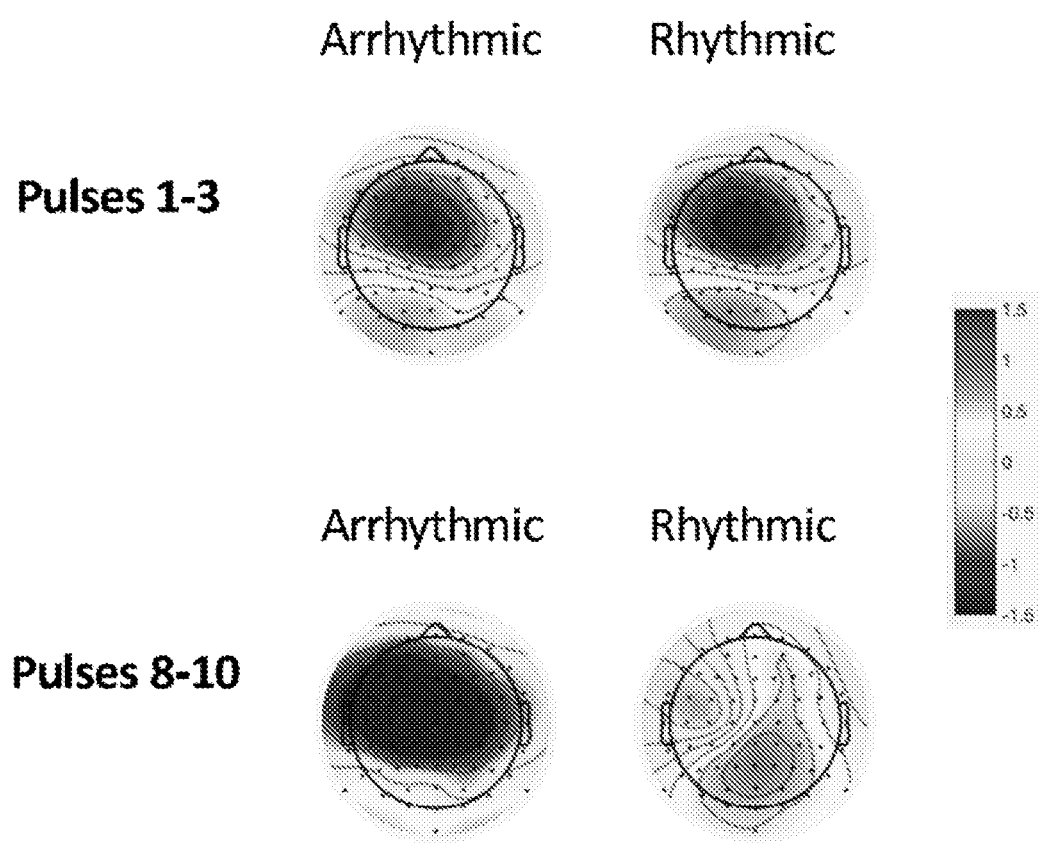
FIG. 44 shows scalp maps of the average event-related potential (ERP) of Beta-band neural oscillations of all participants recorded during the sixth study for pulses 1-3 and pulses 8-10 for both the rhythmic and arrhythmic stimulation.

FIG. 44 shows scalp maps of the average event-related potential (ERP) Beta-band (13-30 Hz) neural oscillations of all the participants, plotted using all electrodes, separately for pulses 1-3 (0-150 ms) (top two scalp maps) and pulses 8-10 (350-500 ms) (bottom two scalp maps), for both the rhythmic (left-hand side scalp maps) and arrhythmic (right-hand side scalp maps) conditions. FIG. 44 shows that for pulses 1-3 there was no significant difference in ERPs between the rhythmic and arrhythmic conditions at any of the 64 electrode positions. By contrast, for pulses 8-10 there is a significant difference ($p<0.05$) in ERPs between the rhythmic and arrhythmic conditions.

Figure 45A:
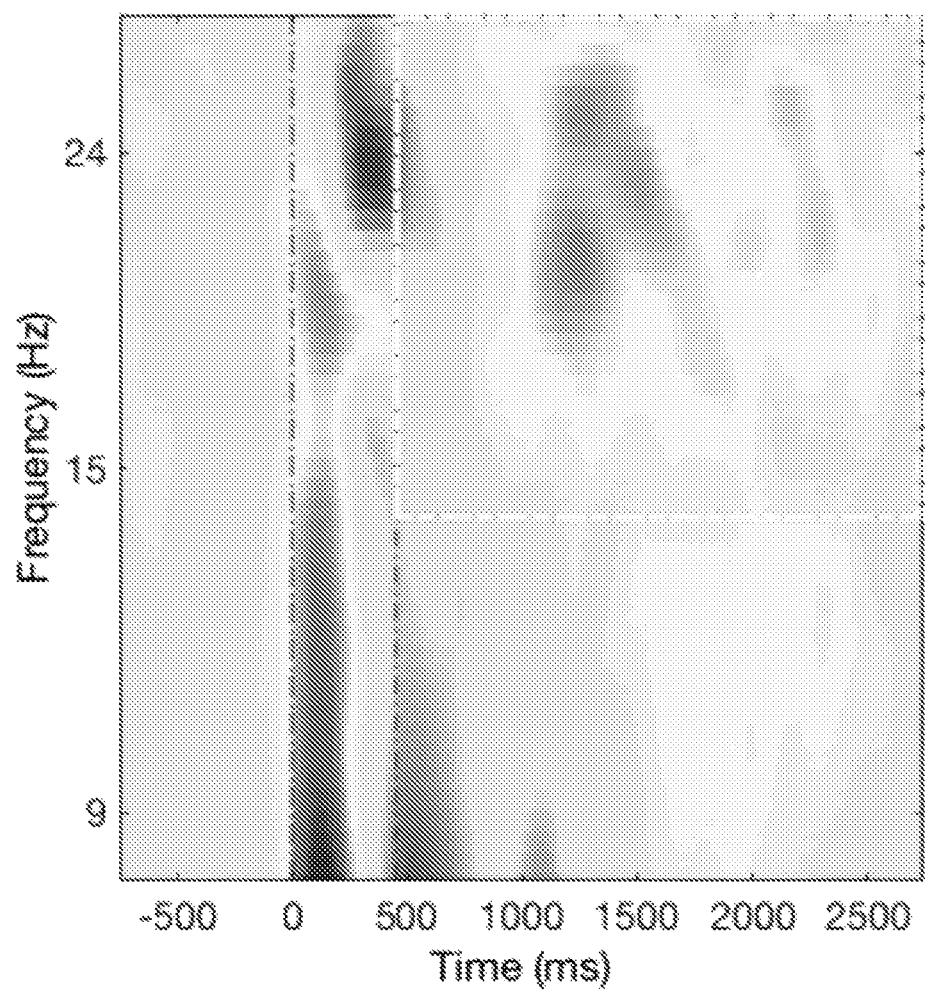
FIG. 45a shows a time-frequency analysis of ERSP before, during and after a period of rhythmic stimulation beginning at t=0.
Figure 45B:
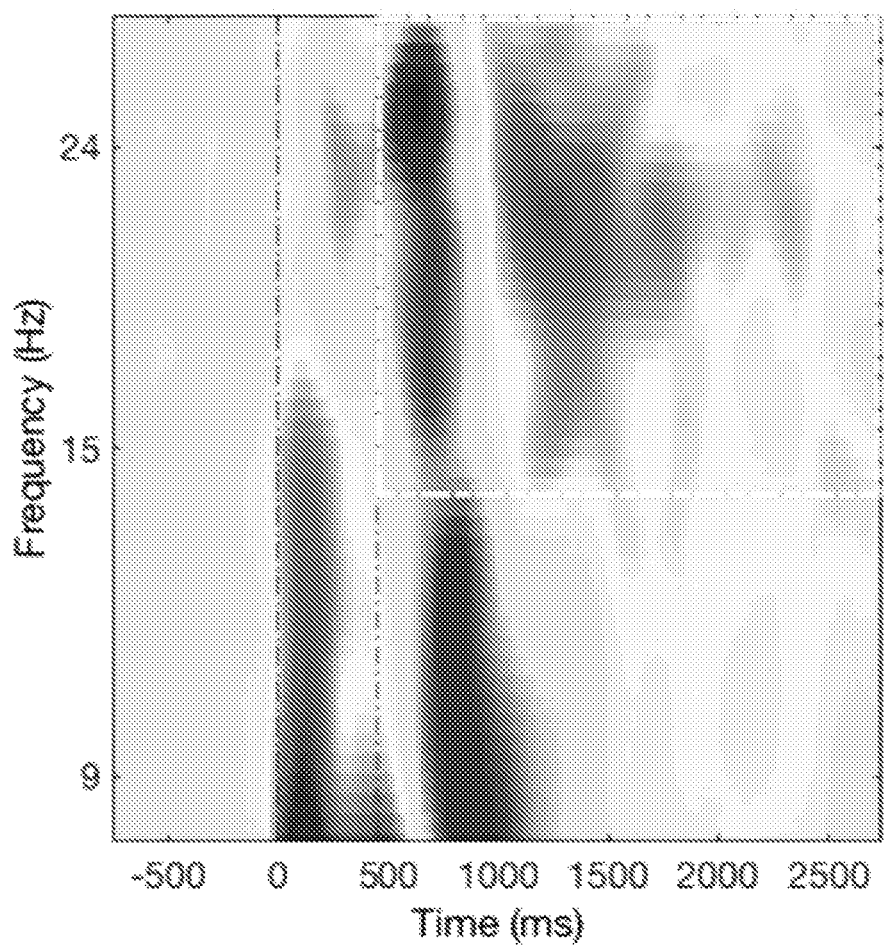
FIG. 45b shows a time-frequency analysis of ERSP before, during and after a period of arrhythmic stimulation beginning at t=0.

FIG. 45a shows a time-frequency analysis of ERSP before, during and after a period of rhythmic stimulation beginning at t=0. FIG. 45b shows a time-frequency analysis of ERSP before, during and after a period of arrhythmic stimulation beginning at t=0. FIGS. 45a-b show greater ERD of Beta-band and Mu-band neural oscillations following the period of arrhythmic stimulation compared to ERD of Beta-band and Mu-band neural oscillations following the period of rhythmic stimulation. FIGS. 45a-b also show a greater rebound effect, i.e. ERSP not returning to baseline levels but instead overshooting and increasing beyond baseline levels, of Beta-band neural oscillations following the period of arrhythmic stimulation than following the period of rhythmic stimulation. This suggests that ERD of Beta-band and Mu-band neural oscillations, and Beta-band rebound effects, which are associated with movement initiation, can be significantly reduced using rhythmic stimulation with a frequency selected from the same frequency range as Beta-band neural oscillations.

Figure 46:
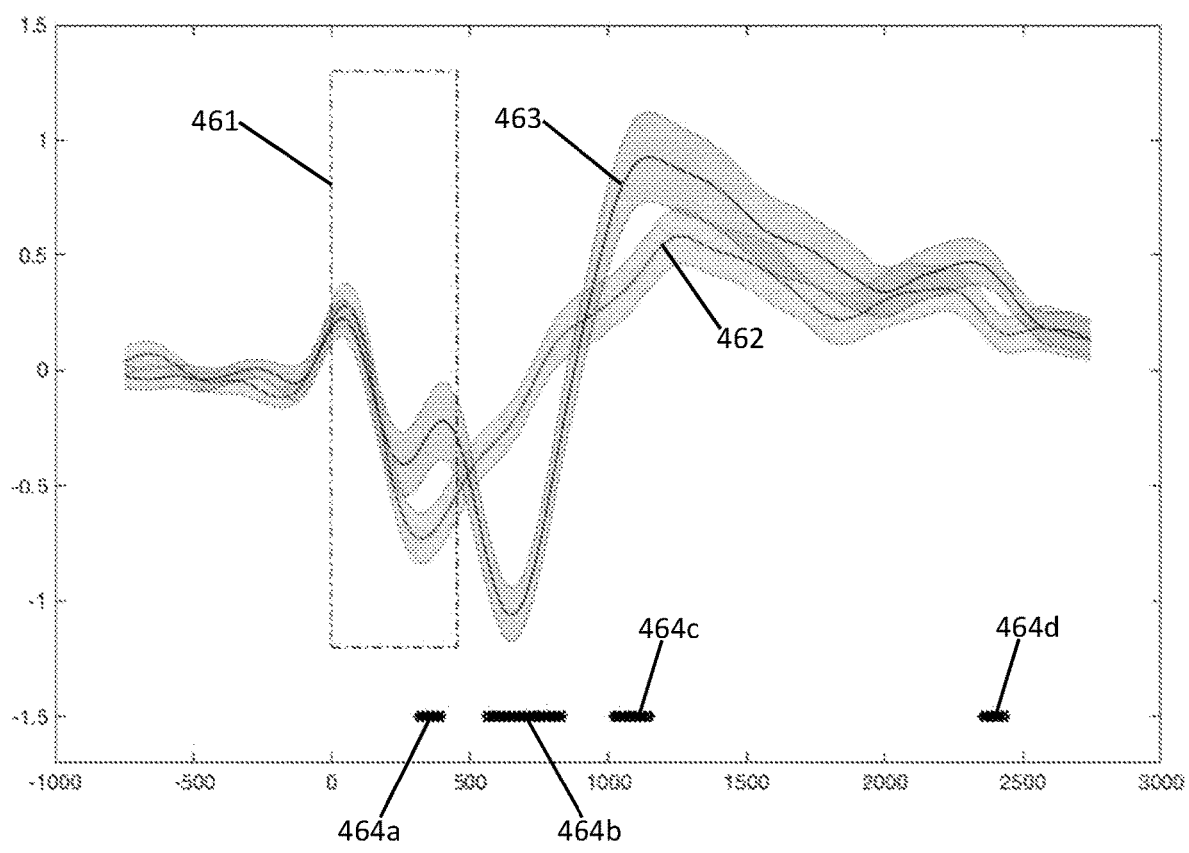
FIG. 46 shows mean ERSP, obtained from 19 Hz neural oscillations of each participant of the sixth study recorded at electrode C1, against time before, during and after delivery of a rhythmic pulse train and before, during and after delivery of an arrhythmic pulse train.

FIG. 46 shows mean ERSP, obtained from 19 Hz neural oscillations of each participant of the study recorded at electrode C1, against time before, during and after delivery of a rhythmic pulse train (line 462) and before, during and after delivery of an arrhythmic pulse train (line 463). Time is shown on the x-axis and ERSP is shown on the y-axis. Time=0 represents the onset of the respective pulse train. The area labelled 461 indicates the period of delivery of the respective pulse train.

The bars labelled 464a-d indicate periods of time during which the difference between ERSP for the rhythmic pulse train and the arrhythmic pulse train was statistically significant. FIG. 46 demonstrates an increase in ERD during the final period of delivery of the rhythmic pulse train, represented by bar 464a, compared to the same period of delivery of the arrhythmic pulse train. Decreased ERD occurs during the period immediately after delivery of the rhythmic pulse train, represented by bar 464b, compared to the same period after delivery of the arrhythmic pulse train. Increased ERS occurs after delivery of the rhythmic pulse train, during the time periods represented by bars 464c and 464d, compared to the same time periods after delivery of the arrhythmic pulse train.

FIG. 47 shows mean ERSP, obtained from Mu-band neural oscillations of each participant of the study recorded at electrode C1, against time before, during and after delivery of a rhythmic pulse train (line 472) and before, during and after delivery of an arrhythmic pulse train (line 473). Time is shown on the x-axis and ERSP is shown on the y-axis. Time=0 represents the onset of the respective pulse train. The area labelled 471 indicates the period of delivery of the respective pulse train.

The bars labelled 474a-b indicate periods of time during which the difference between ERSP for the rhythmic pulse train and the arrhythmic pulse train was statistically significant. FIG. 47 demonstrates an increase in ERD during the final period of delivery of the rhythmic pulse train, represented by bar 474a, compared to the same period of delivery of the arrhythmic pulse train. A decrease in ERD occurs immediately after the delivery of the rhythmic pulse train, during a period of time represented by bar 474b, compared to the same period of time after delivery of the arrhythmic pulse train.

Although the above studies and the invention relate to the intentional entrainment of Mu-band and Beta-band neural oscillations, it will be appreciated that the same or similar techniques may be applicable to oscillations at other frequencies, for example Theta-band neural oscillations, that may have implications for the occurrence of tics. In addition, the stimulation techniques described above may be used to reduce the power and synchronisation of neural oscillations. For example, repetitive arrhythmic peripheral nerve stimulation, such as median nerve stimulation, may be used to reduce the power and synchronisation of Beta-band neural oscillations to decrease symptoms of Parkinson's disease. The electrical nerve stimulator and methods disclosed herein may also be applicable to the treatment of other neurological disorders, such as obsessive compulsive disorder (OCD) and tinnitus.

The invention claimed is:

1. An electrical nerve stimulator, comprising: a power source, a controller and an electrode comprising a first electrode part and a second electrode part;
wherein the electrode is configured to:
i) be wearable on the wrist of the user to deliver an electrical signal to a median nerve of a user;
ii) space apart the first electrode part and the second electrode part by a fixed distance that does not exceed 30 mm; and
iii) position the first electrode part proximal to a hand of the user and the second electrode proximal to an arm of the user, when worn on the wrist of the user;
wherein the controller is configured to deliver the electrical signal via the first electrode part and the second electrode part and the electrical signal comprises a plurality of trains of square pulses, at least one of the trains of square pulses having a frequency of 8 Hz to 30 Hz and a pulse period of up to 0.2 ms;
wherein each train of square pulses comprises between three and ten pulses;
wherein at least one of the trains of square pulses comprises non-uniform intervals between pulses.

2. The electrical nerve stimulator of claim 1, wherein a conducting part of the electrode comprises stainless steel.

3. The electrical nerve stimulator of claim 1, wherein the electrode comprises a bar electrode.

4. The electrical nerve stimulator of claim 1, wherein one or both of the first part and the second part comprises a disc.

5. The electrical nerve stimulator of claim 1, wherein one or both of the first part and the second part comprises a diameter of 8 mm.

6. The electrical nerve stimulator of claim 1, wherein the electrical nerve stimulator is configured to deliver the electrical signal to a hemisphere of the brain of the user that is contralateral to the median nerve.

7. The electrical nerve stimulator of claim 1, wherein the electrical nerve stimulator is configured to entrain Mu-band neural oscillations at a frequency within the range of 8-12 Hz and/or Beta-band neural oscillations at a frequency within the range of 13-30 Hz.

8. The electrical nerve stimulator of claim 1, wherein the electrical signal comprises a duration of longer than 200 ms.

9. The electrical nerve stimulator of claim 1, further comprising a wrist strap.

10. The electrical nerve stimulator of claim 9, wherein the wrist strap is configured to position the electrode with the first electrode part proximal to the hand and the second electrode proximal to the arm, when the wrist strap is worn on the wrist.

11. The electrical nerve stimulator of claim 1, wherein an intensity of the pulses is a minimum needed to generate a thumb twitch in the user.

12. The electrical nerve stimulator of claim 1, wherein the electrical signal is configured to entrain Mu-band neural oscillations and/or Beta-band neural oscillations.

13. The electrical nerve stimulator of claim 1, wherein the controller is configured to provide a separation between successive pulse trains of at least 4 seconds.

14. A method of delivering an electrical signal to a median nerve of a user, comprising:
positioning a wearable electrode on a wrist of a user with a first electrode portion spaced apart from a second electrode portion by a distance that does not exceed 30 mm, with the first electrode part proximal to a hand of the user and the second electrode proximal to an arm of the user;
stimulating the median nerve of the user with an electrical signal delivered via the first electrode portion and the second electrode portion, the electrical signal comprising a plurality of trains of square pulses, at least one of the trains of square pulses having a frequency of 8 Hz to 30 Hz and a pulse period of up to 0.2 ms;
wherein at least one of the trains of square pulses comprises non-uniform intervals between pulses.

15. The method of claim 14, comprising delivering the electrical signal for a duration longer than 200 ms.

16. The method of claim 14, wherein the delivery of the electrical signal to the median nerve of the user comprises treating a symptom of a tic disorder.

* * * * *